US008540997B2

(12) United States Patent
Tomlinson et al.

(10) Patent No.: US 8,540,997 B2
(45) Date of Patent: Sep. 24, 2013

(54) COMPLEMENT RECEPTOR 1 AND 2 FUSION PROTEINS

(75) Inventors: Stephen Tomlinson, Mount Pleasant, SC (US); V. Michael Holers, Denver, CO (US)

(73) Assignees: MUSC Foundation for Research Development, Charleston, SC (US); The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/162,434

(22) Filed: Jun. 16, 2011

(65) Prior Publication Data

US 2012/0015872 A1    Jan. 19, 2012

Related U.S. Application Data

(63) Continuation of application No. 10/534,772, filed as application No. PCT/US03/36459 on Nov. 13, 2003, now Pat. No. 8,007,804.

(60) Provisional application No. 60/426,676, filed on Nov. 15, 2002.

(51) Int. Cl.
*A61K 39/00* (2006.01)

(52) U.S. Cl.
USPC ...................................................... 424/178.1

(58) Field of Classification Search
None
See application file for complete search history.

(56) References Cited

U.S. PATENT DOCUMENTS

| | | | |
|---|---|---|---|
| 4,883,784 A | 11/1989 | Kaneko | |
| 5,212,071 A | 5/1993 | Fearon et al. | |
| 5,260,203 A | 11/1993 | Ladner et al. | |
| 5,328,470 A | 7/1994 | Nabel et al. | |
| 5,472,939 A | 12/1995 | Fearon et al. | |
| 5,679,546 A | 10/1997 | Ko et al. | |
| 5,851,528 A | 12/1998 | Ko et al. | |
| 5,981,481 A | 11/1999 | Fearon et al. | |
| 6,140,472 A | 10/2000 | Rosengard et al. | |
| 6,248,365 B1 | 6/2001 | Römisch et al. | |
| 6,291,239 B1 | 9/2001 | Prodinger et al. | |
| 6,432,679 B1 | 8/2002 | Mond et al. | |
| 6,458,360 B1 | 10/2002 | Fearon et al. | |
| 6,503,947 B1 | 1/2003 | Lipton et al. | |
| 6,521,450 B1 | 2/2003 | Atkinson et al. | |
| 6,820,011 B2 | 11/2004 | Chen et al. | |
| 6,897,290 B1 | 5/2005 | Atkinson et al. | |
| 7,759,304 B2 | 7/2010 | Gilkeson et al. | |
| 8,007,804 B2 | 8/2011 | Tomlinson et al. | |
| 2002/0103346 A1 | 8/2002 | Vogel et al. | |
| 2005/0265995 A1 | 12/2005 | Tomlinson et al. | |
| 2006/0002944 A1 | 1/2006 | Ashkenazi et al. | |
| 2006/0014681 A1 | 1/2006 | Chen et al. | |
| 2006/0178308 A1 | 8/2006 | Schwaeble et al. | |
| 2006/0263819 A1 | 11/2006 | Hageman et al. | |
| 2007/0224197 A1 | 9/2007 | Chen et al. | |
| 2008/0221011 A1 | 9/2008 | Gilkeson et al. | |
| 2008/0267980 A1 | 10/2008 | Tomlinson et al. | |
| 2011/0015127 A1 | 1/2011 | Gilkeson et al. | |
| 2012/0014952 A1 | 1/2012 | Tomlinson et al. | |
| 2012/0015871 A1 | 1/2012 | Tomlinson et al. | |
| 2012/0171206 A1 | 7/2012 | Tomlinson et al. | |

FOREIGN PATENT DOCUMENTS

| | | |
|---|---|---|
| EP | 0 402 226 A1 | 12/1990 |
| JP | 5-507197 A | 10/1993 |
| JP | 9-502985 A | 3/1997 |
| JP | 2002-534959 | 10/2002 |
| WO | WO-91/16437 A1 | 10/1991 |
| WO | WO-98/07835 A2 | 2/1998 |
| WO | WO-98/07835 A3 | 2/1998 |
| WO | WO 00/34317 | 6/2000 |
| WO | WO-2004/045520 A2 | 6/2004 |
| WO | WO-2004/045520 A3 | 6/2004 |
| WO | WO-2004/103288 A2 | 12/2004 |
| WO | WO-2004/103288 A3 | 12/2004 |
| WO | WO-2007/035857 A2 | 3/2007 |
| WO | WO-2007/035857 A3 | 3/2007 |

OTHER PUBLICATIONS

Abrahmsen, L. et al. (Apr. 30, 1991). "Engineering Subtilisin and Its Substrates for Efficient Ligation of Peptide Bonds in Aqueous Solution," *Biochemistry* 30(17):4151-4159.

Ahearn, J.M. et al. (Mar. 1996). "Disruption of the *Cr2* Locus Results in a Reduction in B-1a Cells and in an Impaired B Cell Response to T-Dependent Antigen," *Immunity* 4(3):251-262.

Amsterdam, E.A. et al. (Jan. 1995). "Limitation of Reperfusion Injury by a Monoclonal Antibody to C5a During Myocardial Infarction in Pigs," *Am. J. Physiol.* 268(1):H448-H457.

Andrews, B.S. et al. (Oct. 1, 1978). "Spontaneous Murine Lupus-like Syndromes. Clinical and Immunopathological Manifestations in Several Strains," *J. Exp. Med.* 148(4):1198-1215.

Aslam, M. et al. (Jun. 22, 2001). "Folded-Back Solution Structure of Monomeric Factor H of Human Complement by Synchrotron X-ray and Neutron Scattering, Analytical Ultracentrifugation and Constrained Molecular Modelling," *J. Mol. Biol.* 309(5):1117-1138.

Atkinson et al. (2010, e-pub. Oct. 20, 2010). "Targeted Complement Inhibitors Protect Against Posttransplant Cardiac Ischemia and Reperfusion Injury and Reveal an Important Role for the Alternative Pathway of Complement Activation," *J. Immunol.* 185:7007-7013.

Aubry, J-P. et al. (Aug. 6, 1992). "CD21 is a Ligand for CD23 and Regulates IgE Production," *Nature* 358(6386):505-507.

Bagshawe, K.D. et al. (1988). "A Cytotoxic Agent can be Generated Selectively at Cancer Sites," *Br. J. Cancer* 58:700-703.

Bagshawe, K.D. (1989). "Towards Generating Cytotoxic Agents at Cancer Sites," *Br. J. Cancer* 60:275-281.

(Continued)

*Primary Examiner* — Sharon Wen

(74) *Attorney, Agent, or Firm* — Clark & Elbing LLP; Kristina Bieker-Brady

(57) ABSTRACT

Modulation of the complement system represents a therapeutic modality for numerous pathologic conditions associated with complement activation. In a strategy to prepare complement inhibitors that are targeted to sites of complement activation and disease, compositions comprising a complement inhibitor linked to complement receptor (CR) 2 are disclosed. The disclosed are compositions can be used in methods of treating pathogenic diseases and inflammatory conditions by modulating the complement system.

13 Claims, 31 Drawing Sheets

(56) References Cited

OTHER PUBLICATIONS

Baranyi, L. et al. (Aug. 1994). "Cell-Surface Bound Complement Regulatory Activity is Necessary for the in vivo Survival of KDH-8 Rat Hepatoma," *Immunology* 82(4):522-528.

Barlow, P.N. et al. (Jul. 5, 1993). "Solution Structure of a Pair of Complement Modules by Nuclear Magnetic Resonance," *J. Mol. Biol.* 232:268-284.

Battelli, M.G. et al. (1992). "T Lymphocyte Killing by a Xanthine-Oxidase-Containing Immunotoxin," *Cancer Immunol. Immunother.* 35:421-425.

Bergelson, J.M. et al. (Jun. 21, 1994). "Decay-Accelerating Factor (CD55), A Glycosylphosphatidylinositol-Anchored Complement Regulatory Protein, Is a Receptor for Several Echoviruses," *Proc. Natl. Acad. Sci. USA* 91(13):6245-6249.

Brown, V.I. et al. (Jul./Aug. 1991). "Molecular and Cellular Mechanisms of Receptor-Mediated Endocytosis," *DNA and Cell Biology* 10(6):399-409.

Cambier, J.C. (May 1997). "Signalling Processes in Haematopoietic Cells: Positive and Negative Signal Co-operativity in the Immune System: The BCR, FcγRIIB, CR2 Paradigm," *Biochem. Soc. Trans.* 25(2):441-445.

Caragine, T.A. et al. (Feb. 15, 2002). "A Tumor-Expressed Inhibitor of the Early but not Late Complement Lytic Pathway Enhances Tumor Growth in a Rat Model of Human Breast Cancer," *Cancer Res.* 62(4):1110-1115.

Carel, J-C. et al. (Jul. 25, 1990). "Structural Requirements for C3d,g/Epstein-Barr Virus Receptor (CR2/CD21) Ligand Binding, Internalization, and Viral Infection," *J. Biol. Chem.* 265(21):12293-12299.

Carroll, M.C. (1998). "The Role of Complement and Complement Receptors in Induction and Regulation of Immunity," *Annu. Rev. Immunol.* 16:545-568.

Carroll, M.C. (2000). "The Role of Complement in B Cell Activation and Tolerance" *Advances in Immunology*, Dixon, F.J. ed., Academic Press, Inc., 74:61-88.

Carter, R.H. et al. (Apr. 3, 1992). "CD19: Lowering the Threshold for Antigen Receptor Stimulation of B Lymphocytes," *Science* 256:105-107.

Casasnovas, J.M. et al. (1999). "Crystal Structure of Two CD46 Domains Reveals an Extended Measles Virus-Binding Surface," *EMBO J.* 18(11):2911-2922.

Chen, S-H. et al. (Apr. 12, 1994). "Gene Therapy for Brain Tumors: Regression of Experimental Gliomas by Adenovirus-Mediated Gene Transfer in vivo," *Proc. Natl. Acad. Sci. USA* 91(8):3054-3057.

Chen, S. et al. (Jun. 1, 2000). "CD59 Expressed on a Tumor Cell Surface Modulates Decay-Accelerating Factor Expression and Enhances Tumor Growth in a Rat Model of Human Neuroblastoma," *Cancer Res.* 60(11):3013-3018.

Christiansen, D. et al. (Mar. 1996). "A Functional Analysis of Recombinant Soluble CD46 in vivo and a Comparison with Recombinant Soluble Forms of CD55 and CD35 in vitro," *European Journal of Immunology* 26(3):578-585.

Clemenza, L. et al. (Oct. 1, 2000). "Structure-Guided Identification of C3d Residues Essential for Its Binding to Complement Receptor 2 (CD21)," *J. Immunol.* 165(7):3839-3848.

Davies, A. et al. (Sep. 1, 1989). "CD59, an Ly-6-Like Protein Expressed in Human Lymphoid Cells, Regulates the Action of the Complement Membrane Attack Complex on Homologous Cells," *Journal of Experimental Medicine* 170(3):637-654.

de Córdoba, S.R. et al. (2004). "The Human Complement Factor H: Functional Roles, Genetic Variations and Disease Associations," *Molecular Immunology* 41:355-367.

Dempsey, P.W. et al. (Jan. 19, 1996). "C3d of Complement as a Molecular Adjuvant: Bridging Innate and Acquired Immunity," *Science* 271:348-350.

Dev, S.B. et al. (Jan. 1994). "Electrochemotherapy—A Novel Method of Cancer Treatment," *Cancer Treat. Rev.* 20(1):105-115.

Diefenbach, R.J. et al. (Mar. 1, 1995). "Mutation of Residues in the C3dg Region of Human Complement Component C3 Corresponding to a Proposed Binding Site for Complement Receptor Type 2 (CR2, CD21) Does Not Abolish Binding of iC3b or C3dg to CR2," *J. Immunol.* 154(5):2303-2320.

Dierich, M.P. et al. (Nov. 1988). "Structural and Functional Relationships Among Receptors and Regulators of the Complement System," *Mol. Immunol.* 25(11):1043-1051.

Dörig, R.E. et al. (Oct. 22, 1993). "The Human CD46 Molecule Is a Receptor for Measles Virus (Edmonston Strain)," *Cell* 75(2):295-305.

Duits, A.J. et al. (1991). "Selective Enhancement of Leu-Cam Expression by Interleukin 6 During Differentiation of Human Promonocytic U937 Cells," *Scand. J. Immunol.* 33(2):151-159.

Edwards, A.O. et al. (Apr. 15, 2005). "Complement Factor H Polymorphism and Age-Related Macular Degeneration," *Science* 308(5720):421-424.

Fearon, D.T. (Oct. 1998). "The Complement System and Adaptive Immunity," *Semin. Immunol.* 10(5):355-361.

Fearon, D.T. et al. (1995). "The CD19/CR2/TAPA-1 Complex of B Lymphocytes: Linking Natural to Acquired Immunity," *Annu. Rev. Immunol.* 13:127-149.

Fingeroth, J.D. et al. (Jul. 1984). "Epstein-Barr Virus Receptor of Human B Lymphocytes is the C3d Receptor CR2," *Proc. Natl. Acad. Sci. USA* 81(14):4510-4514.

Fingeroth, J.D. et al. (Jan. 1989). "Identification of Murine Complement Receptor Type 2," *Proc. Natl. Acad. Sci. USA* 86(1):242-246.

Frémeaux-Bacchi, V. et al. (Dec. 1998). "Soluble CD21 Induces Activation and Differentiation of Human Monocytes Through Binding to Membrane CD23," *Eur. J. Immunol.* 28:4268-4274.

Fritzinger, D.C. et al. (Dec. 1994). "Molecular Cloning and Derived Primary Structure of Cobra Venom Factor," *Proc. Natl. Acad. Sci. USA* 91(26):12775-12779, correction (1995), 92:1605.

Fukuoka, Y. et al. (1996). "Molecular Cloning of Murine Decay Accelerating Factor by Immunoscreening," *International Immunology* 8(3):379-385.

Girardi, G. et al. (Dec. 2003). "Complement C5a Receptors and Neutrophils Mediate Fetal Injury in the Antiphospholipid Syndrome," *J. Clin. Invest.* 112(11):1644-1654.

Goodford, P.J. (Jul. 1985). "A Computational Procedure for Determining Energetically Favorable Binding Sites on Biologically Important Macromolecules," *J. Med. Chem.* 28(7):849-857.

Gordon, J. (Sep. 1994). "B-cell Signaling via the C-type Lectins CD23 and CD72," *Immunol. Today* 15(9):411-417.

Guthridge, J.M. et al. (Nov. 15, 2001). "Epitope Mapping Using the X-Ray Crystallographic Structure of Complement Receptor Type 2 (CR2)/CD21: Identification of a Highly Inhibitory Monoclonal Antibody That Directly Recognizes the CR2-C3d Interface," *J. Immunol.* 167:5758-5766.

Guthridge, J.M. et al. (May 22, 2001). "Structural Studies in Solution of the Recombinant N-Terminal Pair of Short Consensus/Complement Repeat Domains of Complement Receptor Type 2 (CR2/CD21) and Interactions with its Ligand C3dg," *Biochemistry* 40:5931-5941.

Hageman, G.S. et al. (May 17, 2005). "A Common Haplotype in the Complement Regulatory Gene Factor H (*HF1/CFH*) Predisposes Individuals to Age-Related Macular Degeneration," *Proc. Natl. Acad. Sci. USA* 102(20):7227-7232.

Haines, J.L. et al. (Apr. 15, 2005). "Complement Factor H Variant Increases the Risk of Age-Related Macular Degeneration," *Science* 308:419-421.

Harlow, E. et al. eds. (1988). "Proteolytic Fragments of Antibodies," in Chapter 15 in *Antibodies. A Laboratory Manual*, Cold Spring Harbor Laboratory: Cold Spring Harbor, NY, pp. 626-629.

Harris, C.L. et al. (Nov. 2002). "Tailoring Anti-Complement Therapeutics," *Biochemical Society Transactions* 30(6):1019-1026.

Hebell, T. et al. (Oct. 4, 1991). "Suppression of the Immune Response by a Soluble Complement Receptor of B Lymphocytes," *Science* 254:102-105.

Heyman, B. (2000). "Regulation of Antibody Responses via Antibodies, Complement, and Fc Receptors," *Ann. Rev. Immunol.* 18:709-737.

Higgins, P.J. et al. (Mar. 15, 1997). "A Soluble Chimeric Complement Inhibitory Protein That Possesses Both Decay-Accelerating and Factor I Cofactor Activities," *J. Immunol.* 158(6):2872-2881.

Holers, V.M. (1989). "Complement Receptors" in *The Year In Immunology 1988. Cellular, .Molecular and Clinical Aspects*, Cruse, J.M. et al. eds., Basel, Karger, 4:231-240.

Homeister, J.W. et al. (Feb. 1, 1993). "Soluble Complement Receptor Type 1 Prevents Human Complement-Mediated Damage of the Rabbit Isolated Heart," *J. Immunol.* 150(3):1055-1064.

Hori, Y. et al. (Dec. 1999). "Crry, a Complement Regulatory Protein, Modulates Renal Interstitial Disease Induced by Proteinuria," *Kidney Int.* 56(6):2096-2106.

Hsu, S.I-H. et al. (2003). "Chronic Progression of Tubulointerstitial Damage in Proteinuric Renal Disease Is Mediated by Complement Activation: A Therapeutic Role for Complement Inhibitors?" *J. Am. Soc. Nephrol.* 14:S186-S191.

Hughes, B.J. et al. (Nov. 15, 1989). "Monoclonal Antibody Targeting of Liposomes to Mouse Lung in Vivo," *Cancer Research* 49(22):6214-6220.

Humblet, C. et al. (1993). "3D Database Searching and Docking Strategies" Chapter 29 In "Topics in Drug Design and Discovery" Section VI In *Animal Reports in Medicinal Chemistry*, Bristol, J.A. et al. eds., Academic Press, Inc.: San Diego, CA, 28:275-283.

International Search Report mailed Sep. 15, 2004, for PCT Application No. PCT/US03/36459 filed Nov. 13, 2003, three pages.

Józsi, M. et al. (2004). "Attachment of the Soluble Complement Regulator Factor H to Cell and Tissue Surfaces: Relevance for Pathology," *Histol. Histopathol.* 19:251-258.

Kalli, K.R. et al. (Jul. 15, 1991). "Interaction of iC3b With Recombinant Isotypic and Chimeric Forms of CR2," *J. Immunol.* 147(2):590-594.

Kaplan, M. (2002). "Eculizumab Alexion," *Curr. Opin. Investig. Drugs* 3(7):1017-1023.

Khurana, S. et al. (Jun. 9, 1998). "Crystal Structure of 2,5-diketo-D-gluconic Acid Reductase A Complexed with NADPH at 2.1-Å Resolution," *Proc. Natl. Acad. Sci.* 95(12):6768-6773.

Klein, R.J. et al. (Apr. 15, 2005). "Complement Factor H Polymorphism in Age-Related Macular Degeneration," *Science* 308(5720):385-389.

Koski, C.L. et al. (Jun. 1983). "Cytolysis of Nucleated Cells by Complement: Cell Death Displays Multi-hit Characteristics," *Proc. Natl. Acad. Sci. USA* 80(12):3816-3820.

Kovacs et al. (Apr. 3, 2009). "Mapping of the C3d Ligand Binding Site on Complement Receptor 2 (CR2/CD21) Using Nuclear Magnetic Resonance and Chemical Shift Analysis," *J. Biol. Chem.* 284(14):9513-9520.

Kroshus, T.J. et al. (Dec. 15, 1995). "Complement Inhibition with an Anti-C5 Monoclonal Antibody Prevents Acute Cardiac Tissue Injury in an Ex Vivo Model of Pig-To-Human Xenotransplantation," *Transplantation* 60(11):1194-1202.

Kroshus, T.J. et al. (Jun. 15, 2000). "A Recombinant Soluble Chimeric Complement Inhibitor Composed of Human CD46 and CD55 Reduces Acute Cardiac Tissue Injury in Models of Pig-to-Human Heart Transplantation," *Transplantation* 69(11):2282-2289.

Krushkal, J. et al. (2000). "Evolutionary Relationships Among Proteins Encoded by the Regulator of Complement Activation Gene Cluster," *Molec. Biol. Evol.* 17(11):1718-1730.

Kuby, J. (1994). "Antigens," in Chapter 4 in *Immunology*, W.H. Freeman and Company: New York, 2:85-96.

Kuraya, M. et al. (1992). "Expression of the Complement Regulatory Proteins CD21, CD55, and CD59 on Burkitt Lymphoma Lines: Their Role in Sensitivity to Human Serum-Mediated Lysis," *Eur. J. Immunol.* 22(7):1871-1876.

Lambris, J.D. et al. (Jun. 1985). "Mapping of the C3d Receptor (CR2)-Binding Site and a Neoantigenic Site in the C3d Domain of the Third Component of Complement," *Proc. Natl. Acad. Sci. USA* 82(12):4235-4239.

Law, S.K. et al. (Mar. 1979). "Action of the C3b-Inactivator on Cell-Bound C3b," *J. Immunol.* 122(3):759-765.

Law, S.K.A. et al. (1995). "Complement" In *In Focus*, Second Edition, Male, D. ed., IRL Press at Oxford University Press, Inc.: New York, NY, pp. vii-ix (Table of Contents Only.).

Linton, S.M. et al. (Nov. 2000). "Therapeutic Efficacy of a Novel Membrane-Targeted Complement Regulator in Antigen-Induced Arthritis in the Rat," *Arthritis Rheum.* 43(11):2590-2597.

Liszewski, M.K. et al. (1997). "Complement Inhibitors as Therapeutic Agents," *Clinical Immunology Newsletter* 17(12):168-173.

Litzinger, D.C. et al. (1992). "Biodistribution and Immunotargetability of Ganglioside-Stabilized Dioleoylphosphatidylethanolamine Liposomes," *Biochimica et Biophysica Acta.* 1104:179-187.

Lowell, C.A. et al. (Dec. 1, 1989). "Mapping of the Epstein-Barr Virus and C3dg Binding Sites to a Common Domain on Complement Receptor Type 2," *J. Exp. Med.* 170(6):1931-1946.

Martin, D.R. et al. (Dec. 1991). "Determination of the Structural Basis for Selective Binding of Epstein-Barr Virus to Human Complement Receptor Type 2," *J. Exp. Med.* 174:1299-1311.

Martin, D.R. et al. (Aug. 1994). "Determination of the Role for CD21 During Epstein-Barr Virus Infection of B-Lymphoblastoid Cells," *J. Virol.* 68(8):4716-4726.

Matsumoto, A.K. et al. (Jan. 1, 1991). "Intersection of the Complement and Immune Systems: A Signal Transduction Complex of the B Lymphocyte-Containing Complement Receptor Type 2 and CD19," *J. Exp. Med.* 173(1):55-64.

Matsuo, S. et al. (Jul. 1992). "Complement in Renal Tubulointerstitial Injuries," *Proceedings of the 35$^{th}$ Complement Symposium*, Japan, pp. 21-22.

Mendrick, D.L. et al. (1983). "Monoclonal Antibodies Against Rat Glomerular Antigens: Production and Specificity," *Laboratory Investigation* 49(1):107-117.

Mendrick, D.L. et al. (1988). "I. Induction of Proteinuria in the Rat by a Monoclonal Antibody Against SGP-115/107," *Kidney Int.* 33:818-830.

Meri, S. et al. (Jun. 15, 1996). "Structural Composition and Functional Characterization of Soluble CD59: Heterogeneity of the Oligosaccharide and Glycophosphoinositol (GPI) Anchor Revealed by Laser-Desorption Mass Spectrometric Analysis," *Biochem J.* 316(Pt.3):923-935.

Moir, S. et al. (Sep. 4, 2000). "B Cells of HIV-1-Infected Patients Bind Virions Through CD21-Complement Interactions and Transmit Infectious Virus to Activated T Cells," *J. Exp. Med.* 192(5):637-645.

Mold, C. et al. (Jun. 1, 1988). "Activation of the Alternative Complement Pathway by EBV and the Viral Envelope Glycoprotein gp350," *J. Immunology* 140(11):3867-3874.

Molina, H. et al. (Jul. 5, 1991). "Analysis of Epstein-Barr Virus-Binding Sites on Complement Receptor 2 (CR2/CD21) Using Human-Mouse Chimeras and Peptides," *J. Biol. Chem.* 266(19):12173-12179.

Molina, H. et al. (Jul. 15, 1994). "Analysis of C3b/C3d Binding Sites and Factor I Cofactor Regions Within Mouse Complement Receptor 1 and 2," *J. Immunol.* 153(2):789-795.

Molina, H. et al. (May 15, 1995). "Characterization of a Complement Receptor 2 (CR2, CD21) Ligand Binding Site for C3," *J. Immunol.* 154(10):5426-5435.

Molina, H. et al. (Apr. 1996). "Markedly Impaired Humoral Immune Response in Mice Deficient in Complement Receptors 1 and 2," *Proc. Natl. Acad. Sci. USA* 93:3357-3361.

Moore, M.D. et al. (Jul. 1991). "Inhibition of Epstein-Barr Virus Infection In Vitro and In Vivo by Soluble CR2 (CD21) Containing Two Short Consensus Repeats," *J. Virology* 65(7):3559-3565.

Moran, P. et al. (Sep. 1, 1992). "Human Recombinant Soluble Decay Accelerating Factor Inhibits Complement Activation in vitro and in vivo," *J. Immunol.* 149(5):1736-1743.

Morgan, B.P. (Apr. 1994). "Clinical Complementology: Recent Progress and Future Trends," *Eur. J. Clin. Invest.* 24(4):219-228.

Müller-Eberhard, H.J. (1988). "Molecular Organization and Function of the Complement System," *Ann. Rev. Biochem.* 57:321-347.

Mulligan, M.S. et al. (Apr. 15, 1999). "Endothelial Targeting and Enhanced Antiinflammatory Effects of Complement Inhibitors Possessing Sialyl Lewis$^x$ Moieties," *J. Immunol.* 162(8):4952-4959.

Nagar, B. et al. (May 22, 1998). "X-Ray Crystal Structure of C3d: A C3 Fragment and Ligand for Complement Receptor 2," *Science* 280:1277-1281.

Ngo, J.T. et al. (1994). "Computational Complexity, Protein Structure Prediction, and the Levinthal Paradox," Chapter 14 in *The Protein Folding and Tertiary Structure Prediction*, Merz, K. et al. eds., Birkhauser Publishing: Boston, MA, pp. 491-495.

Okano, M. (Jan. 1998). "Epstein-Barr Virus Infection and its Role in the Expanding Spectrum of Human Diseases," *Acta Paediatr.* 87:11-18.

Piatesi, A. et al. (2004). "Immunological Optimization of a Generic Hydrophobic Pocket for High Affinity Hapten Binding and Diels-Alder Activity," *ChemBioChem* 5:460-466.

Pietersz, G.A. et al. (1992). "Antibody Conjugates for the Treatment of Cancer," *Immunolog. Reviews* 129:57-80.

Poznansky, M.C. et al. (Aug. 15, 1989). "The Difference Between Human C3F and C3S Results From a Single Amino Acid Change From an Asparagine to an Aspartate Residue at Position 1216 on the α-Chain of the Complement Component, C3," *J. Immunol.* 143(4):1254-1258.

Prodeus, A.P. et al. (Nov. 1998). "A Critical Role for Complement in Maintenance of Self-Tolerance," *Immunity* 9(5):721-731.

Prodinger, W.M. et al. (Nov. 1, 1998). "Characterization of C3dg Binding to a Recess Formed Between Short Consensus Repeats 1 and 2 of Complement Receptor Type 2 (CR2; CD21)," *J. Immunol.* 161(9):4604-4610.

Quigg, R.J. et al. (May 1, 1998). "Blockade of Antibody-Induced Glomerulonephritis with Crry-Ig, a Soluble Murine Complement Inhibitor," *J. Immunol.* 160(9):4553-4560.

Quigg, R.J. et al. (Jan. 2000). "Production and Functional Analysis of Rat CD59 and Chimeric CD59-Crry as Active Soluble Proteins in *Pichia pastoris*," *Immunology* 99(1):46-53.

Rabinovici, R. et al. (Sep. 1, 1992). "Role of Complement in Endotoxin/Platelet-Activating Factor-Induced Lung Injury," *J. Immunol.* 149(5):1744-1750.

Ramm, L.E. et al. (Aug. 1982). "Transmembrane Channel Formation by Complement: Functional Analysis of the Number of C5b6, C7, C8, and C9 Molecules Required for a Single Channel," *Proc. Natl. Acad. Sci. USA* 79(15):4751-4755.

Rao, P.E. et al. (Jul. 1985). "OKB7, A Monoclonal Antibody That Reacts at or Near the C3d Binding Site of Human CR2," *Cell. Immunol.* 93(2):549-555.

Rinder, C.S. et al. (Sep. 1995). "Blockade of C5a and C5b-9 Generation Inhibits Leukocyte and Platelet Activation During Extracorporeal Circulation," *J. Clin. Invest.* 96(3):1564-1572.

Rioux, P. (2001). "TP-10 AVANT Immunotherapeutics," *Curr. Opin. Investig. Drugs* 2:364-371.

Ritterhaus, C.W. et al. (Apr. 16, 1999). "Recombinant Glycoproteins That Inhibit Complement Activation and Also Bind the Selectin Adhesion Molecules," *J. Biol. Chem.* 274(16):11267-11244.

Roffler, S.R. et al. (Oct. 24, 1991). "Anti-Neoplastic Glucuronide Prodrug Treatment of Human Tumor Cells Targeted with a Monoclonal Antibody-Enzyme Conjugate," *Biochem. Pharmacol.* 42(10):2062-2065.

Ross, G.D. et al. (Feb. 1992). "Macrophage Cytoskeleton Association with CR3 and CR4 Regulates Receptor Mobility and Phagocytosis of iC3b-opsonized Erythrocytes," *J. Leukoc. Biol.* 51(2):109-117.

Rothlein, R. et al. (May 1, 1986). "The Requirement for Lymphocyte Function-Associated Antigen 1 in Homotypic Leukocyte Adhesion Stimulated by Phorbol Ester," *J. Exp. Med.* 163(5):1132-1149.

Rudikoff, S. et al. (Mar. 1982). "Single Amino Acid Substitution Altering Antigen-Binding Specificity," *Proc. Natl. Acad. Sci.* 79:1979-1983.

Rushmere, N.K. et al. (Feb. 2000). "Production and Functional Characterization of a Soluble Recombinant Form of Mouse CD59," *Immunology* 99(2):326-332.

Salerno, C.T. et al. (Mar. 2002). "A Soluble Chimeric Inhibitor of C3 and C5 Convertases, Complement Activation Blocker-2, Prolongs Graft Survival in Pig-to-Rhesus Monkey Heart Transplantation," *Xenotransplantation* 9(2):125-134.

Schwarzenbacher, R. et al. (Nov. 15, 1999). "Crystal Structure of Human β2-glycoprotein I: Implications for Phospholipid Binding and the Antiphospholipid Syndrome," *EMBO J.* 18(22):6228-6239.

Senter, P.D. et al. (Nov./Dec. 1991). "Generation of 5-Fluorouracil From 5-Fluorocytosine by Monoclonal Antibody-Cytosine Deaminase Conjugates," *Bioconjugate Chem.* 2(6):447-451.

Senter, P.D. et al. (Jan./Feb. 1993). "Generation of Cytotoxic Agents by Targeted Enzymes," *Bioconjugate Chem.* 4(1):3-9.

Seya, T. et al. (1985). "Limited Proteolysis of Complement Protein C3b by Regulatory Enzyme C3b Inactivator: Isolation and Characterization of a Biologically Active Fragment, C3d,g," *J. Biochem.* 97(1):373-382.

Sharkey, R.M. et al. (Apr. 15, 1990). "Biodistribution and Radiation Dose Estimates for Yttrium- and Iodine-Labeled Monoclonal Antibody IgG and Fragments in Nude Mice Bearing Human Colonic Tumor Xenografts," *Cancer Res.* 50:2330-2336.

Sharkey, R.M. et al. (Jun. 15, 1991). "Rapid Blood Clearance of Immunoglobulin G2a and Immunoglobulin G2b in Nude Mice," *Cancer Res.* 51:3102-3107.

Sheerin, N.S. et al. (Oct. 2002). "Leaked Protein and Interstitial Damage in the Kidney: Is Complement the Missing Link?" *Clin. Exp. Immunol.* 130(1):1-3.

Smith, G.P. et al. (2001). "Membrane-Targeted Complement Inhibitors," *Mol. Immunol.* 38:249-255.

Song, H. et al. (Jun. 2003). "Complement Receptor 2-Mediated Targeting of Complement Inhibitors to Sites of Complement Activation," *J. Clin. Invest.* 111(12):1875-1885.

Styer, L. et al. (1998). "Levels of Structure in Protein Architecture," in Chapter 2 in *Biochemistry*, W.H. Freeman and Company: New York, 3:31-33.

Sugita, Y. et al. (May 1994). "Recombinant Soluble CD59 Inhibits Reactive Haemolysis with Complement," *Immunology* 82(1):34-41.

Supplementary Partial European Search Report mailed Apr. 3, 2006, for EP Application No. 03796403.8 filed Nov. 13, 2003, three pages.

Supplementary European Search Report mailed Jul. 3, 2006, for EP Application No. 03796403.8 filed Nov. 13, 2003, four pages.

Szakonyi, G. et al. (Jun. 1, 2001). "Structure of Complement Receptor 2 in Complex with Its C3d Ligand," *Science* 292(5522):1725-1728.

Takeda, J. et al. (1986). "Number of Hits Necessary for Complement-Mediated Hemolysis," *Microbiol. Immunol.* 30(5):461-468.

Ten, R.M. et al. (Oct. 1, 1999). "The Signal Transduction Pathway of CD23 (FcεRIIb) Targets IκB Kinase," *J. Immunol.* 163(7):3851-3857.

Tsutsumi, Y. et al. (Jul. 18, 2000). "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity," *Proc. Natl. Acad. Sci. USA* 97(15):8548-8553.

Wang, Y. et al. (Sep. 12, 1995). "Anti-C5 Monoclonal Antibody Therapy Prevents Collagen-Induced Arthritis and Ameliorates Established Disease," *Proc. Natl. Acad. Sci. USA* 92(19):8955-8959.

Wang, Y. et al. (Aug. 6, 1996). "Amelioration of Lupus-Like Autoimmune Disease in NZB/WF$_1$ Mice After Treatment with a Blocking Monoclonal Antibody Specific for Complement Component C5," *Proc. Natl. Acad. Sci. USA* 93(16):8563-8568.

Ward, T. et al. (Nov. 1, 1994). "Decay-Accelerating Factor CD55 is Identified as the Receptor for Echovirus 7 Using CELICS, a Rapid Immuno-Focal Cloning Method," *EMBO J.* 13(21):5070-5074.

Watanabe, M. et al. (2000). "Co-Protective Effect of Crry and CD59 in Rat Kidney Against Complement Attack," *Proceedings of the Joint Academic Meeting of the Complement Symposium and Japanese Society for Host Defense Research* 37(11):19-20.

Weisman, H.F. et al. (Jul. 13, 1990). "Soluble Human Complement Receptor Type 1: In Vivo Inhibitor of Complement Suppressing Post-Ischemic Myocardial Inflammation and Necrosis," *Science* 249(4965):146-151.

Whiss, P.A. (2002). "Pexelizumab Alexion," *Curr. Opin. Investig. Drugs* 3(6):870-877.

Wiles, A.P. et al. (1997). "NMR Studies of a Viral Protein that Mimics the Regulators of Complement Activation," *J. Mol. Biol.* 272(2):253-265.

Yu, J. et al. (Jan. 1999). "Protection of Human Breast Cancer Cells from Complement-Mediated Lysis by Expression of Heterologous CD59," *Clin. Exp. Immunol.* 115(1):13-18.

Zhang, H-F. et al. (Jul. 20, 2001). "Targeting of Functional Antibody-Decay-Accelerating Factor Fusion Proteins to a Cell Surface," *J. Biol. Chem.* 276(29):27290-27295.

Zhang, H-F. et al. (Jan. 1999). "Targeting of Functional Antibody-CD59 Fusion Proteins to a Cell Surface," *J. Clin. Invest.* 103(1):55-66.

Zhu, Z. et al. (1999). "Inhibition of Tumor Growth and Metastasis by Targeting Tumor-Associated Angiogenesis with Antagonists to the Receptors of Vascular Endothelial Growth Factor," *Investigational New Drugs* 17:195-212.

Zipfel, P.F. (Jun. 2001). "Complement Factor H: Physiology and Pathophysiology," *Seminars in Thrombosis Hemostasis* 27(3):191-199.

Ferreira and Pangburn, "Factor H-mediated cell surface protection from complement is critical for the survival of PNH erythrocytes," *Blood* 110: 2190-2192, 2007.

Reeck et al., "Homology in proteins and nucleic acids: a terminology muddle and a way out of it," *Cell* 50: 667, 1987.

Sharma and Pangburn, "Identification of three physically and functionally distinct binding sites for C3b in human complement factor H by deletion mutagenesis," *Proc. Natl. Acad. Sci. USA* 93: 10996-11001, 1996.

Leu et al., "Triggering of Interferon γ-Primed Macrophages by Various Known Complement Activators for Nonspecific Tumor Cytotoxicity," *Cell. Immunol.* 106:114-121, 1987.

Juhl et al., "Complement Killing of Human Neuroblastoma Cells: A Cytotoxic Monoclonal Antibody and its F(ab)'$_2$-Cobra Venom Factor Conjugate Are Equally Cytotoxic," *Mol. Immunol.* 27(10):957-964, 1990.

FIGURE 8

```
Sequence: CR2CD59      Length: 1002
ATT TCT TGT GGC TCT CCT CCG CCT ATC CTA AAT GGC CGG ATT AGT  45
 I   S   C   G   S   P   P   P   I   L   N   G   R   I   S
TAT TAT TCT ACC CCC ATT GCT GTT GGT ACC GTG ATA AGG TAC AGT  90
 Y   Y   S   T   P   I   A   V   G   T   V   I   R   Y   S
TGT TCA GGT ACC TTC CGC CTC ATT GGA GAA AAA AGT CTA TTA TGC  135
 C   S   G   T   F   R   L   I   G   E   K   S   L   L   C
ATA ACT AAA GAC AAA GTG GAT GGA ACC TGG GAT AAA CCT GCT CCT  180
 I   T   K   D   K   V   D   G   T   W   D   K   P   A   P
AAA TGT GAA TAT TTC AAT AAA TAT TCT TCT TGC CCT GAG CCC ATA  225
 K   C   E   Y   F   N   K   Y   S   S   C   P   E   P   I
GTA CCA GGA GGA TAC AAA ATT AGA GGC TCT ACA CCC TAC AGA CAT  270
 V   P   G   G   Y   K   I   R   G   S   T   P   Y   R   H
GGT GAT TCT GTG ACA TTT GCC TGT AAA ACC AAC TTC TCC ATG AAC  315
 G   D   S   V   T   F   A   C   K   T   N   F   S   M   N
GGA AAC AAG TCT GTT TGG TGT CAA GCA AAT AAT ATG TGG GGG CCG  360
 G   N   K   S   V   W   C   Q   A   N   N   M   W   G   P
ACA CGA CTA CCA ACC TGT GTA AGT GTT TTC CCT CTC GAG TGT CCA  405
 T   R   L   P   T   C   V   S   V   F   P   L   E   C   P
GCA CTT CCT ATG ATC CAC AAT GGA CAT CAC ACA AGT GAG AAT GTT  450
 A   L   P   M   I   H   N   G   H   H   T   S   E   N   V
GGC TCC ATT GCT CCA GGA TTG TCT GTG ACT TAC AGC TGT GAA TCT  495
 G   S   I   A   P   G   L   S   V   T   Y   S   C   E   S
GGT TAC TTG CTT GTT GGA GAA AAG ATC ATT AAC TGT TTG TCT TCG  540
 G   Y   L   L   V   G   E   K   I   I   N   C   L   S   S
GGA AAA TGG AGT GCT GTC CCC CCC ACA TGT GAA GAG GCA CGC TGT  585
 G   K   W   S   A   V   P   P   T   C   E   E   A   R   C
AAA TCT CTA GGA CGA TTT CCC AAT GGG AAG GTA AAG GAG CCT CCA  630
 K   S   L   G   R   F   P   N   G   K   V   K   E   P   P
ATT CTC CGG GTT GGT GTA ACT GCA AAC TTT TTC TGT GAT GAA GGG  675
 I   L   R   V   G   V   T   A   N   F   F   C   D   E   G
TAT CGA CTG CAA GGC CCA CCT TCT AGT CGG TGT GTA ATT GCT GGA  720
 Y   R   L   Q   G   P   P   S   S   R   C   V   I   A   G
CAG GGA GTT GCT TGG ACC AAA ATG CCA GTA TGT TCA GGA GGA GGA  765
 Q   G   V   A   W   T   K   M   P   V   C   S   G   G   G
GGT TCC CTG CAG TGC TAC AAC TGT CCT AAC CCA ACT GCT GAC TGC  810
 G   S   L   Q   C   Y   N   C   P   N   P   T   A   D   C
AAA ACA GCC GTC AAT TGT TCA TCT GAT TTT GAT GCG TGT CTC ATT  855
 K   T   A   V   N   C   S   S   D   F   D   A   C   L   I
ACC AAA GCT GGG TTA CAA GTG TAT AAC AAG TGT TGG AAG TTT GAG  900
 T   K   A   G   L   Q   V   Y   N   K   C   W   K   F   E
CAT TGC AAT TTC AAC GAC GTC ACA ACC CGC TTG AGG GAA AAT GAG  945
 H   C   N   F   N   D   V   T   T   R   L   R   E   N   E
CTA ACG TAC TAC TGC TGC AAG AAG GAC CTG TGT AAC TTT AAC GAA  990
 L   T   Y   Y   C   C   K   K   D   L   C   N   F   N   E
CAG CTT GAA AAT 1035
 Q   L   E   N
```

Sequence: CD59CR2    Length: 1035

```
CTG CAG TGC TAC AAC TGT CCT AAC CCA ACT GCT GAC TGC AAA ACA 45
 L   Q   C   Y   N   C   P   N   P   T   A   D   C   K   T
GCC GTC AAT TGT TCA TCT GAT TTT GAT GCG TGT CTC ATT ACC AAA 90
 A   V   N   C   S   S   D   F   D   A   C   L   I   T   K
GCT GGG TTA CAA GTG TAT AAC AAG TGT TGG AAG TTT GAG CAT TGC 135
 A   G   L   Q   V   Y   N   K   C   W   K   F   E   H   C
AAT TTC AAC GAC GTC ACA ACC CGC TTG AGG GAA AAT GAG CTA ACG 180
 N   F   N   D   V   T   T   R   L   R   E   N   E   L   T
TAC TAC TGC TGC AAG AAG GAC CTG TGT AAC TTT AAC GAA CAG CTT 225
 Y   Y   C   C   K   K   D   L   C   N   F   N   E   Q   L
GAA AAT TCC TCT GGT GGC GGT GGC TCC GGC GGA GGT GGG TCC GGT 270
 E   N   S   S   G   G   G   G   S   G   G   G   G   S   G
GGC GGC GGA TCC ATT TCT TGT GGC TCT CCT CCG CCT ATC CTA AAT 315
 G   G   G   S   I   S   C   G   S   P   P   P   I   L   N
GGC CGG ATT AGT TAT TAT TCT ACC CCC ATT GCT GTT GGT ACC GTG 360
 G   R   I   S   Y   Y   S   T   P   I   A   V   G   T   V
ATA AGG TAC AGT TGT TCA GGT ACC TTC CGC CTC ATT GGA GAA AAA 405
 I   R   Y   S   C   S   G   T   F   R   L   I   G   E   K
AGT CTA TTA TGC ATA ACT AAA GAC AAA GTG GAT GGA ACC TGG GAT 450
 S   L   L   C   I   T   K   D   K   V   D   G   T   W   D
AAA CCT GCT CCT AAA TGT GAA TAT TTC AAT AAA TAT TCT TCT TGC 495
 K   P   A   P   K   C   E   Y   F   N   K   Y   S   S   C
CCT GAG CCC ATA GTA CCA GGA GGA TAC AAA ATT AGA GGC TCT ACA 540
 P   E   P   I   V   P   G   G   Y   K   I   R   G   S   T
CCC TAC AGA CAT GGT GAT TCT GTG ACA TTT GCC TGT AAA ACC AAC 585
 P   Y   R   H   G   D   S   V   T   F   A   C   K   T   N
TTC TCC ATG AAC GGA AAC AAG TCT GTT TGG TGT CAA GCA AAT AAT 630
 F   S   M   N   G   N   K   S   V   W   C   Q   A   N   N
ATG TGG GGG CCG AGA CGA CTA CCA ACC TGT GTA AGT GTT TTC CCT 675
 M   W   G   P   T   R   L   P   T   C   V   S   V   F   P
CTC GAG TGT CCA GCA CTT CCT ATG ATC CAC AAT GGA CAT CAC ACA 720
 L   E   C   P   A   L   P   M   I   H   N   G   H   H   T
AGT GAG AAT GTT GGC TCC ATT GCT CCA GGA TTG TGT GTG ACT TAC 765
 S   E   N   V   G   S   I   A   P   G   L   S   V   T   Y
AGC TGT GAA TCT GGT TAC TTG CTT GTT GGA GAA AAG ATC ATT AAC 810
 S   C   E   S   G   Y   L   L   V   G   E   K   I   I   N
TGT TTG TCT TCG GGA AAA TGG AGT GCT GTC CCC CCC ACA TGT GAA 855
 C   L   S   S   G   K   W   S   A   V   P   P   T   C   E
GAG GCA CGC TGT AAA TCT CTA GGA CGA TTT CCC AAT GGG AAG GTA 900
 E   A   R   C   K   S   L   G   R   F   P   N   G   K   V
AAG GAG CCT CCA ATT CTC CGG GTT GGT GTA ACT GCA AAC TTT TTC 945
 K   E   P   P   I   L   R   V   G   V   T   A   N   F   F
TGT GAT GAA GGG TAT CGA CTG CAA GGC CCA CCT TCT AGT CGG TGT 990
 C   D   E   G   Y   R   L   Q   G   P   P   S   S   R   C
1035
```

FIGURE 11

```
Sequence: CR2Fc                    Length: 1530
ATG GGC GCC GCG GGC CTG CTC GGG GTT TTC TTG GCT CTC GTC GCA  45
 M   G   A   A   G   L   L   G   V   F   L   A   L   V   A
CCG GGG GTC CTC GGG ATT TCT TGT GGC TCT CCT CCG CCT ATC CTA  90
 P   G   V   L   G   I   S   C   G   S   P   P   P   I   L
AAT GGC CGG ATT AGT TAT TAT TCT ACC CCC ATT GCT GTT GGT ACC 135
 N   G   R   I   S   Y   Y   S   T   P   I   A   V   G   T
GTG ATA AGG TAC AGT TGT TCA GGT ACC TTC CGC CTC ATT GGA GAA 180
 V   I   R   Y   S   C   S   G   T   F   R   L   I   G   E
AAA AGT CTA TTA TGC ATA ACT AAA GAC AAA GTG GAT GGA ACC TGG 225
 K   S   L   L   C   I   T   K   D   K   V   D   G   T   W
GAT AAA CCT GCT CCT AAA TGT GAA TAT TTC AAT AAA TAT TCT TCT 270
 D   K   P   A   P   K   C   E   Y   F   N   K   Y   S   S
TGC CCT GAG CCC ATA GTA CCA GGA GGA TAC AAA ATT AGA GGC TCT 315
 C   P   E   P   I   V   P   G   G   Y   K   I   R   G   S
ACA CCC TAC AGA CAT GGT GAT TCT GTG ACA TTT GCC TGT AAA ACC 360
 T   P   Y   R   H   G   D   S   V   T   F   A   C   K   T
AAC TTC TCC ATG AAC GGA AAC AAG TCT GTT TGG TGT CAA GCA AAT 405
 N   F   S   M   N   G   N   K   S   V   W   C   Q   A   N
AAT ATG TGG GGG CCG ACA CGA CTA CCA ACC TGT GTA AGT GTT TTC 450
 N   M   W   G   P   T   R   L   P   T   C   V   S   V   F
CCT CTC GAG TGT CCA GCA CTT CCT ATG ATC CAC AAT GGA CAT CAC 495
 P   L   E   C   P   A   L   P   M   I   H   N   G   H   H
ACA AGT GAG AAT GTT GGC TCC ATT CCT CCA GGA TTG TCT GTG ACT 540
 T   S   E   N   V   G   S   I   P   P   G   L   S   V   T
TAC AGC TGT GAA TCT GGT TAC TTG CTT GTT GGA GAA AAG ATC ATT 585
 Y   S   C   E   S   G   Y   L   L   V   G   E   K   I   I
AAC TGT TTG TCT TCG GGA AAA TGG AGT GCT GTC CCC CCC ACA TGT 630
 N   C   L   S   S   G   K   W   S   A   V   P   P   T   C
GAA GAG GCA CGC TGT AAA TCT CTA GGA CGA TTT CCC AAT GGG AAG 675
 E   E   A   R   C   K   S   L   G   R   F   P   N   G   K
GTA AAG GAG CCT CCA ATT CTC CGG GTT GGT GTA ACT GCA AAC TTT 720
 V   K   E   P   P   I   L   R   V   G   V   T   A   N   F
TTC TGT GAT GAA GGG TAT CGA CTG CAA GGC CCA CCT TCT AGT CGG 765
 F   C   D   E   G   Y   R   L   Q   G   P   P   S   S   R
TGT GTA ATT GCT GGA CAG GGA GTT GCT TGG ACC AAA ATG CCA GTA 810
 C   V   I   A   G   Q   G   V   A   W   T   K   M   P   V
TGT GAA GAA ATT TTT TGC CCA CTG CGG CCG CAG TCT AGA GAC AAA 855
 C   E   E   I   F   C   P   L   R   P   Q   S   R   D   K
ACT CAC ACA TGC CCA CCG TGC CCA GCA CCT GAA CTC CTG GGG GGA 900
 T   H   T   C   P   P   C   P   A   P   E   L   L   G   G
CCG TCA GTC TTC CTC TTC CCC CCA AAA CCC AAG GAC ACC CTC ATG 945
 P   S   V   F   L   F   P   P   K   P   K   D   T   L   M
ATC TCC CGG ACC CCT GAG GTC ACA TGC GTG GTG GTG GAC GTG AGC 990
 I   S   R   T   P   E   V   T   C   V   V   V   D   V   S
CAC GAA GAC CCT GAG GTC AAG TTC AAC TGG TAC GTG GAC GGC GTG 1035
 H   E   D   P   E   V   K   F   N   W   Y   V   D   G   V
GAG GTG CAT AAT GCC AAG ACA AAG CCG CGG GAG GAG CAG TAC AAC 1080
 E   V   H   N   A   K   T   K   P   R   E   E   Q   Y   N
AGC ACG TAC CGT GTG GTC AGC GTC CTC ACC GTC CTG CAC CAG GAC 1125
 S   T   Y   R   V   V   S   V   L   T   V   L   H   Q   D
TGG CTG AAT GGC AAG GAG TAC AAG TGC AAG GTC TCC AAC AAA GCC 1170
 W   L   N   G   K   E   Y   K   C   K   V   S   N   K   A
CTC CCA GTC CCC ATC GAG AAA ACC ATC TCC AAA GCC AAA GGG CAG 1215
 L   P   V   P   I   E   K   T   I   S   K   A   K   G   Q
CCC CGA GAA CCA CAG GTG TAC ACC CTG CCC CCA TCC CGG GAG GAG 1260
 P   R   E   P   Q   V   Y   T   L   P   P   S   R   E   E
ATG ACC AAG AAC CAG GTC AGC CTG ACC TGC CTG GTC AAA GGC TTC 1305
 M   T   K   N   Q   V   S   L   T   C   L   V   K   G   F
TAT CCC AGC GAC ATC GCC GTG GAG TGG GAG AGC AAT GGG CAG CCG 1350
 Y   P   S   D   I   A   V   E   W   E   S   N   G   Q   P
GAG AAC AAC TAC AAG ACC ACG CCT CCC GTG CTG GAC TCC GAC GGC 1395
 E   N   N   Y   K   T   T   P   P   V   L   D   S   D   G
TCC TTC TTC CTC TAT AGC AAG CTC ACC GTG GAC AAG AGC AGG TGG 1440
 S   F   F   L   Y   S   K   L   T   V   D   K   S   R   W
CAG CAG GGG AAC GTC TTC TCA TGC TCC GTG ATG CAT GAG GCT CTG 1485
 Q   Q   G   N   V   F   S   C   S   V   M   H   E   A   L
CAC AAC CAC TAC ACG CAG AAG AGC CTC TCC CTG TCC CCG GGT AAA 1530
 H   N   H   Y   T   Q   K   S   L   S   L   S   P   G   K
```

COMPLEMENT RECEPTOR 1 AND 2 FUSION PROTEINS

CROSS-REFERENCE TO RELATED APPLICATIONS

This application is a continuation of U.S. patent application Ser. No. 10/534,772, now U.S. Pat. No. 8,007,804, filed on Nov. 13, 2003 (Int'l), which is a U.S. National Phase of PCT International Application No. PCT/US2003/036459, filed on Nov. 13, 2003, which claims the benefit of U.S. Provisional Application No. 60/426,676, filed on Nov. 15, 2002, the contents of each of which are hereby incorporated herein by reference in their entirety.

I. BACKGROUND OF THE INVENTION

Complement is the collective term for a series of blood proteins and is a major effector mechanism of the immune system. Complement activation and its deposition on target structures can lead to direct complement-mediated cell lysis, or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bioincompatibility, e.g. post-cardiopulmonary inflammation and transplant rejection. Complement inhibition represents a potential therapeutic modality for the treatment of such immune-mediated diseases and disease states. Complement inhibitory proteins that systemically inhibit complement have been shown to be effective in various animal models of disease (and in a few clinical trials), but complement inhibitors that target a site of disease and complement activation offer significant potential advantages with regard to safety and efficacy.

In healthy individuals, complement deposition on host cell membranes is prevented by complement inhibitory proteins expressed at the cell surface. These complement inhibitory proteins are also expressed on the surface of tumor cells, often at increased levels, and are considered to be an important contributing factor to the resistance of tumor cells to monoclonal antibody-mediated immunotherapy (monoclonal antibodies that target to tumor cells and activate complement).

The complement system comprises a collection of about 30 proteins and is one of the major effector mechanisms of the immune system. The complement cascade is activated principally via either the classical (usually antibody-dependent) or alternative (usually antibody-independent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9)n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor; inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF) and membrane cofactor protein (MCP). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Crry is a widely distributed inhibitor of complement activation that functions similar to both DAF and MCP. Rodents also express DAF and MCP, although Crry appears to be functionally the most important regulator of complement activation in rodents. Although there is no homolog of Crry found in humans, the study of Crry and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Various types of complement inhibitory proteins are currently under investigation for therapy of inflammatory disease and disease states associated with bioincompatibility. Two of the best therapeutically characterized inhibitors of human complement are a soluble form of complement receptor 1 (sCR1) and an anti-O5 monoclonal antibody. These systemically active inhibitory proteins have shown efficacy in various animal models of disease and more recently in clinical trials (1-5, 6:#1037). Anti-O5 mAb inhibits the generation of C5a and the MAC, whereas sCR1 is an inhibitor of complement activation and also inhibits the generation of C3 activation products. Soluble forms of human decay accelerating factor (DAF) and membrane cofactor protein (MCP), membrane inhibitors of complement activation, have also been shown to be protective an animal models of inflammation and bioincompatability (7-11). CD59 is a membrane inhibitor of complement that blocks assembly of the MAC, but does not effect generation of complement opsonins or C3a and C5a. Soluble forms of CD59 have been produced, but its low functional activity in vitro, particularly in the presence of serum, indicates that sCD59 will have little or no therapeutic efficacy (12-15).

Targeting complement inhibitors to sites of complement activation and disease is likely to improve their efficacy. Since complement plays an important role in host defense and immune complex catabolism, targeted complement inhibitors can also reduce potentially serious side effects, particularly with long term complement inhibition. Recently, a modified form of sCR1 decorated with sialyl Lewis x (sLex) was prepared and shown to bind to endothelial cells expressing P and E selectin. sCR1 sLex was shown to be a more potent therapeutic than sCR1 in rodent models of inflammatory disease (16, 17). In in vitro feasibility studies, antibody-DAF (18) and antibody-CD59 (19) fusion proteins were shown to be more effective at protecting targeted cells than untargeted cells from complement. Non-specific membrane targeting of recombinant complement inhibitors has also been achieved by coupling inhibitors to membrane-inserting peptides (20, 21).

C3 activation fragments are abundant complement opsonins found at a site of complement activation, and they serve as ligands for various C3 receptors. One such receptor, complement receptor 2 (CR2), a transmembrane protein, plays an important role in humoral immunity by way of its expression predominantly on mature B cells and follicular dendritic cells (22, 23). CR2 is a member of the C3 binding protein family and consists of 15-16 short consensus repeat (SCR) domains, structural units that are characteristic of these proteins, with the C3 binding site being contained in the two N-terminal SCRs (24, 25). CR2 is not an inhibitor of complement and it does not bind C3b, unlike the inhibitors of complement activation (DAF, MCP, CR1 and Crry). Natural ligands for CR2 are iC3b, C3dg and C3d, cell-bound breakdown fragments of C3b that bind to the two N-terminal SCR domains of CR2 (26, 27). Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (ie. most host tissue). Even in absence of membrane bound complement regulators, substantial levels of iC3b are formed. iC3b is subsequently digested to the membrane bound fragments C3dg and then C3d by serum proteases, but this process is relatively slow (28, 29). Thus, the C3 ligands for CR2 are relatively long lived once they are generated and will be present in high concentrations at sites of complement activation.

II. SUMMARY OF THE INVENTION

In accordance with the purposes of this invention, as embodied and broadly described herein, this invention, in one aspect, relates to CR2 targeted modulators of complement activity.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows a diagram of examples of CR2-complement inhibitor fusion proteins.

FIG. 2 shows SDS-PAGE and Western blot analysis of purified recombinant fusion proteins and soluble complement inhibitors. Gels (10% acrylamide) were stained with coomasie blue. Western blots were developed using antibodies to complement inhibitors as the primary antibody.

FIG. 3 shows binding of recombinant fusion proteins to C3-opsonized CHO cells. Antibody sensitized CHO cells were incubated in C6-deficient serum, washed and incubated with soluble complement inhibitor (black trace), or fusion protein with CR2 at N-terminus (light gray trace) or C-terminus (dark gray trace) at 20 µg/ml. Cell binding of recombinant proteins was detected by flow cytometry using anti-DAF or anti-CD59 mAbs. Incubation of CHO cells with PBS instead of complement inhibitor gave similar fluorescence profile as sDAF and sCD59. Representative of 3 separate experiments.

FIG. 4 shows analysis of the interaction between CR2 fusion proteins and C3d by surface plasmon resonance. Solid lines indicate different concentrations of CR2 fusion proteins as indicated in FIG. _____. Broken lines show curves fitting to a 1:1 Langmuir binding model.

FIG. 5 shows inhibition of complement mediated lysis by recombinant sDAF and DAF fusion proteins. Antibody sensitized CHO cells (panel a) or sheep erythrocytes (panel b) were incubated with recombinant protein and 10% human serum (CHO cells) or 0.33% human serum (erythrocytes). These concentrations resulted in approximately 90% lysis of unprotected cells. Lysis was determined after 45 min. incubation at 37° C. Background lysis determined by incubating cells in heat inactivated serum was less than 5% and was subtracted. Mean+/−SD, n=4.

FIG. 6 shows inhibition of complement mediated lysis by recombinant sCD59 and CD59 fusion proteins. Antibody sensitized CHO cells (panel a) or sheep erythrocytes (panel b) were incubated with recombinant protein and 10% human. serum (CHO cells) or 0.33% human serum (erythrocytes). These concentrations resulted in approximately 90% lysis of unprotected cells. Lysis was determined after 45 min. incubation at 37° C. Background lysis determined by incubating cells in heat inactivated serum was less than 5% and was subtracted. Mean+/−SD, n=4.

FIG. 7 shows the effect of recombinant fusion proteins on U937 cell adhesion. Sheep erythrocytes were sensitized with IgM antibody and incubated in C6-deficient serum. C3 opsonized erythrocytes were coincubated with U937 cells in the presence of 500 nM recombinant fusion protein or PBS. Following incubation, the average number of U937 cells bound per erythrocyte was determined my microscopy. Mean+/−SD, n=3.

FIG. 8 shows the nucleotide and predicted amino acid sequence of mature human CR2-DAF. Amino acids underlined represent linking sequences between CR2 and DAF.

FIG. 9 shows the nucleotide and predicted amino acid sequence of mature human CR2-CD59. Amino acids underlined represent linking sequences between CR2 and CD59.

Figure 10:
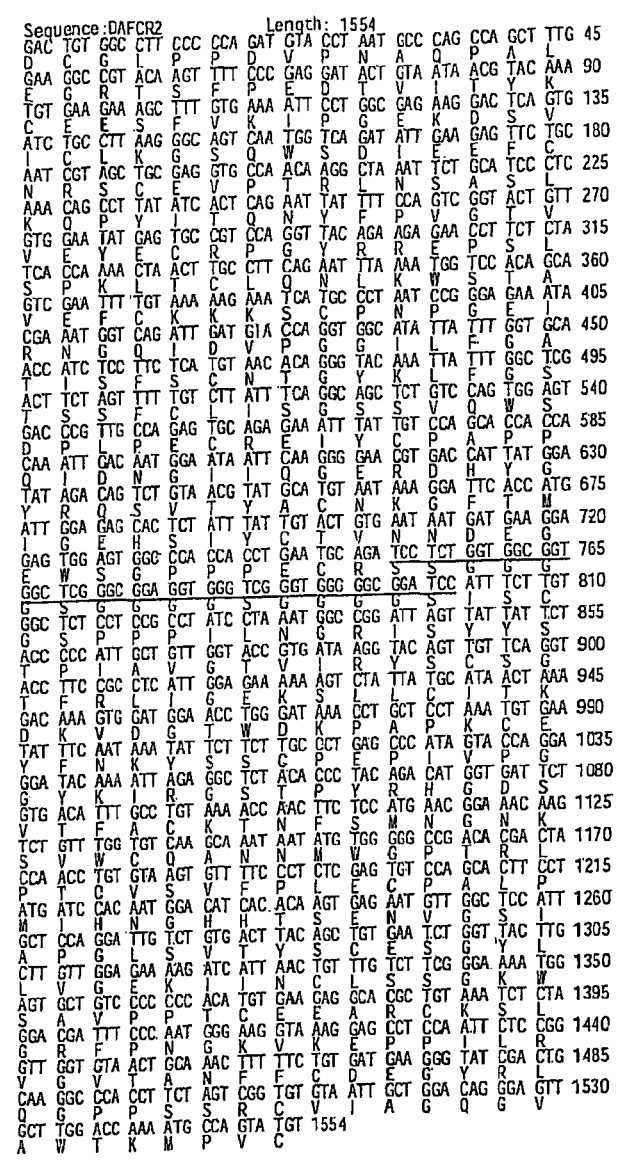

FIG. 10 shows the nucleotide and predicted amino acid sequence of mature human DAF-CR2. Amino acids underlined represent linking sequences between DAF and CR2.

FIG. 11 shows the nucleotide and predicted amino acid sequence of mature human CD59-CR2. Amino acids underlined represent linking sequences between CD59 and CR2.

Figure 12:
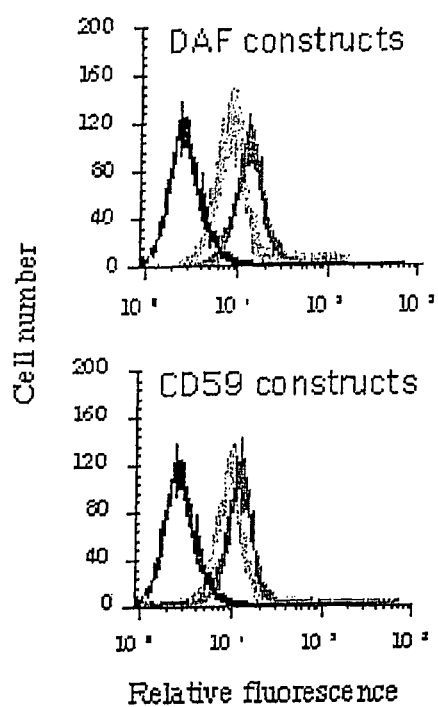

FIG. 12 shows targeting of CR2 containing fusion proteins to C3-coated CHO cells. C3 ligand was generated on CHO cells by incubation of cells in 10% anti-CHO antiserum and 10% C6-depleted human serum (to prevent formation of membrane attack complex and cell lysis). Cells were washed and incubated with fusion protein (20 ug/ml, 4° C., 30 min). Binding was detected by flow cytometric analysis using antibodies against appropriate complement inhibitor (DAF or CD59). Black line: control (no fusion protein); Light gray: CR2 at C-terminus; Dark gray: CR2 at N-terminus.

Figure 13:
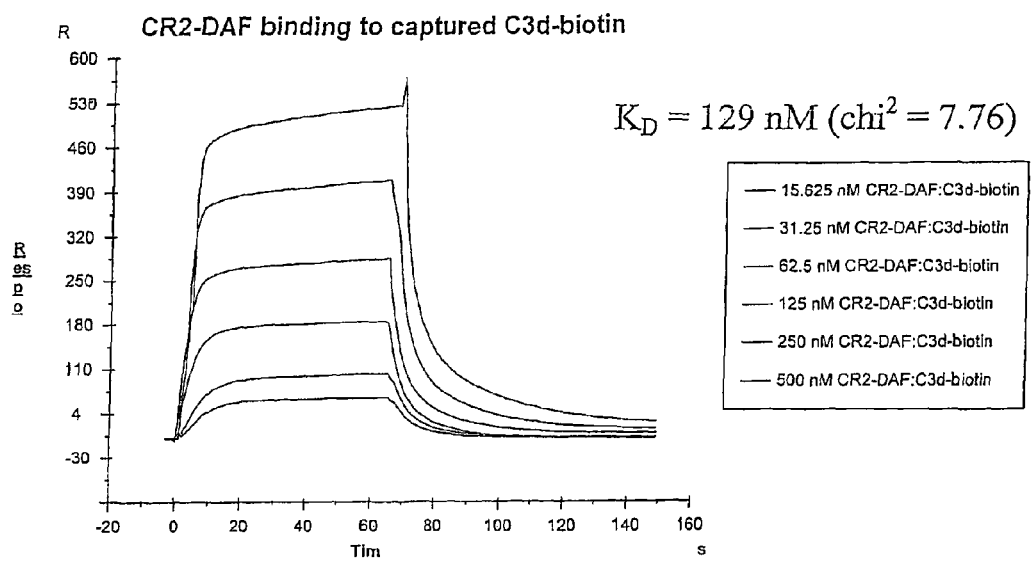

FIG. 13 shows analysis of CR2-DAF binding to C3dg by surface plasmon resonance.

Figure 14:
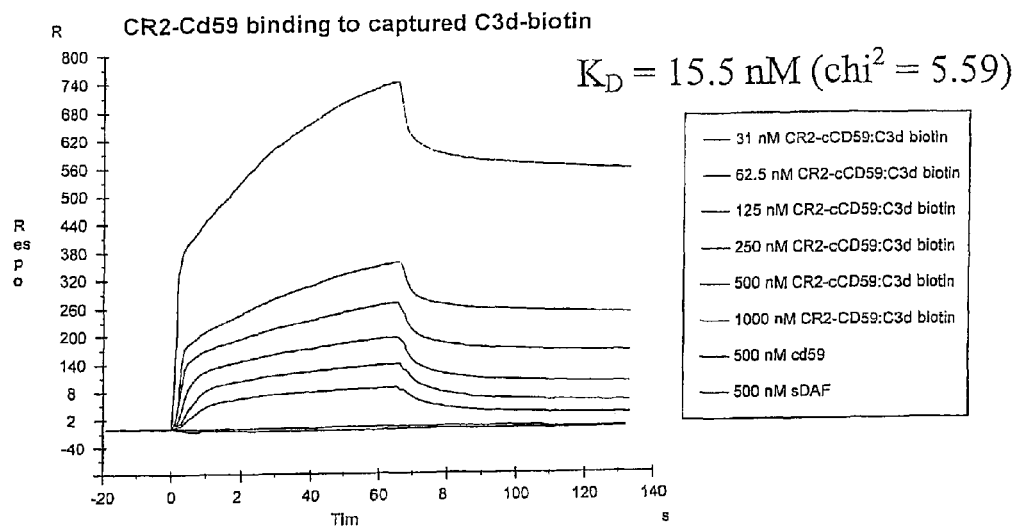

FIG. 14 shows analysis of CR2-CD59 binding to C3dg by surface plasmon resonance.

Figure 15:
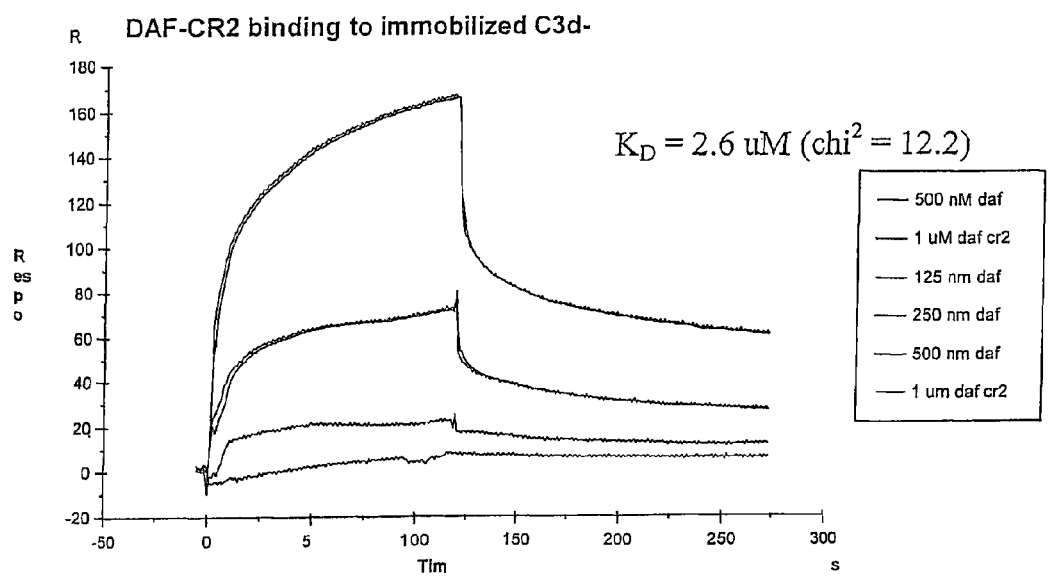

FIG. 15 shows analysis of DAF-CR2 binding to C3dg by surface plasmon resonance.

Figure 16:
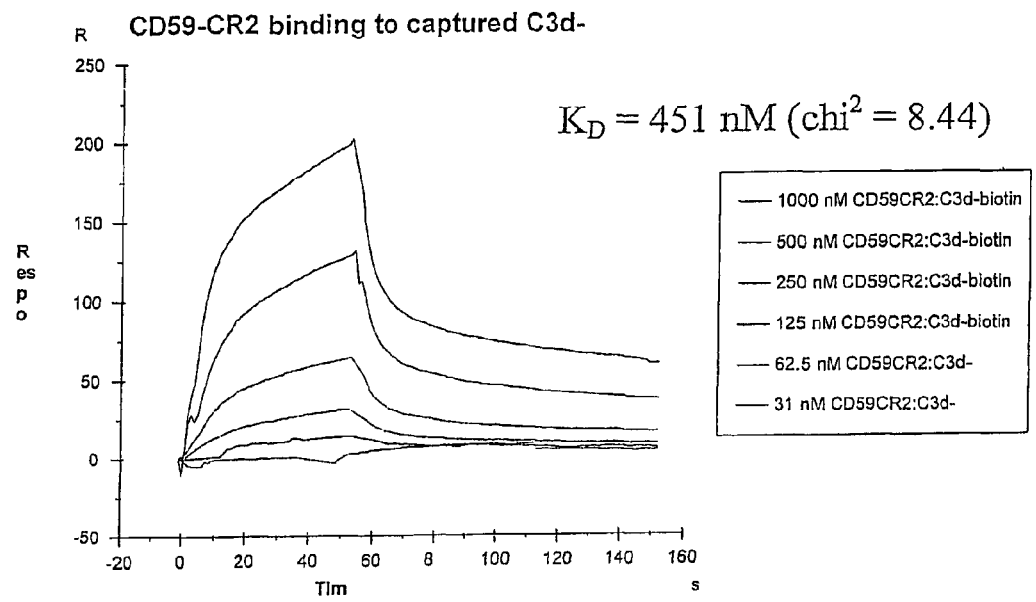

FIG. 16 shows analysis of CD59-CR2 binding to C3dg by surface plasmon resonance.

Figure 17:
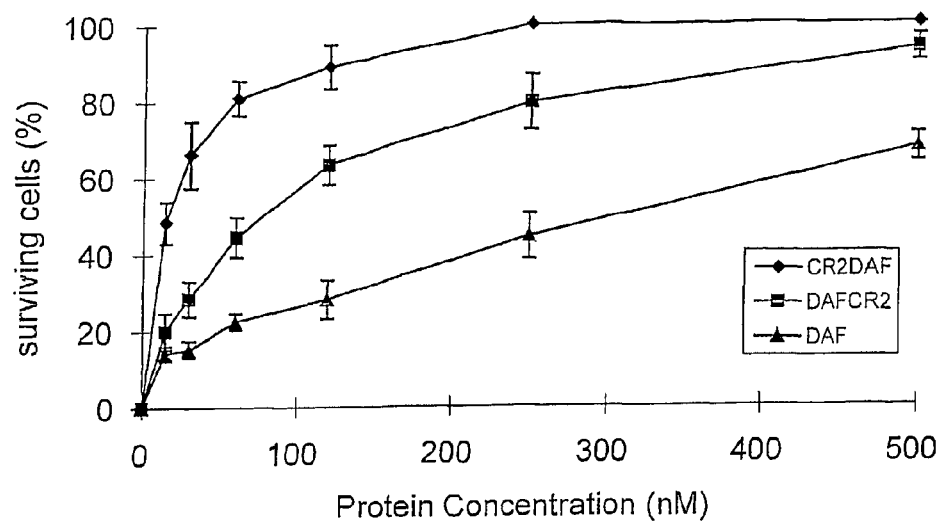

FIG. 17 shows the effect of targeted and untargeted DAF on complement-mediated lysis of CHO cells. CHO cells were sensitized to complement with anti-CHO antisera (10% concentration, 4° C., 30 min) and subsequently incubated with 10% normal human serum (NHS) (37° C., 60 min) in the presence of varying concentrations, of complement inhibitory proteins. Cell lysis was then determined by trypan blue exclusion assay. Representative experiment showing mean+/−SD (n=3). Three separate experiments using different fusion protein preparations performed.

Figure 18:
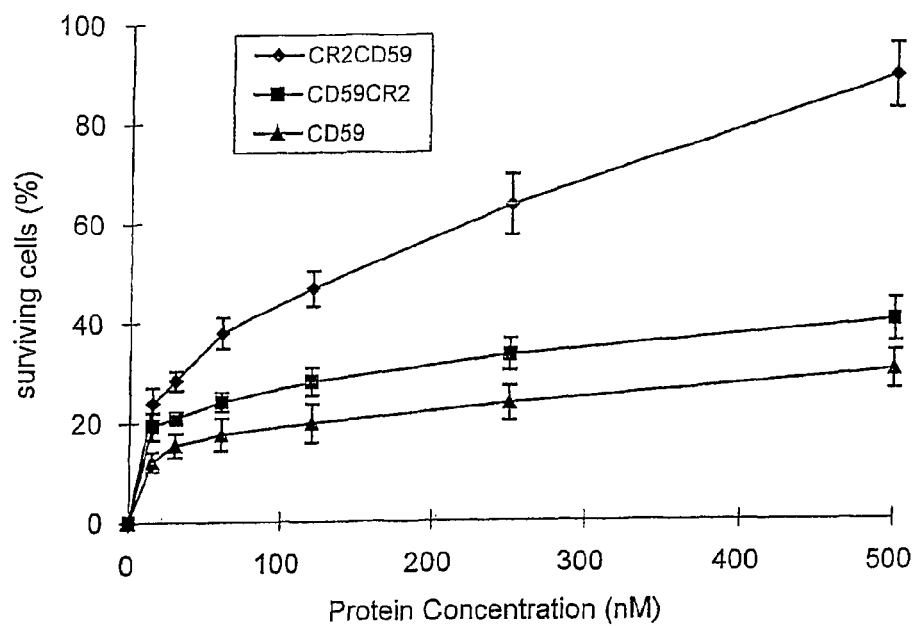

FIG. 18 shows the effect of targeted and untargeted CD59 on complement-mediated lysis of CHO cells. Assay performed as described in legend to FIG. 17. Representative experiment showing mean+/−SD (n=3). Three separate experiments using different fusion protein preparations performed.

Figure 19:
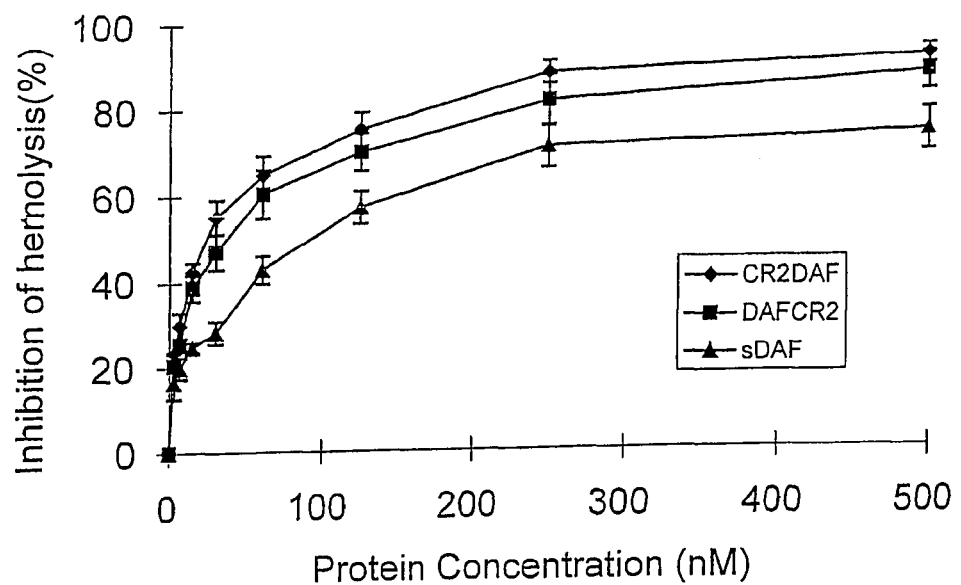

FIG. 19 shows the effect of targeted and untargeted DAF on complement-mediated hemolysis. Sheep erythrocytes (E) were sensitized with anti-sheep E antibody and subsequently incubated with a 1/300 dilution of NHS (37° C., 60 min) in the presence of varying concentrations of complement inhibitory proteins. Cell lysis was determined by measuring released hemoglobin (absorbance at 412 nm). Representative experiment showing mean+/−SD (n=3). Two separate experiments using different fusion protein preparations performed.

Figure 20:
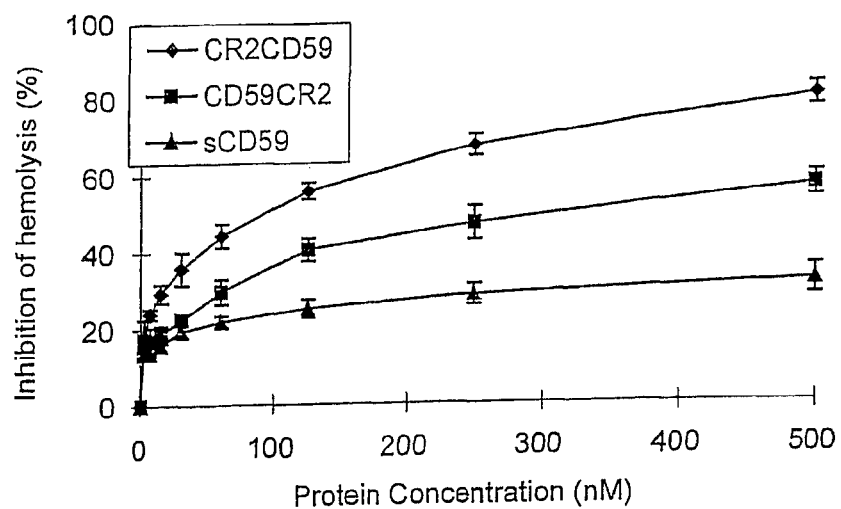

FIG. 20 shows the effect of targeted and untargeted CD59 on complement-mediated hemolysis. Assay performed as described in legend to FIG. 19. Representative experiment showing mean+/−SD (n=3). Two separate experiments using different fusion protein preparations performed.

FIG. 21 shows the nucleotide and predicted amino acid sequence of mature human CR2-human IgG1 Fc. Amino acids underlined represent linking sequences between CR2 and Fc region. Expression plasmid contains genomic Fc region (hinge-intron-CH2-intron-CH3).

Figure 22:
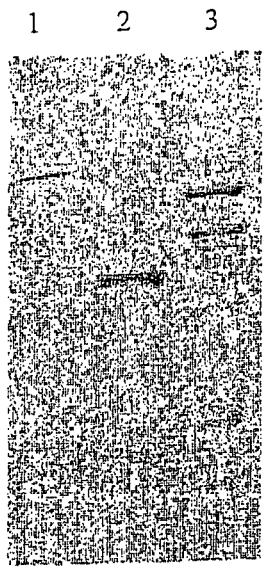

FIG. 22 shows SDS-PAGE analysis of CR2-Fc fusion protein. Purified CR2-Fc was run under nonreducing (lane 1) or reducing (lane 2) conditions. Gel stained by coomassie blue. (for MW of markers in lane 3, see FIG. 2).

Figure 23:
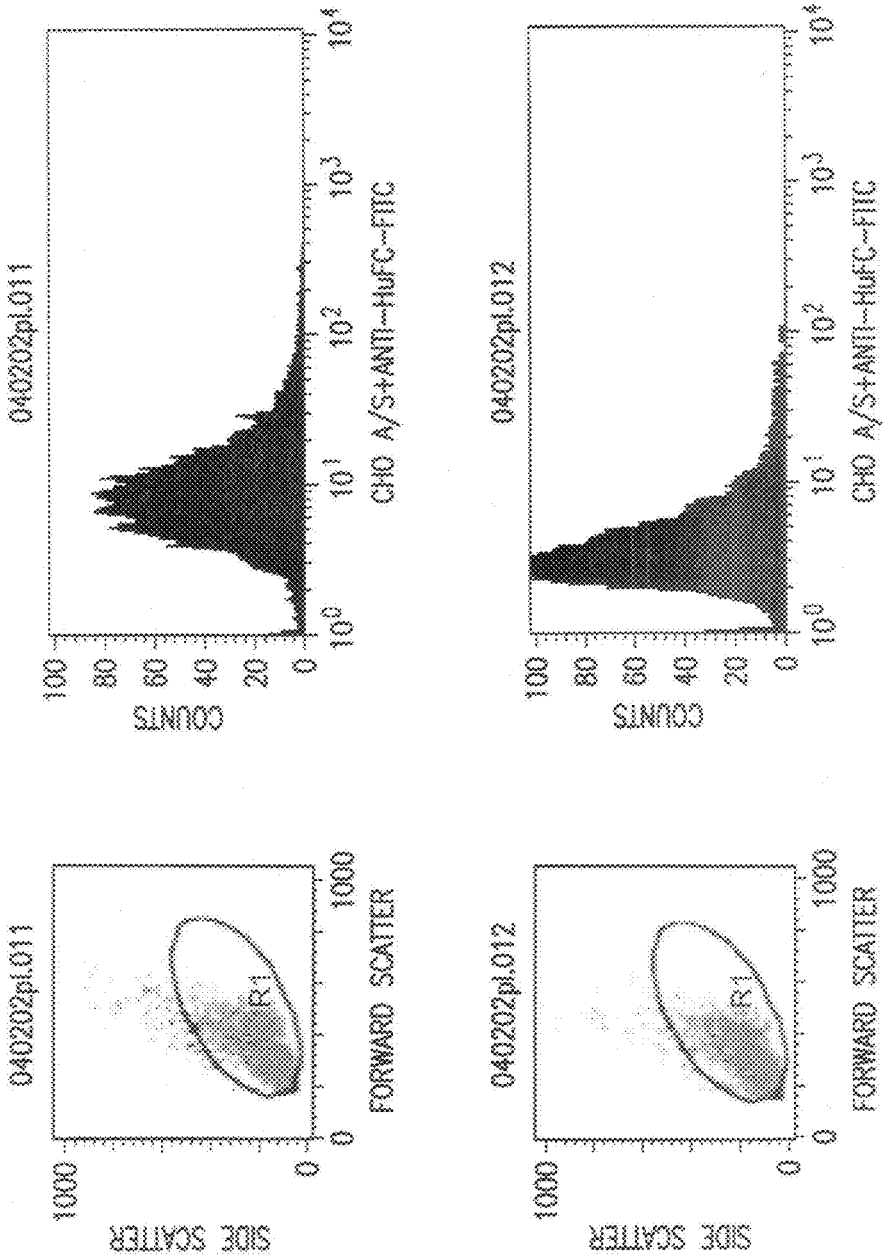

FIG. 23 shows targeting of CR2-Fc to C3-coated CHO cells. C3 ligand was generated as described (legend to FIG. 12). Cells were washed and incubated with CR2-Fc (20 ug/ml, 4° C., 30 min). Binding was detected by flow cytometric analysis using antibodies against human Fc conjugated to FITC. Upper panel shows results from incubation of CR2-Fc with C3-coated CHO cells, and lower panel shows results from incubation of CR2-Fc with control CHO cells.

Figure 24:
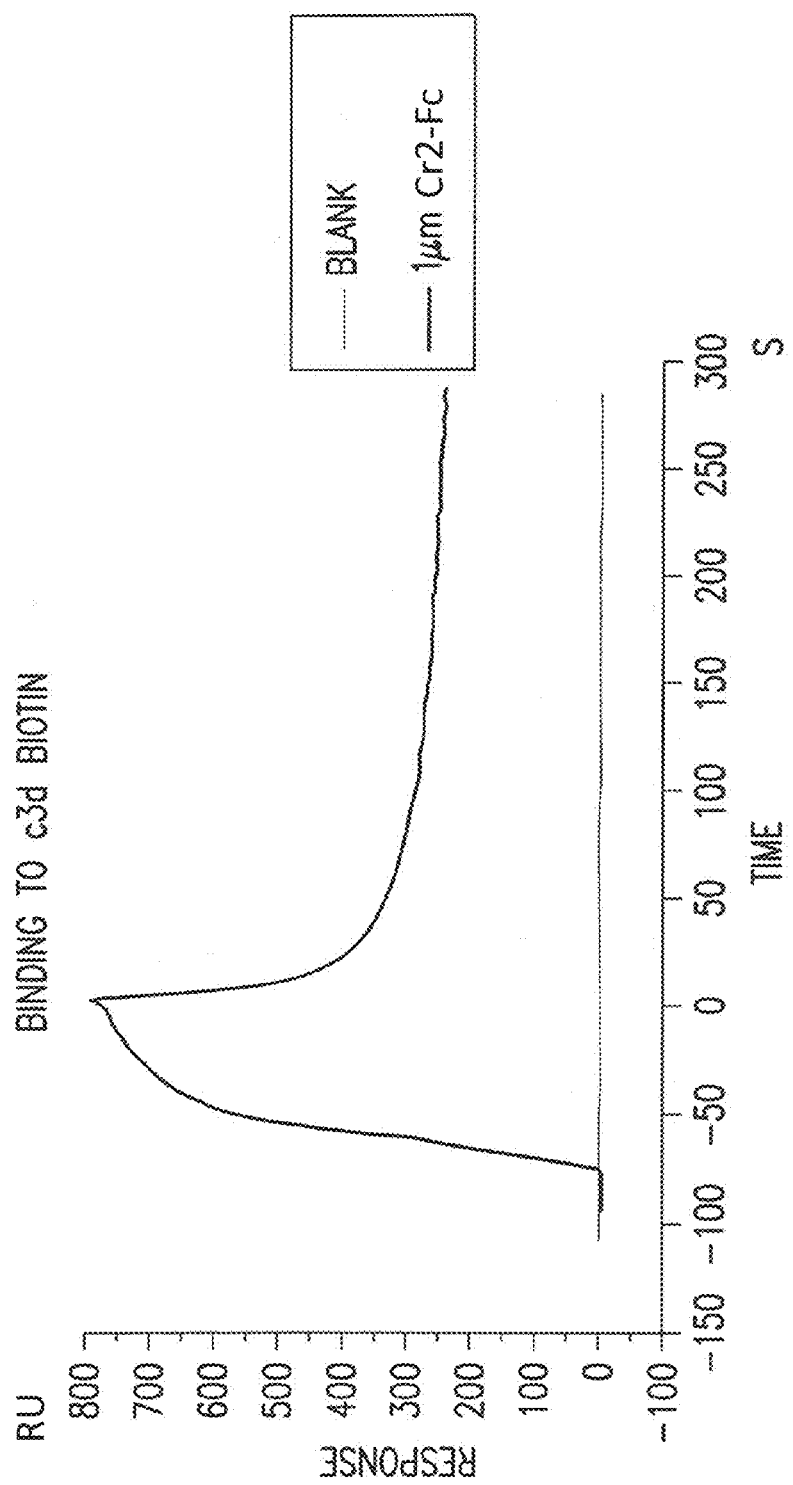

FIG. 24 shows surface plasmon resonance sensorgram showing binding of CR2-Fc to C3d ligand immobilized on chip.

Figure 25:
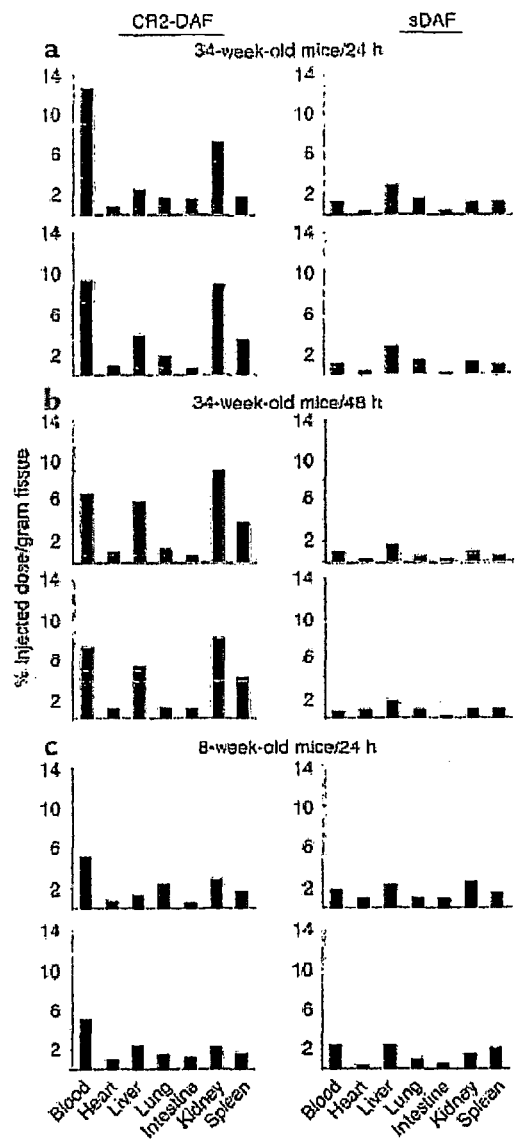

FIG. 25 shows the biodistribution of $^{125}$I-CR2-DAF and $^{125}$I-sDAF in 34 week old NZB/W F1 mice. Radiolabeled proteins were injected into the tail vein and biodistribution of radiolabel determined after 24 hr. Each protein was injected into 2 mice.

Figure 26:
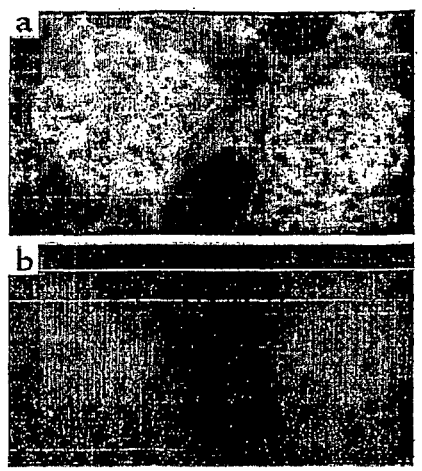

FIG. 26 shows imaging of CR2-DAF bound to glomeruli of 24-week-old MRL/lpr mice. Glomerular binding of CD2-DAF (a) and sDAF (b) was analyzed 24 hours after tail-vein injection of each protein. The figure shows immunofluorescence staining of kidney sections.

Figure 27:
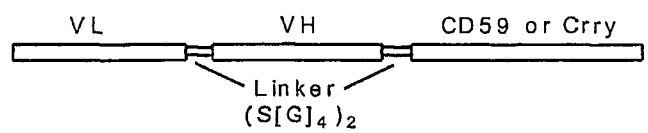

FIG. 27 shows the single chain antibody CD59-Cry construct. The figure shows the construct comprises a variable light chain (VL) and a variable heavy chain (VH) from K9/9 mAb. The construct was prepared in the yeast expression vector pPICZalph (Invitrogen).

Figure 28:
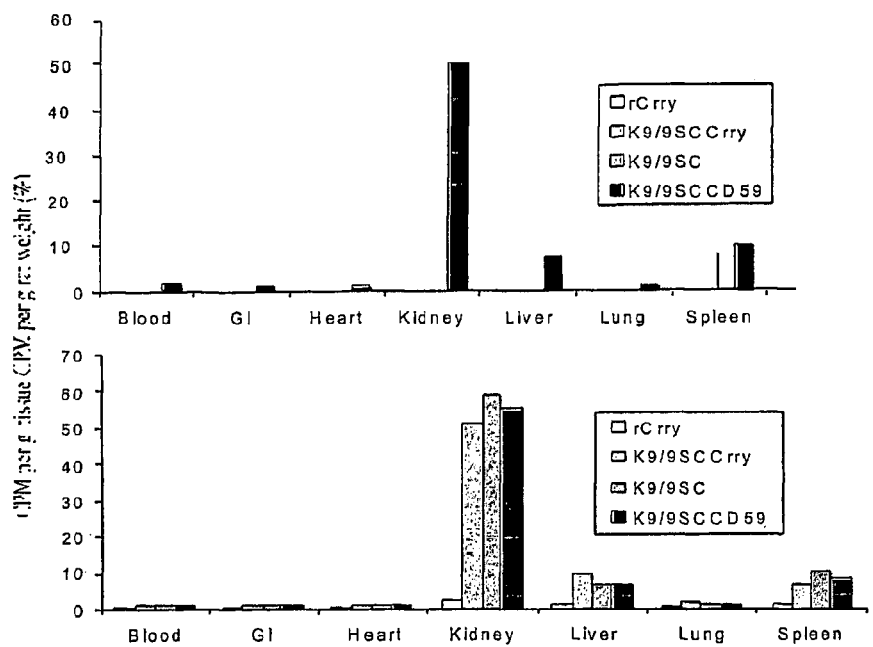

FIG. 28 shows the biodistribution of complement inhibitors and K9/9 single chain Ab in rats. Iodinated recombinant proteins administered 4 days after PAN treatment and radioactivity in organs measured 48 hr later.

Figure 29:
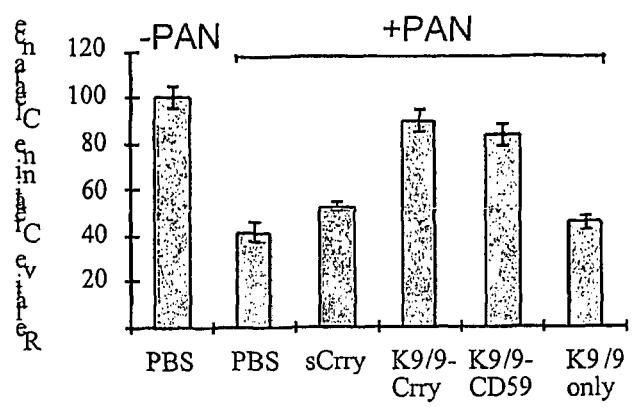

FIG. 29 shows Creatinine clearance in rats treated with PAN and receiving indicated therapy (n=4, +/−SD).

Figure 30:
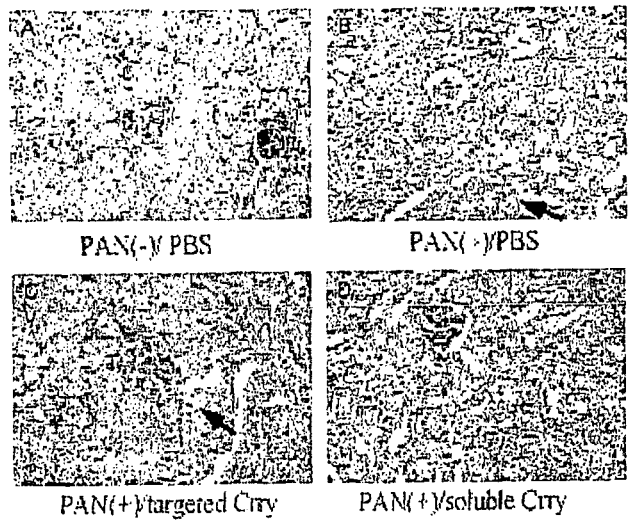

FIG. 30 shows PAS stained renal cortex. FIG. 30A shows No PAN control, FIG. 30B: PAN with PBS treatment, FIG. 30C: PAN with targeted K9/9 Crry treatment, and FIG. 30D: PAN with sCrry treatment.

Figure 31:
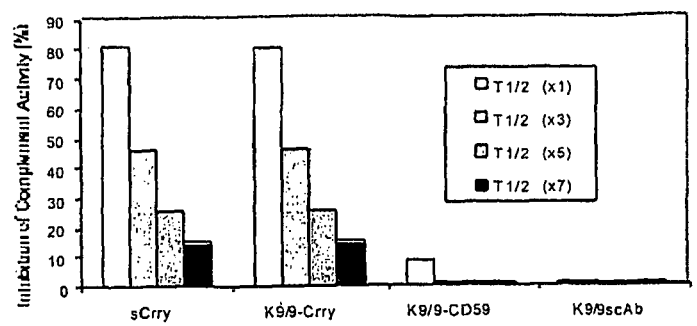

FIG. 31 shows complement inhibitory activity in serum after administration of recombinant proteins. Measured by lysis of sensitized sheep erythrocytes. Percent inhibitory activity shown relative to serum from control rats.

IV. DETAILED DESCRIPTION

The present invention can be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such can, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Treatment" or "treating" means to administer a composition to a subject with a condition, wherein the condition can be any pathogenic disease, autoimmune disease, cancer or inflammatory condition. The effect of the administration of the composition to the subject can have the effect of but is not limited to reducing the symptoms of the condition, a reduction in the severity of the condition, or the complete ablation of the condition.

Herein, "inhibition" or "inhibits" means to reduce activity. It is understood that inhibition can mean a slight reduction in activity to the complete ablation of all activity. An "inhibitor" can be anything that reduces activity.

Herein, "activation" or "activates" means to increase activity. It is understood that activation can mean an increase in existing activity as well as the induction of new activity. An "activator" can be anything that increases activity.

B. Complement Inhibiting and Activating Constructs

Disclosed are compositions comprising a construct, wherein the construct comprises CR2 and a modulator of complement activity.

CR2 consists of an extracellular portion consisting of 15 or 16 repeating units known as short consensus repeats (SCRs). Amino acids 1-20 comprise the leader peptide, amino acids 23-82 comprise SCR1, amino acids 91-146 comprise SCR2, amino acids 154-210 comprise SCR3, amino acids 215-271 comprise SCR4. The active site (C3dg binding site) is located in SCR 1-2 (the first 2 N-terminal SCRs). SCR units are separated by short sequences of variable length that serve as spacers. It is understood that any number of SCRs containing the active site can be used. In one embodiment, the construct contains the 4 N-terminal SCR units. In another embodiment, the construct includes the first two N-terminal SCRs. In another embodiment the construct includes the first three N-terminal SCRs.

It is understood that species and strain variation exist for the disclosed peptides, polypeptides, proteins, protein fragments and compositions. Specifically disclosed are all species and strain variations for the disclosed peptides, polypeptides, proteins, protein fragments and compositions.

Also disclosed are compositions, wherein the construct is a fusion protein

Herein a "fusion protein" means two or more components comprising peptides, polypeptides, or proteins operably linked. CR2 can be linked to complement inhibitors or activators by an amino acid linking sequence. Examples of linkers are well known in the art. Examples of linkers can include but are not limited to (Gly$_4$Ser)$_3$ (G4S), (Gly$_3$Ser)$_4$ (G3S), SerGly$_4$, and SerGly$_4$SerGly$_4$. Linking sequences can also consist of "natural" linking sequences found between SCR units within human (or mouse) proteins, for example VSVFPLE, the linking sequence between SCR 2 and 3 of human CR2. Fusion proteins can also be constructed without linking sequences.

Also disclosed are compositions of the invention, wherein the fusion protein inhibits complement.

Also disclosed are compositions of the invention, wherein the modulator of complement activity comprises a complement inhibitor.

Also disclosed are compositions of the invention; for example, wherein the complement inhibitor is decay accelerating factor (DAF) SEQ ID NO: 1 (nucleotide) and SEQ ID NO: 2 (amino acid). For example, the DAF can be soluble human DAF comprising the four SCR domains without glycophosphatidyl anchor and serine-threonine rich region. The DAF can also be soluble human DAF comprising the four SCR domains and the serine-threonine rich region but without glycophosphatidyl anchor.

The DAF extracellular region consists of 4 SCR units at N-terminus followed by serine/threonine rich region. Amino acids 1-34 comprise the leader peptide, amino acids 35-95 comprise SCR1, amino acids 97-159 comprise SCR2, amino acids 162-221 comprise SCR3, amino acids 224-284 comprise SCR4, and amino acids 287-356 comprise the S/T region. In one embodiment of the invention, the composition of the invention comprises all 4 SCR units. In another embodiment of the invention, the composition comprises SCR2-4 of DAF.

Disclosed are compositions of the invention, wherein the complement inhibitor comprises a fusion protein between CD59 and another complement inhibitor selected from the group consisting of DAF, MCP, Crry and CR1. Also disclosed are compositions of the invention, wherein the complement inhibitor is a fusion protein of two or more complement inhibitors.

Also disclosed are compositions of the invention, wherein the fusion protein comprises CR2-DAF (SEQ ID NO: 6). Also disclosed are compositions of the invention wherein the fusion protein is encoded by a nucleotide comprising SEQ ID NO: 5.

Also disclosed are compositions of the invention, wherein the fusion protein comprises DAF-CR2 (SEQ ID NO: 10). Also disclosed are compositions of the invention wherein the fusion protein is encoded by a nucleotide comprising SEQ ID NO: 9.

Also disclosed are compositions of the invention, wherein the complement inhibitor is human CD59 (SEQ ID NO: 3 (nucleotide) and SEQ ID NO: 4 (amino acid)). The human CD59 can be soluble human CD59 comprising the mature protein without glycophosphatidyl anchor.

Also disclosed are compositions of the invention, wherein the fusion protein comprises CR2-human CD59 (SEQ ID NO: 8). Also disclosed are compositions of the invention wherein the fusion protein is encoded by a nucleotide comprising SEQ ID NO: 7.

Also disclosed are compositions of the invention, wherein the fusion protein comprises human CD59-CR2 (SEQ ID NO: 12). Also disclosed are compositions of the invention wherein the fusion protein is encoded by a nucleotide comprising SEQ ID NO: 10.

Also disclosed are compositions of the invention wherein the complement inhibitor is an antibody to C5. Also disclosed are compositions of the invention, wherein the fusion protein comprises CR2-anti-05 antibody.

Also disclosed are compositions of the invention, wherein the complement inhibitor is CR1 (SEQ ID NO: 13 (nucleotide) and SEQ ID NO: 14 (amino acid)). The extracellular region of CR1 can comprise 30 SCR units. It is an embodiment of the invention that the composition can comprise the entire extracellular region of CR1. In another embodiment of the invention, the composition comprises [the] one active site[s] of CR1. The active sites of CR1 are amino acids 1-46 which comprise the leader peptide, amino acids 47-300 which comprise SCR1-4 (C4b binding site, lower affinity for C3b), amino acids 497-750 which comprise SCR8-11 (C3b binding site, lower affinity for C4b), amino acids 947-1200 which comprise SCR15-18 (C3b binding site, lower affinity for C4b), and amino acids 1400-1851 which comprise the C1q binding site. In an additional embodiment of the invention, the composition of the invention can comprise any [one or] combination or all of the active sites of CR1.

Also disclosed are compositions of the invention, wherein the complement inhibitor comprises the active sites of CR1, and wherein [the] one active site[s] further comprise a leader peptide comprising amino acids 6-46, amino acids 47-300 which comprise SCR1-4 (C4b binding site, lower affinity for C3b), amino acids 497-750 which comprise SCR8-11 (C3b binding site, lower affinity for C4b), amino acids 947-1200 which comprise SCR15-18 (C3b binding site, lower affinity for C4b), and amino acids 1400-1851 which comprise the C1q binding site. In an additional embodiment of the invention, the composition of the invention can comprise any [one or] combination or all of the active sites of CR1.

Also disclosed are compositions of the invention, wherein the complement inhibitor is MCP (SEQ ID NO: 15 (nucleotide) and SEQ ID NO: 16 (amino acid)). The extracellular region consists of 4 SCR units followed by ser/thr region. Amino acids 1-34 comprise the leader peptide, amino acids 35-95 comprise SCR1, amino acids 96-158 comprise SCR2, amino acids, 159-224 comprise SCR3, amino acids 225-285 comprise SCR4, and amino'acids 286-314 comprise the S/T region.

Also disclosed are compositions of the invention, wherein the complement inhibitor is Crry (SEQ ID NO: 17). The Crry can be soluble mouse Crry comprising the 5 N-terminal SCR domains without transmembrane region.

Also disclosed are compositions of the invention, wherein the complement inhibitor is murine CD59. The murine CD59 can be soluble murine CD59 comprising the mature protein without glycophosphatidyl anchor.

Disclosed are compositions of the invention, wherein the fusion protein activates complement.

Thus, disclosed are compositions of the invention, wherein the modulator of complement activity comprises a complement activator.

Disclosed are compositions of the invention, wherein the complement activator is human IgG1 Fc (SEQ ID NO: 18).

Also disclosed are compositions of the invention, wherein the complement activator comprises CR2-human IgG1 Fc (SEQ ID NO: 20). Also disclosed are compositions of the invention wherein the fusion protein is encoded by a nucleotide comprising SEQ ID NO: 21.

Disclosed are compositions of the invention, wherein the fusion protein is human IgM (SEQ ID NO: 19).

Also disclosed are compositions of the invention, wherein the fusion protein comprises CR2-human IgM Fc.

Disclosed are compositions of the invention, wherein the complement activator is mouse IgG3 (SEQ ID NO: 22).

Also disclosed are compositions of the invention, wherein the fusion protein comprises CR2-murine IgG3 Fc.

Also disclosed are compositions of the invention, wherein the fusion protein comprises CR2-murine IgM Fe.

It is specifically contemplated that complement activator can also increase antibody-dependent cell-mediated cytotoxicity (ADCC) via the Fc portion of the composition. ADCC is the destruction of a target cell by a natural killer (NK) cell via recognition of and contact with an Fc region and an Fc receptor on the NK cell. This can be in the form of FcγRIII recognition of IgG1 Fc or IgG3 Fc. Following the contact of the Fc receptor with the Fc, the NK cell lysis the target cell via the use of perforin and granzyme. This mechanism can be important in controlling tumor growth Disclosed are compositions of the invention, wherein the CR2-Fc fusion protein is not immunogenic. It is understood that a composition that is not immunogenic (ie. does not elicit an immune response) is less likely to be attacked and inactivated by the subjects own immune response. The anticipated lack of CR2-Fc immunogenicity is a potential advantage over anti-C3d antibodies, even if antibodies are humanized. It is an embodiment of the invention that the Fc region fused to CR2 can be from any human or mouse IgG isotype, human or mouse IgM, or any human or mouse IgG isotype containing a mu-tailpiece. The mu-tailpiece is an 18 amino acid C-terminal region from IgM that, when added C-terminal to IgG Fc sequences, results in the generation of polymeric forms of IgG (similar to IgM) that efficiently activate complement and have enhanced affinity for Fc receptors. The fusion can occur at the hinge region of the Fc portion of the composition.

CR2 fusion proteins containing either IgM or IgG Fc regions with a mu-tailpiece can have advantages over CR2-IgG Fc fusion proteins. IgM or IgG-mu Fc regions will result in polymeric fusion proteins with up to 6 Fcs and 12 CR2 sites. These constructs can have enhanced avidity for C3 ligand and enhanced effector function (complement activation and Fc receptor binding).

Also disclosed are compositions of the invention, wherein the complement activator is CVF (SEQ ID NO: 23 (nucleotide) and SEQ ID NO: 24 (amino acid)).

In one embodiment of the invention, CVF can be coupled to soluble CR2. It is understood that CVF binds factor B and activates the alternative pathway of complement by forming CVFBb, a C3/C5 convertase that is not inactivated by complement inhibitory proteins. The half life of CVFBb is about 7 hr. compared to about 1 min. for the physiological alternative pathway convertase, C3bBb.

It is an embodiment of the invention that CVF can be chemically coupled to soluble CR2.

Disclosed are compositions of the invention, wherein the construct is in a vector.

Disclosed are cells comprising the vector of the invention.

Also disclosed are compositions, wherein the construct is an immunoconjugate. Herein "immunoconjugate" means two or more components comprising peptides, polypeptides, or proteins operably linked by a chemical cross-linker. Linking of the components of the immunoconjugate can occur on reactive groups located on the component. Reactive groups that can be targeted using a cross-linker include primary amines, sulfhydryls, carbonyls, carbohydrates and carboxylic acids, or active groups can be added to proteins. Examples of chemical linkers are well known in the art and can include but are not limited to bismaleimidohexane, m-maleimidobenzoyl-N-hydroxysuccinimide ester, NHS-Esters-Maleimide Crosslinkers such as MBS, Sulfo-MBS, SMPB, Sulfo-SMPB, GMBS, Sulfo-GMBS, EMCS, Sulfo-EMCS; Imidoester Cross-linkers such as DMA, DMP, DMS, DTBP; EDC [1-Ethyl-3-(3-Dimethylaminopropyl)carbodiimide Hydrochloride], [2-(4-Hydroxyphenyl)ethyl]-4-N-maleimidomethyl)-cyclohexane-1-carboxamide, DTME: Dithio-bis-maleimidoethane, DMA (Dimethyl adipimidate.2HCl), DMP (Dimethyl pimelimidate.2HCl), DMS (Dimethyl suberimidate.2HCl), DTBP (Dimethyl 3,3'-dithiobispropionimidate.2HCl), MBS, (m-Maleimidobenzoyl-N-hydroxysuccinimide ester), Sulfo-MBS (m-Maleimidobenzoyl-N-hydroxysuccinimide ester), Sulfo-SMPB (Sulfosuccinimidyl 4-[p-maleimidophenyl]butyrate(, GMBS (N-[.-maleimidobutyryloxy]succinimide ester), EMCS(N-[.-maleimidocaproyloxy]succinimide ester), and Sulfo-EMCS (N-[.-maleimidocaproyloxy]sulfosuccinimide ester).

C. Methods of Using the Compositions

Various types of complement inhibitory proteins are currently under investigation for therapy of inflammatory disease and disease states associated with bioincompatibility. Two of the best therapeutically characterized inhibitors of human complement are a soluble form of complement receptor I (sCR1) and an anti-C5 monoclonal antibody. These systemically active inhibitory proteins have shown efficacy in various animal models of disease and more recently in clinical trials (1-5, 6:#1037 which are incorporated herein by reference regarding teachings on in vivo efficacy and clinical results).

Disclosed are methods of treating a condition affected by complement in a subject comprising administering to the subject the composition of the invention. It is understood that administration of the composition to the subject can have the effect of, but is not limited to, reducing the symptoms of the condition, a reduction in the severity of the condition, or the complete ablation of the condition.

1. Methods of Using the Compositions to Inhibit Complement

Disclosed are methods of treating a condition affected by complement in a subject comprising administering to the subject the composition of the invention, wherein the composition will inhibit complement activity. It is understood that the effect of the administration of the composition to the subject can have the effect of but is not limited to reducing the symptoms of the condition, a reduction in the severity of the condition, or the complete ablation of the condition.

Disclosed are methods of reducing complement-mediated damage comprising administering to a subject the composition of the invention, which inhibits complement.

Disclosed are methods of the invention, wherein the condition treated is an inflammatory condition. Also disclosed are methods of the invention, wherein the inflammatory condition can be selected from the group consisting of asthma, systemic lupus erythematosus, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial infarction, alzheimer's disease, transplant rejection (allogeneic and xenogeneic), thermal trauma, any immune complex-induced inflammation, glomerulonephritis, myasthenia gravis, cerebral lupus, Guillain-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bullous pemphigoid, stroke, atherosclerosis, and scleroderma.

Also disclosed are methods of the invention, wherein the condition is a viral infection. Also disclosed are methods of the invention, wherein the viral infection can be selected from the list of viruses consisting of Influenza virus A, Influenza virus B, Respiratory syncytial virus, Dengue virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Hantavirus.

Disclosed are methods of the invention, wherein the condition is an inflammatory response to a viral vector. The viral vector can be selected from the list of viruses consisting of adenovirus, vaccinia virus, adeno associated virus, modified vaccinia ancara virus, and cytomegliavirus. It is understood that other viral vectors are in use for vaccine delivery. Specifically disclosed are each and every viral vector known in the art.

It is understood in the art that *Candida* express a CR3 like protein that has similar binding properties as CR2. The CR3 like protein appears to be involved in pathogenesis. Therefore, an embodiment of the invention is treating a subject with a fungal infection, wherein the treatment blocks fungal-"CR3" function as well as inhibits complement, comprising administering to a subject the composition of the invention.

Disclosed are methods of the invention, wherein complement inhibitor can enhance the outcome of apoptosis-base therapy (e.g., gene therapy with adenovirus expressing Fas ligand).

Apoptosis occurring during normal development is non inflammatory and is involved in induction of immunological tolerance. Although apoptotic cell death can be inflammatory depending on how it is activated and in what cell types (for example, therapeutic agents that ligate Fas are able to induce inflammation), necrotic cell death results in a sustained and powerful inflammatory response mediated by released cell contents and by proinflammatory cytokines released by stimulated phagocytes. Apoptotic cells and vesicles are normally cleared by phagocytes, thus preventing the pro-inflammatory consequences of cell lysis. In this context, it has been shown that apoptotic cells and apoptotic bodies directly fix complement, and that complement can sustain an anti-inflammatory response due to opsonization and enhanced phagocytosis of apoptotic cells.

Inflammation is involved in non specific recruitment of immune cells that can influence innate and adaptive immune responses. Modulating complement activation during apoptosis-based tumor therapy to inhibit phagocytic uptake of apoptotic cells/bodies enhances the inflammatory/innate immune response within the tumor environment. In addition, apoptotic cells can be a source of immunogenic self antigens and uncleared apoptotic bodies can result in autoimmunization. In addition to creating an enhanced immuno-stimulatory environment, modulating complement at a site in which tumor cells have been induced to undergo apoptosis further augments or triggers specific immunity against a tumor to which the host is normally tolerant.

The disclosed compositions of the invention can act as CR2 and CR3 antagonists. Disclosed are methods of inhibiting complement activity via inhibition of CR2 comprising administering the composition of the invention to a subject. Also disclosed are methods of inhibiting complement activity via inhibition of CR3 comprising administering the composition of the invention to a subject. As a CR2 antagonist can modulate immune response, a CR3 antagonist can have second anti-inflammatory mechanism of action since CR3 is integrin that binds endothelial ICAM1. ICAM1 is expressed at sites of inflammation and is involved in leukocyte adhesion and diapedesis. In addition, ICAM1 expression is upregulated by complement activation products.

2. Methods of Using the Compositions to Activate Complement

Disclosed are methods of treating a condition affected by complement in a subject comprising administering to the subject the composition of the invention, wherein the composition will activate complement. It is understood that the administration of the composition to the subject can have the effect of, but is not limited to, reducing the symptoms of the condition, a reduction in the severity of the condition, or the complete ablation of the condition.

Disclosed are methods of enhancing complement-mediated damage comprising administering to a subject the composition of the invention, which activates complement.

Also disclosed are methods of the invention, wherein the condition is a cancer. The cancer can be selected from the group consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumours, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

In one embodiment of the invention CR2 can target complement deposited on tumor cells as a result of administered anti-tumor antibodies, or as a result of a normally ineffective humoral immune response.

Thus the present complement activating composition can be administered in conjunction with anti-tumor antibodies. Examples of such anti-tumor antibodies are well known and include anti-PSMA monoclonal antibodies J591, PEQ226.5, and PM2P079.1 (Fracasso, G. et al., (2002) Prostate 53(1): 9-23); anti-Her2 antibody hu4D5 (Gerstner, R. B., et al., (2002) J. Mol. Biol. 321(5): 851-62); anti-disialosyl Gb5 monoclonal antibody 5F3 which can be used as an anti renal cell carcinoma antibody (Ito A. et al., (2001) Glycoconj. J. 18(6): 475-485); anti MAGE monoclonal antibody 57B (Antonescu, C. R. et al., (2002) Hum. Pathol. 33(2): 225-9); anti-cancer monoclonal antibody CLN-Ig (Kubo, O. et al., (2002) Nippon Rinsho. 60(3): 497-503); anti-Dalton's lymphoma associated antigen (DLAA) monoclonal antibody DLAB (Subbiah, K. et al., (2001) Indian J. Exp. Biol. 39(10): 993-7). The present composition can be administered before, concurrent with or after administration of the anti-tumor antibody, so long as the present composition is present at the tumor during the time when the antibody is also present at the tumor.

A representative but non-limiting list of cancers that the disclosed compositions can be used to treat is the following: lymphoma, B cell lymphoma, T cell lymphoma, mycosis fungoides, multiple myeloma, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, urothelial carcinomas, adenocarcinomas, sarcomas, gliomas, high grade gliomas, blastomas, neuroblastomas, plasmacytomas, histiocytomas, adenomas, hypoxic tumours, myelomas, AIDS-related lymphomas or sarcomas, metastatic cancers, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma; large bowel cancer, hematopoietic cancers; testicular cancer; colon and rectal cancers, stomach cancer, prostatic cancer, Waldenstroms disease or pancreatic cancer.

The complement activating compositions disclosed herein can also be used for the treatment of precancer conditions such as cervical and anal dysplasias, other dysplasias, severe dysplasias, hyperplasias, atypical hyperplasias, and neoplasias. Disclosed are methods of the invention, wherein the condition is a precancer conditions. It is understood that the composition will recognize antigens that are overexpressed on the surface of precancerous cells Also disclosed are methods of using the complement activating compositions of the invention to treat viral infection. The viral infection can be selected from the list of viruses consisting of Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods of using the complement activating compositions of the invention to treat a bacterial infection. Also disclosed are methods of the invention, wherein the bacterial infection can be selected from the list of bacterium consisting of *M. tuberculosis*, *M. bovis*, *M. bovis* strain BCG, BCG substrains, *M. avium*, *M. intracellulare*, *M. africanum*, *M. kansasii*, *M. marinum*, *M, ulcerans*, *M. avium* subspecies *paratuberculosis*, *Nocardia asteroides*, other *Nocardia* species, *Legionella pneumophila*, other *Legionella* species, *Salmonella typhi*, other *Salmonella* species, *Shigella species*, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Cowdria ruminantium*, *Chlamydia pneumoniae*, *Chlamydia trachomatis*, *Chlamydia psittaci*, *Coxiella burnetti*, other Rickettsial species, *Ehrlichia* species, *Staphylococcus aureus*, *Staphylococcus epidermidis*, *Streptococcus pyogenes*, *Streptococcus agalactiae*, *Bacillus anthracis*, *Escherichia coli*, *Vibrio cholerae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, other *Clostridium* species, *Yersinia enterolitica*, and other *Yersinia* species.

Also disclosed are methods of using the complement activating compositions of the invention to treat a parasitic infection. Also disclosed are methods of the invention, wherein the parasitic infection can be selected from the group consisting of *Toxoplasma gondii*, *Plasmodium falciparum*, *Plasmodium vivax*, *Plasmodium malariae*, other *Plasmodium* species, *Trypanosoma brucei*, *Trypanosoma cruzi*, *Leishmania major*, other *Leishmania* species, *Schistosoma mansoni*, other *Schistosoma* species, and *Entamoeba histolytica*.

Also disclosed are methods of using the complement activating compositions of the invention to treat a fungal infection. Also disclosed are methods of the invention, wherein the fungal infection can be selected from the group consisting of *Candida albicans*, *Cryptococcus neoformans*, *Histoplama capsulatum*, *Aspergillus fumigatus*, *Coccidiodes immitis*, *Paracoccidiodes brasiliensis*, *Blastomyces dermitidis*, *Pneomocystis carnii*, *Penicillium marneffi*, and *Alternaria alternata*. In the methods of the invention, the subject can be a mammal. For example, the mammal can be a human, nonhuman primate, mouse, rat, pig, dog, cat, monkey, cow, or horse.

3. Methods of Using the Compositions as Research Tools

The disclosed compositions can be used in a variety of ways as research tools. For example, the disclosed compositions can be used to study inhibitor of complement activation.

The disclosed compositions can be used as diagnostic tools related to diseases associated with complement activation, such as cancer, viral infections, bacterial infections, parasitic infections, and fungal infections. CR2-fusion proteins will target a site of complement activation and a labeled CR2-fusion protein can diagnose conditions associated with complement activation. For example, a tumor-reactive antibody would activate complement on tumor cells, which CR2 could then target. The labeled CR2-Fc could then amplify the signal following antibody targeting.

D. Compositions

Disclosed are the components to be used to prepare the disclosed compositions as well as the compositions themselves to be used in the methods disclosed herein. These and other materials are disclosed herein, and it is understood that when combinations, subsets, interactions, groups, etc. of these materials are disclosed that while specific reference for each of the various individual and collective combinations and permutation of these compounds may not be explicitly made, each is specifically contemplated and described herein. For example, if a particular CR2, DAF, CD59, CR1, MCP, Crry, IgG1, IgM, IgG3, CVF is described, and/or a specific combination thereof is disclosed and discussed and/or a number of modifications that can be made to a number of molecules including the CR2, DAF, CD59, CR1, MCP, Crry, IgG1, IgM, IgG3, CVF, and/or combination thereof are discussed, specifically contemplated is each and every combination and permutation of CR2, DAF, CD59, CR1, MCP, Crry, IgG1, IgM, IgG3, CVF, or combination thereof and the modifications that are possible, unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the genes and proteins disclosed herein, is through defining the variants and derivatives in terms of homology to specific known sequences. This identity of particular sequences disclosed herein is also discussed elsewhere herein. For example SEQ ID NO: 25 sets forth a particular sequence of a CR2 and SEQ ID NO: 26 sets forth a particular sequence of the protein encoded by SEQ ID NO: 25, a CR2 protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Nucleic Acids

There are a variety of molecules disclosed herein that are nucleic acid based, including for example the nucleic acids that encode, for example CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-anti-05, CR2-IgG1 Fc (human), CR2-IgM Fc, CR2-IgG3 Fc (murine), or CR2-CVF, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and related molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$, alkyl or $C_2$ to $C_{10}$ alkenyl and alkynyl. 2' sugar modifications also include but are not limited to —O[$(CH_2)_nO]_m$ $CH_3$, —O$(CH_2)_n$OCH$_3$, —O$(CH_2)_n$NH$_2$, —O$(CH_2)_n$CH$_3$, —O$(CH_2)_n$—ONH$_2$, and —O$(CH_2)_n$ON[$(CH_2)_n$CH$_3$]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S, Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al.; EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF genes having, for example, the sequences as disclosed herein or sequences available in the literature. These sequences and others are herein incorporated by reference in their entireties as well as for individual subsequences contained therein.

One particular sequence set forth in SEQ ID NO: 25 used herein, as an example, to exemplify the disclosed compositions and methods. It is understood that the description related to this sequence is applicable to any sequence related to CR2, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF unless specifically indicated otherwise. Those of skill in the art understand how to resolve sequence discrepancies and differences and to adjust the compositions and methods relating to a particular sequence to other related sequences (i.e. sequences of CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF). Primers and/or probes can be designed for any CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF sequence given the information disclosed herein and known in the art.

3. Delivery of the Compositions to Cells

There are a number of compositions and methods which can be used to deliver the present fusion protein compositions, immunoconjugate compositions, and nucleic acid compositions to cells, either in vitro or in vivo. Compositions of the invention are preferably administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carriers include, but are not limited to, saline, water:oil emulsions, oil:water emulsions, water:oil:water emulsions, and Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The compositions of the invention can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering the compositions of the invention can be determined empirically, and making such determinations is within the skill in the art. Those skilled in the art will understand that the dosage of the compositions of the invention that must be administered will vary depending on, for example, the subject that will receive the composition, the route of administration, the particular type of composition used and other drugs being administered. A typical daily dosage of the compositions of the invention used alone might range from about 1 µg/kg to up to 100 mg/kg of body weight or more per day, depending on the factors mentioned above.

a) Nucleic Acid Based Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, S. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as SEQ ID NO: 25 into the cell without degradation and include a promoter yielding expression of the gene in the cells into which it is delivered. In some embodiments the CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVFs are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology—1985, American Society for Microbiology, pp. 229-232, Washington, (1985), which is incorporated by reference herein. Examples of methods for using retroviral vectors for gene therapy are described in U.S. Pat. Nos. 4,868, 116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., I. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fe, CR2-IgG3 Fc (murine), or CR2-CVF or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis, has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

a) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983))

as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. Science 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Peptides a) Protein Variants

As discussed herein there are numerous variants of the CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), and CR2-CVF protein that are known and herein contemplated. In addition, to the known functional CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), and CR2-CVF strain variants, there are derivatives of the CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), and CR2-CVF proteins which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala A |
| allosoleucine | AIle |
| arginine | Arg R |
| asparagine | Asn N |
| aspartic acid | Asp D |
| cysteine | Cys C |
| glutamic acid | Glu E |
| glutamine | Gln Q |
| glycine | Gly G |
| histidine | His H |
| isolelucine | Ile I |
| leucine | Leu L |
| lysine | Lys K |
| phenylalanine | Phe F |
| proline | Pro P |
| pyroglutamic acidp | pGlu |
| serine | Ser S |
| threonine | Thr T |
| tyrosine | Tyr Y |
| tryptophan | Trp W |
| valine | Val V |

TABLE 2

Amino Acid Substitutions
Original Residue Exemplary Conservative
Substitutions, others are known in the art.

Ala; Ser
Arg; Lys; Gln
Asn; Gln; His
Asp; Glu
Cys; Ser
Gln; Asn, Lys
Glu; Asp
Gly; Pro
His; Asn; Gln
Ile; Leu; Val
Leu; Ile; Val
Lys; Arg; Gln;

TABLE 2-continued

Amino Acid Substitutions
Original Residue Exemplary Conservative
Substitutions, others are known in the art.

Met; Leu; Ile
Phe; Met; Leu; Tyr
Ser; Thr
Thr; Ser
Trp; Tyr
Tyr; Trp; Phe
Val; Ile; Leu

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 26 sets forth a particular sequence of CR2 and SEQ ID NO: 2 sets forth a particular sequence of a DAF protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:26 is set forth in SEQ ID NO:25. In addition, for example, a disclosed conservative derivative of SEQ ID NO:26 is shown in SEQ ID NO: 29, where the isoleucine (I) at position 9 is changed to a valine (V). It is understood that for this mutation all of the nucleic acid sequences that encode this particular derivative of any of the disclosed sequences are also disclosed. It is also understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

6. Antibodies a) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof; as described herein. The antibodies are tested for their desired activity using the in vitro assays described herein, or by analogous methods, after which their in vivo therapeutic and/or prophylactic activities are tested according to known clinical testing methods.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid, sequence of the constant domain of their heavy chains, immunoglobulins can be assigned to different classes. There are five major classes of human immunoglobulins: IgA, IgD, IgE, IgG and IgM, and several of these can be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as scFv, sFv, F(ab')2, Fab', Fab and the like, including hybrid fragments. Thus, fragments of the antibodies that retain the ability to bind their specific antigens are provided. For example, fragments of antibodies which maintain complement binding activity binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Optionally, the antibodies are generated in other species and "humanized" for administration in humans. Humanized forms of non-human (e.g., murine) antibodies are chimeric immunoglobulins, immunoglobulin chains or fragments thereof (such as Fc, scFv, sFv, Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides can be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with an Fc receptor. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody can be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats can be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof of the invention and one or more reagents for detecting binding of the antibody or fragment thereof to the Fc receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

b) Human Antibodies

The human antibodies of the invention can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies of the invention (and fragments thereof) can also be produced using phage display libraries (Hoogenboom et al., *J. Mol. Biol.*, 227:381, 1991; Marks et al., *J. Mol. Biol.*, 222:581, 1991).

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

c) Administration of Antibodies

Antibodies of the invention are preferably administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering the antibodies can be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of an antibody for treating, inhibiting, or preventing an HIV infection, the efficacy of the therapeutic antibody can be assessed in various ways well known to the skilled practitioner. For instance, one of ordinary skill in the art will understand that an antibody of the invention is efficacious in treating or inhibiting an HIV infection in a subject by observing that the antibody reduces viral load or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood) from a subject or patient, or by measuring the level of circulating anti-HIV antibody levels in the patient. Efficacy of the antibody treatment can also be determined by measuring the number of $CD4^+$ T cells in the HIV-infected subject. An antibody treatment that inhibits an initial or further decrease in $CD4^+$ T cells in an HIV-positive subject or patient, or that results in an increase in the number of $CD4^+$ T cells in the HIV-positive subject, is an efficacious antibody treatment.

d) Nucleic Acid Approaches for Antibody Delivery

The compositions of the invention can also be administered to patients or subjects as a nucleic acid preparation (e.g., DNA or RNA) that encodes the antibody or antibody fragment, such that the patient's or subject's own cells take up the nucleic acid and produce and secrete the encoded composition (e.g., CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF).

e) Nucleic Acid Delivery

In the methods described above which include the administration and uptake of exogenous DNA into the cells of a subject (i.e., gene transduction or transfection), the nucleic acids of the present invention can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these or other commonly used gene transfer methods.

As one example, if the complement modulating construct-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

7. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter is effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

8. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth herein wherein the sequences do not include SEQ ID Nos: 37, 38, 39, 40, 41, and 42.

9. Compositions Identified by Screening with Disclosed Compositions a) Computer Assisted Drug Design The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.]

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF are also disclosed. Thus, the products produced using the molecular modeling approaches that involve the disclosed compositions, such as, CR2, DAF, CD59, CR1, MCP, Crry, IgG1, IgM, IgG3, CVF, CR2-DAF, DAF-CR2, CR2-CD59, CD59-CR2, CR2-CR1, CR1-CR2, CR2-MCP, MCP-CR2, CR2-Crry, Crry-CR2, CR2-IgG1 Fc (human), CR2-IgM Fc, CR2-IgG3 Fc (murine), or CR2-CVF, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

10. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for cancer, asthma, systemic lupus erythematosus, rheumatoid arthritis, reactive arthritis, spndyarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, Ischemia reperfusion injury, myocardial infarction, alzheimer's disease, transplant rejection (allogeneic and xenogeneic), thermal trauma, any immune complex-induced inflammation, glomerulonephritis, myasthenia gravis, multiple sclerosis, cerebral lupus, Guillain-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bullous pemphigoid, stroke, atherosclerosis, and scleroderma.

11. Compositions with Similar Functions

It is understood that the compositions disclosed herein have certain functions, such as modulating complement activity or binding CR2, CR3, or C3b. Disclosed herein are certain structural requirements for performing the disclosed functions, and it is understood that there are a variety of structures which can perform the same function which are related to the disclosed structures, and that these structures will ultimately achieve the same result, for example stimulation or inhibition complement activity.

E. Methods of Making the Compositions

The compositions disclosed herein and the compositions necessary to perform the disclosed methods can be made using any method known to those of skill in the art for that particular reagent or compound unless otherwise specifically noted.

Disclosed are methods of making a composition comprising a construct, wherein the construct comprises CR2 and a modulator of complement. Also disclosed are methods of making a composition, wherein the composition is the composition of the invention.

1. Peptide Synthesis

One method of producing the disclosed proteins, such as SEQ ID NO: 6, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

2. Process for Making the Compositions

Disclosed are processes for making the compositions as well as making the intermediates leading to the compositions. For example, disclosed are nucleic acids in SEQ ID NOs: 5. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO: 25 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO: 25, and a sequence controlling the expression of the nucleic acid.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the Dr. Tomlinson regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Complement Receptor 2 (CR2)-Mediated Targeting of Complement Inhibitors to Sites of Complement Activation a) Methods
(1) Cell Lines and DNA.

All DNA manipulations were carried out in the mammalian expression vector PBM, derived from p118-mIgG1 (30) by deletion of mouse IgG1, Fc coding region. Chinese hamster ovary (CHO) cells were used for protein expression and were maintained in Dulbecco's modified Eagle's medium (DMEM) (GIBCO Invitrogen Corp, Carlsbad, Calif.) supplemented with 10% FCS. Stably transfected CHO cell clones were cultivated in the presence of G418, and for recombinant protein expression cells were cultured in suspension in CHO-S-SFM II without FCS (GIBCO). U937 cells were cultured in RPMI (GIBCO), 10% FCS.

(2) Antibodies, Reagents and Serum.

Rabbit antiserum to CHO cell membrane, purified human DAF and CD59 was prepared by standard techniques (31). Mouse anti-DAF mAb 1H4 (32), rat anti-CD59 mAb YTH53.1 (33) and mouse anti human CR2 mAb 171 (binds to SCR 1-2) (34) are described. Anti-sheep erythrocyte IgM was from Research Diagnostic Inc. (Flanders, N.J.). All secondary antibodies were purchased from Sigma (St. Louis, Mo.). Purified recombinant sCD59 was a gift from Dr. B. P. Morgan (University of Wales, Cardiff, UK). C6-depleted human serum was purchased from Quidel (San Diego, Calif.) and normal human serum (NHS) was obtained from the blood of healthy volunteers in the laboratory.

(3) Construction of Expression Plasmids and Protein Expression.

Figure 1:
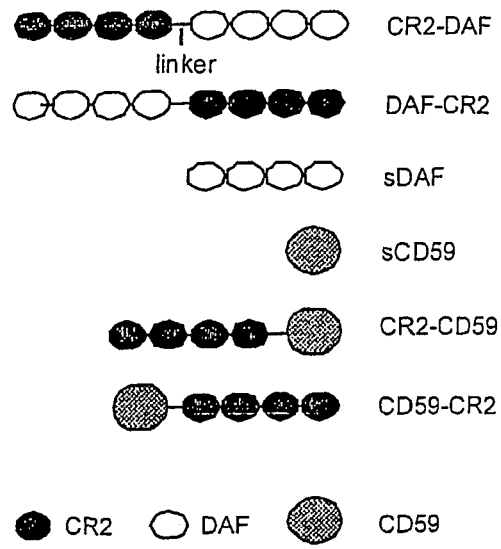

The recombinant fusion proteins and soluble complement inhibitors prepared are depicted in FIG. 1. cDNA constructs were prepared by joining the CR2 sequence encoding the 4 N-terminal SCR units (residues 1-250 of mature protein, Swissprot accession no. P20023) to sequences encoding extracellular regions of DAF or CD59. The complement inhibitor sequences used encoded residues 1-249 of mature DAF protein sequence (Swissprot accession no. P08174) and residues 1-77 of mature CD59 protein sequence (Swissprot accession no. P13987). To join CR2 to complement inhibitor sequences, linking sequences encoding SS(GGGGS)$_3$ and (GGGS)$_2$ were used for fusion proteins containing CR2 at the C-terminus and N-terminus, respectively. Gene constructs were prepared by standard PCR methodology (35). All cloning steps were performed in the PBM vector that was also used for protein expression (30). For expression, plasmids were transfected into CHO cells using lipofectamine according to manufacturer's instructions (GIBCO). Stably transfected clones were selected by limiting dilution as described (30) and protein expression of clones quantitated by ELISA.

(4) ELISA and Protein Assays.

Detection of recombinant proteins and determination of relative protein concentration in culture supernatants was achieved using a standard ELISA technique (31). Depending on which type of recombinant protein was being assayed, the capture antibody was either anti-DAF mAb 1114 or anti-CD59 mAb YTH53.1. Primary detection antibodies were either anti-DAF or anti-CD59 rabbit polyclonal antibody. In some ELISAs, anti-CR2 mAb A-3 was also used as primary detection antibody, and although less sensitive, similar data was obtained. The protein concentration of recombinant proteins was determined either by UV absorbance or by using a BCA protein assay kit (Pierce Chemical Company, Rockford Ill.).

(5) Protein Purification.

Recombinant proteins were purified from culture supernatant by affinity chromatography. Affinity columns were prepared by coupling either anti-DAF 1H4 mAb or anti-CD59 YTH53.1 mAb to HiTrap NHS-activated affinity columns (Pharmacia Biotech, New Jersey, USA) as described by the manufacturer. Culture supernatants containing recombinant proteins were adjusted to pH 8.0 and applied to affinity columns at a flow rate of 0.5 ml/min. The column was washed with 6 to 8 column volumes of PBS, and recombinant proteins eluted with 2 to 3 column volumes of 0.1 M glycine, pH 2.4. The fractions containing fusion protein were collected into tubes containing 1 M Tris buffer, pH 8.0 and dialyzed against PBS.

(6) SDS-PAGE and Western Blotting.

Purified recombinant proteins were separated in SDS-PAGE 10% acrylamide gels (Bio-Rad Life Science, Hercules, Calif.) under nonreducing conditions. Gels were stained with Coomassie blue. For Western blotting, standard procedures were followed (31). Briefly, separated proteins were transferred to a polyvinylidene fluoride membrane, and the transferred proteins detected by means of either anti-DAF mAb 1H4 or anti-CD59 mAb YTH53.1. Membranes were developed with ECL detection kit (Amersham Biosciences, Piscataway, N.J.). CR2-CD59 was also analyzed by SDS-PAGE following glycanase treatment. CR2-CD59 (2 mg) was heated at 95° C. for 3 min in 15 mM sodium phosphate buffer (pH 7.5) containing 0.1% SDS, 10 mM 2-mercaptoethanol and 5 mM EDTA. After cooling, CR2-CD59 was incubated with 3 U of *Flavobacterium meningosepticum* N-glycanase (EC 3.5.1.52, Sigma) for 20 h at 37° C. in the presence of 1% Nonidet P40 and 0.3 mM PMSF.

(7) Flow Cytometry.

Binding of recombinant fusion proteins to C3-opsonized cells was determined by flow cytometry. CHO cells were incubated in 10% anti-CHO antiserum (30 min/4° C.), washed and incubated in 10% C6-depleted NHS (45 min/37° C.). The C3 opsonized cells were then washed and incubated with 1 µM recombinant protein (60 min/4° C.). After washing, cells were incubated with 10 µg/ml of either anti-DAF mAb 1H4 or anti-CD59 mAb YTH53.1 as appropriate (30 min/4° C.), followed by FITC-conjugated secondary antibody (1:100, 30 min/4° C.). Cells were then washed, fixed with 2% paraformaldehyde in PBS, and analyzed using a FACScan flow cytometer (Becton Dickinson Immunocytometry Systems, San Jose, Calif.). All incubations and washes were performed in DMEM.

(8) Analysis of CR2 Fusion Protein Binding to C3 Ligand.

Kinetic analysis of the interaction of the CR2 fusion proteins with C3dg-biotin was performed using surface plasmon resonance (SPR) measurements made on a BIAcore 3000 instrument. Human C3dg-biotin, prepared as described (36), was bound to the surface of BIAcore streptavidin (SA) sensor chips by injecting C3dg-biotin at 50 µg/ml over the surface of one flow cell of the chip at 2 µl/minute for 20 minutes. The flow buffer was 0.5×PBS+0.05% Tween 20. The SPR signal from captured C3dg generated BIAcore response units ranging from 250-500. Control streptavidin-coated 1.5 flow cells were run in the absence of protein. Binding was evaluated over a range of CR2 fusion protein concentrations (15.6-500 nM) in 0.5×PBS, 0.05% Tween 20 at 25° C. at a flow rate of 25 µl/minute. CR2 fusion protein samples were injected in 50 µl aliquots using the kinject command. Association of the fusion proteins with the ligand was monitored for 120 seconds, after which the complex was allowed to dissociate in the presence of buffer only for an additional 120 seconds. The binding surface was regenerated between analyses of different fusion protein concentrations by a 10 second pulse of 200 nM sodium carbonate (pH 9.5) at 50 µl/min. Binding of CR2 fusion protein fragments to C3d-immobilized flow cells was corrected for binding to control flow cells. Binding data were fitted to a 1:1 Langmuir binding model using BIAevaluation Version 3.1 software (BIAcore) and evaluated for best fit by low residual and χ2 values. The kinetic dissociation profiles obtained were used to calculate on and off-rates ($k_a$ and $k_d$) and affinity constants ($K_D$) using the BIAevaluation Version 3.1 program. Between experiments, the streptavidin surface was regenerated with a 60-s pulse of 50 mM sodium hydroxide (pH 9.5) at 50 µl/minute, and C3dg-biotin was reapplied as described above.

(9) Complement Lysis Assays.

CHO cells at 60%-80% confluence were detached with versene (GIBCO), washed twice, and resuspended to $10^6$/ml in DMEM. Cells were sensitized to complement by adding 10% rabbit anti-CHO cell membrane antiserum to cells (30 min/4° C.). Antiserum was then removed and cells resuspended in NHS diluted in DMEM. Final assay volumes were either 50 or 100 After 45 min at 37° C., cell viability was determined either by trypan blue exclusion (both live and dead cells counted) or $^{51}$Cr release (37). Both assays gave similar results. To assay complement inhibitory activity of recombinant proteins, the proteins were diluted in DMEM and added to NHS before addition to CHO cells. A final concentration of 10% NHS was used which resulted in approximately 90% lysis of unprotected antibody sensitized CHO cells. Inhibition of complement-mediated hemolysis was determined using antibody-sensitized sheep erythrocytes (EA) (Advanced Research Technologies, San Diego, Calif.). Hemolytic assays were carried out in gelatin veronal buffer (GVB$^{++}$) (Advanced Research Technologies) in a final volume of 300 µl containing 2.5×$10^7$ EA, NHS at a final dilution of 1/300 and incremental concentrations of fusion protein. Reaction mixtures were incubated at 37° C. for 60 min and reactions were stopped by addition of 300 µl PBS containing 10 mM EDTA. Cells were removed by centrifugation and cell lysis assayed by spectrophotometric quantitation of hemoglobin in the supernatant at 413 nm.

(10) Adhesion of U937 Cells to Erythrocytes.

Assays of CR3-dependent adhesion to C3-opsonized erythrocytes were performed essentially as described (38). Briefly, fresh sheep erythrocytes (SRBC) were sensitized with a pre-determined sub-agglutinating amount of rabbit anti-SRBC IgM for 30 min at 37° C. in GVB (Advanced Research Technologies). After washing twice, C3b-opsonized SRBC were prepared by incubating IgM-sensitized SRBC with an equal volume of a 1:2 dilution of C6-deficient human serum in GVB (120 min/37° C.). Cells were washed twice and pellets resuspended in GVB. The majority of C3 bound to erythrocytes following this treatment is in the form of iC3b or C3d degradation products (CR2 ligands) due to the short half life of C3b in serum. U937 cells (4×$10^5$ cells in 200 µl) were added to 50 µl of C3 opsonized SRBC (2×$10^6$ cells) and the mixture centrifuged (4 min/40×g) and left at room temperature for 90 min. Cells were then examined by phase contrast microscopy and number of U937 cells adherent to erythrocytes determined. At least 100 erythrocytes were scored per sample, and average number of U937 cells bound per erythrocyte calculated. Triplicate determinations were made for each experiment performed. In some experiments, U937 cells were cultured for 3 days in the presence of 50 ng/ml phorbol myristate acetate (PMA) before harvest, a treatment that results in upregulation of CR3 (39, 40). Cells incubated with IgM-coated SRBC alone, or SRBC incubated directly with C6-deficient human serum were used as controls.

(11) Biodistribution Studies.

Standard procedures for determining tissue distribution of injected radiolabeled proteins were followed (41, 42). Briefly, 1.7 µg of $^{125}$I-labeled CR2-DAF (4.20×$10^6$ cpm/mg) or sDAF (4.84×$10^6$ cpm/mg) were injected into the tail vein of 34 week old female NZB/NZW F1 mice (Jackson Labs, Bar Harbor, Me.). After 24 h, a blood sample was taken and major organs were removed, shredded and washed in PBS containing 10 mM EDTA, weighed and counted. Targeting specificity was evaluated as percent injected dose per gram tissue. Proteins were iodinated using iodogen method according to manufacturers instructions (Pierce Chemical Co.).

(12) Immunofluorescence Microscopy.

CR2-DAF or sDAF (270 µg) was injected into the tail vein of 24-week-old MRL/lpr mice. Twenty-four hours later, kidneys were removed and snap frozen. Cryostat sections (5 µm) prepared from frozen kidneys were fixed in acetone and processed for indirect immunofluorescence microscopy. An equimolar mixture of mouse antihuman DAF 1A10 and 1H6 mAbs were used as primary detection antibodies (final concentration, 10 µg/ml) with an anti-mouse IgG Fc-specific FITC-conjugated secondary antibody (F4143, Sigma-Aldrich). Standard procedures were followed (49, incorporated herein by reference for its teaching of antibody staining techniques), except that to reduce background staining, most likely caused by deposited immune complexes in the mouse kidney, the secondary FITC-labeled antibody was diluted 1:800 (10 times the recommended dilution). Digital images were acquired and optimized with Adobe Photoshop using identical settings.

b) Results (1) Construct Design, Expression and Purification.

Recombinant fusion proteins contained the four N-terminal SCR units of human CR2 linked to either the N or C terminus of soluble forms of human CD59 or DAF (constructs depicted in FIG. 1). Recombinant proteins were purified from the culture supernatant of stably transfected CHO cell clones with yields of between 100-200 Analysis of purified recombinant proteins by SDS-PAGE and Western blot revealed proteins within expected molecular weight range (FIG. 2), and except for CR2-CD59, all proteins migrated as a single band. The two bands seen for CR2-CD59 were due to differences in glycosylation, since CR2-CD59 migrated as a single band following glycanase treatment.

(2) Targeting of Fusion Proteins to Complement Opsonized Cells.

Figure 3:
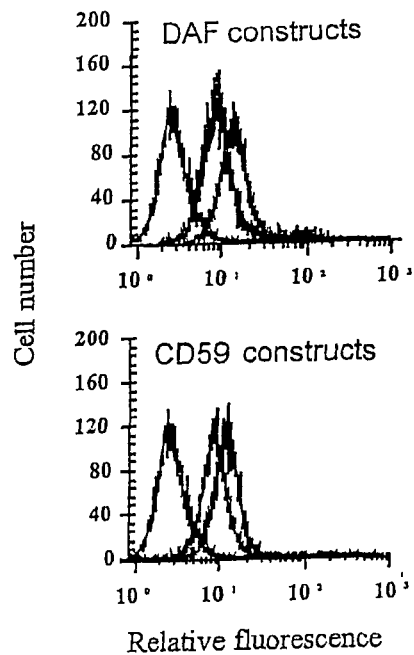

C3 ligand for CR2 was deposited on CHO cells by incubation of CHO cells with complement activating antibody and C6-depleted serum (to prevent MAC formation and cell lysis). All CR2-containing fusion proteins, but not sCD59 or sDAF, bound to C3-coated CHO cells (FIG. 3).

(3) Kinetic Analysis of Interaction Between Fusion Proteins and C3dg Ligand.

Figure 4:
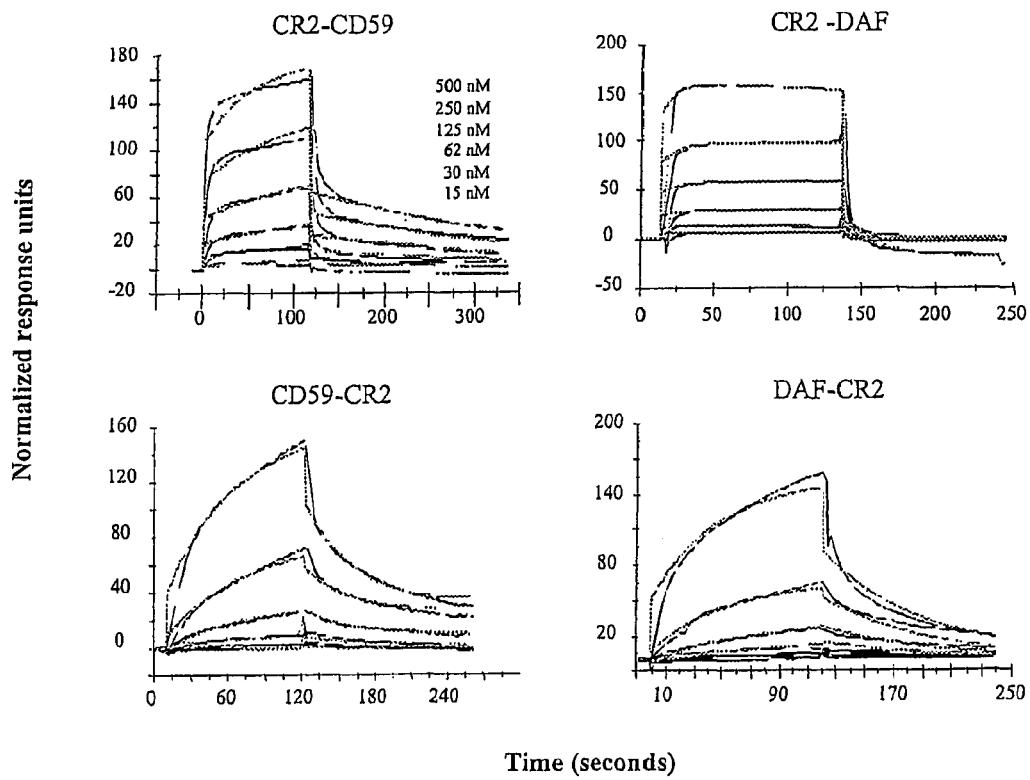

A comparison of the affinity of the different recombinant fusion proteins for the CR2 ligand C3dg was determined by surface plasmon resonance measurements. The experiments were performed by passing varying concentrations of the fusion proteins over Biacore streptavidin chips containing captured C3dg-biotin (approximately 2000 response units). Kinetic analysis of the data showed the best fit to a 1:1 (Langmuir) binding interaction model using global fitting parameters (FIG. 4). Both of the fusion proteins with CR2 at the N-terminus (CR2-DAF and CR2-CD59) showed similar binding profiles, with a fast association and a fast dissociation rate. In contrast, binding of fusion proteins with CR2 at the C-terminus (DAF-CR2 and CD59-CR2) showed slow association and dissociation rates (FIG. 4, Table 1). The N-terminus CR2 fusion proteins, however, bound with the highest affinity (Table 1). CD59 fusion proteins bound with a higher affinity than DAF fusion proteins. Soluble DAF and sCD59 did not bind to immobilized C3dg.

(4) Complement Inhibitory Activity of Fusion Proteins.

Figure 5:
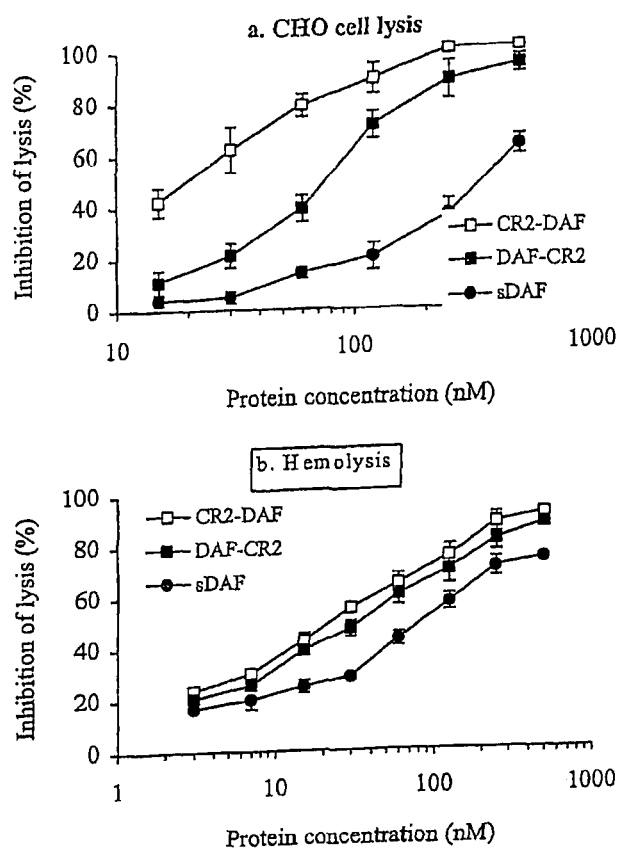
Figure 6:
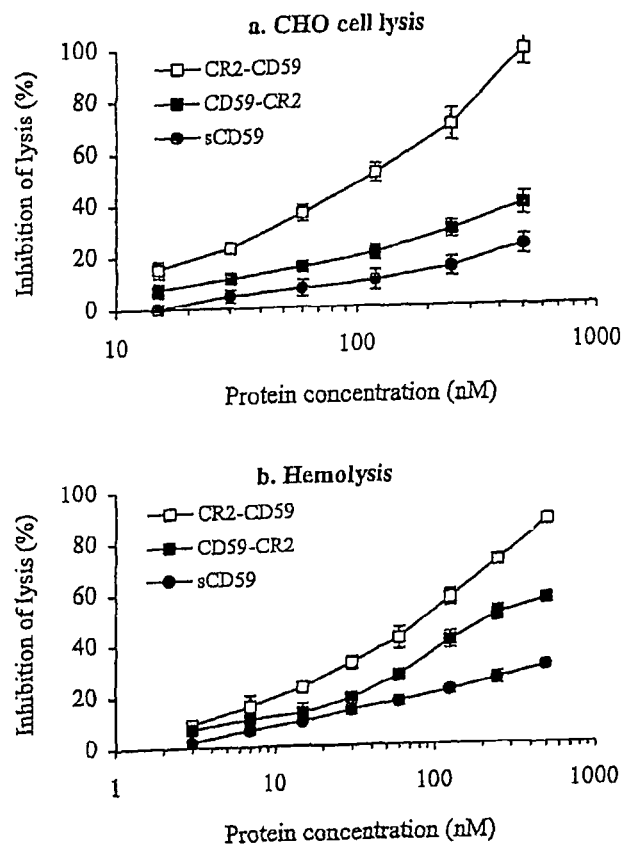

Complement inhibitory activity of the targeted and untargeted complement inhibitors was analyzed by measuring their effect on complement-mediated lysis of both CHO cells and erythrocytes. In these experiments, antibody sensitized cells and recombinant proteins were incubated in human serum at a concentration that resulted in 90-100% lysis of unprotected cells. For both cell types, the targeted complement inhibitors were significantly more effective than their respective untargeted proteins at inhibiting complement-mediated lysis. Targeted DAF proteins were more effective inhibitors than targeted CD59 (FIGS. 5 and 6). Fusion proteins containing CR2 linked to the N-terminus of either DAF and CD59 were more effective inhibitors than C-terminal CR2 fusion proteins. The most potent inhibitor of complement lysis was CR2-DAF, requiring a concentration of 18 nM for 50% inhibition of CHO cell lysis. In contrast, untargeted sDAF required a concentration of 375 nM for 50% inhibition of CHO cell lysis, a 20-fold difference (FIG. 5a). sCD59 was a particularly poor inhibitor of complement and provided only 25% protection from CHO cell lysis at 500 nM, the highest concentration tested. CR2-CD59, however, provided 50% inhibition of CHO cell lysis at 102 nM and was more effective than untargeted sDAF (FIG. 6a). Table 4 compares the inhibitory activities of the different recombinant complement inhibitors. The higher complement inhibitory activity of the N-terminus CR2 fusion proteins correlated with the higher affinity these proteins exhibited for C3dg ligand (Table 3).

There were some differences between the relative effectiveness of the complement inhibitors at protecting CHO cells and erythrocytes form complement-mediated lysis. This was particularly true for the DAF inhibitors; sDAF was significantly more effective at protecting erythrocytes than CHO cells from complement, although targeted DAF was still more effective. There was also little difference in the inhibitory activity of CR2-DAF and DAF-CR2 when erythrocytes were the target cells for complement lysis.

(5) Effect of CR2-Fusion Proteins on Cell Adhesion.

Figure 7:
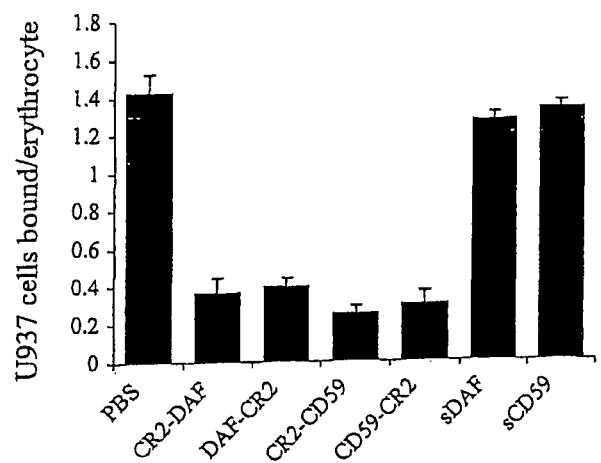

Complement receptor 3 is a leukocyte receptor involved in endothelial adhesion and diapedesis and the activation of cell cytolytic mechanisms (phagocytosis and degranulation). Since CR2 and CR3 share the same iC3b complement ligand, it was determined whether CR2 fusion proteins interfered with CR3-mediated cell binding. For these experiments U937, a well characterized promonocytic cell line (CRT, CR3) that binds to iC3b coated erythrocytes in a CR3-dependent mechanism, was used (40). All of the CR2 fusion proteins, but not sDAF or sCD59, significantly inhibited the binding of U937 cells to C3 opsonized sheep erythrocytes (P<0.01). Each CR2 fusion protein inhibited U937 binding to a similar extent at a concentration of 500 nM (FIG. 7). Similar data was obtained in an experiment using U937 cells that were stimulated with PMA, a treatment that results in upregulation of CR3 (39, 40). For complement opsonization of erythrocytes, IgM was used to activate complement since IgG deposited on the erythrocytes would engage Fcγ receptors expressed on U937 cells. U937 cells also express CR4 (p150, 95, CD11c/CD18), a third receptor sharing the iC3b ligand. However, binding of U937 cells to C3-opsonized erythrocytes is CR4-independent, probably due to the association of CR4 with the cytoskeleton and its immobility in the membrane (40).

(6) Targeting of CR2-DAF to the Kidneys of Nephritic Mice.

To determine whether a CR2 fusion protein will target a site of complement activation and disease in vivo, a biodistribution study of CR2-DAF and sDAF in female NZB/W F1 mice was performed. NZB/W F1 mice develop a spontaneous autoimmune disease that is very similar to human systemic lupus erythematosus (SLE), with the production of autoantibodies and the development of severe immune complex-mediated glomerulonephritis that is associated with complement deposition from 26 to 28 weeks of age (4, 52). Biodistribution of [$^{125}$I]CR2-DAF and [$^{125}$I]sDAF in 34-week-old NZB/W F1 mice was determined at 24 hours and 48 hours after injection. Twenty-four hours after tail-vein injection of [$^{125}$I]CR2-DAF, a significantly higher proportion of radioactivity was localized to the kidney than to the other organs that were examined (FIG. 25a). At 48 hours after injection of [$^{125}$I] CR2-DAF, there was a similar level of radioactivity in the kidney as at 24 hours, but radioactivity in the liver and spleen was increased and blood radioactivity decreased (FIG. 25b). The liver and spleen are sites of immune complex clearance and likely account for increased targeting of [$^{125}$I]CR2-DAF to these organs at the later time point. [$^{125}$I]sDAF showed no preferential binding in the kidney or any other organ (FIG. 25, a and b). In 8-weekold prenephritic NZB/W F1 mice, there was no evidence of [$^{125}$I]CR2-DAF targeting to the kidney (FIG. 25c). Of further interest, [$^{125}$I]sDAF was cleared much more rapidly from the circulation than [$^{125}$I]CR2-DAF, suggesting that the CR2 moiety is functioning to prolong the circulatory half-life of the fusion protein. However, the level of [$^{125}$I]CR2-DAF in the blood of younger mice at 24 hours was about half that recorded in the older mice, and the long circulatory half-life of [$^{125}$I]CR2-DAF may be a consequence, at least in part, of it binding to circulating immune complexes.

Targeting of CR2-DAF to complement deposited in the kidney was also examined in another murine model of SLE by direct examination of kidney sections. Similar to female NZB/W F1 mice, MRL/lpr mice develop severe proliferative glomerulonephritis with the deposition of complement in association with glomerular immune deposits by 24 weeks of age (53, incorporated herein for its teaching of this mouse model). CR2-DAF and sDAF were injected into the tail vein of 24-week-old MRL/lpr mice, and kidney sections were analyzed 24 hours later for human DAF immunoreactivity by fluorescence microscopy. Kidney sections from a mouse injected with CR2-DAF displayed a high level of DAF staining, with preferential localization in glomeruli in a pattern identical to that seen for immune complexes. No DAF staining was evident in glomeruli from a mouse injected with sDAF (FIG. 26).

c) Conclusions

This study describes the generation and characterization of soluble human DAF and CD59 containing proteins that are targeted to a site of complement activation. The targeted proteins were significantly more potent at inhibiting complement than their untargeted counterparts. Targeting of CD59 and DAF was achieved by linking the inhibitors to a fragment of human CR2 that binds complement C3 activation products. The C3 ligands for CR2 are relatively long lived and are covalently bound, often in large quantities, at sites of complement activation. Thus, CR2-mediated targeting of complement inhibition is of therapeutic benefit for numerous complement-associated diseases or disease states. Consistent with this hypothesis, CR2-DAF was shown to target to the kidneys of nephritic NZB/W F1 mice. These mice produce autoantibodies with consequent formation and deposition of immune complexes in the kidney resulting in complement activation and deposition (2, 43). Human CR2 binds human and mouse C3 ligands with similar affinities (44), and the biodistribution studies establish that a CR2-fusion protein retains targeting function in vivo. This study establishes the feasibility of this approach for human complement inhibition. The targeting approach can also be effective for other inhibitors of complement activation such as soluble CR1, which is in clinical trials and is a more potent inhibitor of complement than DAF in vitro (9).

The relative affinities for C3dg of the different CR2 fusion proteins is reminiscent of the affinities of SCR 1-2 of CR2 and SCR 1-15 of CR2 for C3dg. The KD values for CR2 SCR1-2 and CR2 SCR 1-15 interactions with C3dg were similar, but CR2 SCR 1-2 associated and dissociated much faster, indicating a contribution of the additional SCR domains to overall affinity (36). Analysis of the solution structure of another SCR containing protein, factor H, indicated that SCR domains are folded back on themselves and interactions between SCR domains can modulate C3 ligand binding characteristics (45). Conformational variability between SCR domains is predicted to result from different (native) linker lengths, with longer linkers providing greater conformational flexibility. In this context, the CR2 and DAF SCR domains are linked with a relatively long ser-gly linker, and this can permit the fusion partners to fold back on one another resulting in SCR-SCR interactions that can modulate CR2 binding affinity.

Complement-mediated lysis assays were performed using antibody sensitized CHO cells or sheep erythrocytes as targets. There were marked differences in the relative activities of some of the complement inhibitors at protecting the different cells from complement-mediated lysis. sDAF, DAF-CR2, and CD59-CR2 were significantly more effective at protecting sheep erythrocytes than CHO cells from complement-mediated lysis. Unlike erythrocytes, complement-mediated lysis of nucleated cells is not due entirely to colloid osmotic deregulation, and the deposition of multiple MACs in the plasma membrane is required (46-48). The majority of previous studies investigating the inhibitory activity of soluble (untargeted) complement inhibitors have been performed using erythrocytes as target cells for complement mediated lysis. However, CHO cells likely represent a more physiologically relevant target for in vitro experiments.

Different mechanisms of complement-mediated damage are implicated in different disease conditions and different diseases can benefit from inhibition strategies acting at different points in the pathway. For example, if applicable for the disease, a particular benefit of blocking complement at a late step in the pathway would be that host defense functions and immune homeostasis mechanisms of complement would remain intact. Thus, a CD59-based inhibitor would provide advantages over inhibitors of complement activation in diseases in which the terminal cytolytic pathway is primarily implicated in pathogenesis. Soluble CD59 is unlikely to have therapeutic benefit due to its very poor activity in vitro, but it was shown herein that CR2-mediated targeting of CD59 significantly increased its complement inhibitory activity. In fact, CR2-CD59 was more effective at inhibiting complement-mediated lysis than sDAF, and sDAF has shown therapeutic efficacy in vivo (8). Rodent analogues of CR2-CD59 can also be a useful tools for dissecting the relative roles of early complement activation products vs. MAC formation in disease pathogenesis. The relative contributions of the different complement activation products to tissue injury in many disease states is poorly understood and controversial.

The CR2 fusion proteins inhibited the binding of U937 cells to C3-opsonized erythrocytes. CR2 and CR3 both bind iC3b, and this data indicates that CR2 fusion proteins act as CR3 antagonists since U937 binding to C3-opsonized erythrocytes is CR3-dependent (40). As an adhesion molecule, CR3 mediates endothelial adhesion and diapedesis at sites of inflammation via its high affinity interaction with intercellular adhesion molecule-1 (ICAM-1). As a complement receptor, CR3 promotes and enhances phagocytosis and degranulation via its interaction with iC3b. Both ICAM-1 and iC3b bind to overlapping epitopes on CR3 (see Ross review). CR3 can thus be an important determinant in promoting cell-mediated tissue damage at sites of inflammation, and antibodies that block CR3 have shown effectiveness in several inflammatory conditions (see Ross review). The antagonistic effect of CR2 on CR3 binding therefore indicates a second anti-inflammatory mechanism of action of the CR2-complement inhibitor fusion proteins that act synergistically with complement inhibition.

Targeting complement inhibitors to sites of complement activation and disease can considerably enhance their efficacy. Indeed, for disease states that would benefit from CD59-based therapy, the targeting of CD59 to the site of complement activation will be a requirement. An advantage of CR2-mediated targeting over other targeting approaches, such as antibody-mediated targeting, is that the CR2 moiety targets any accessible site of complement activation and has broad therapeutic application. CR2 fusion proteins can also act as CR3 antagonists, and this can represent a second important therapeutic benefit. Human CR2-complement inhibitor fusion proteins are also much less likely to be immunogenic than recombinant inhibitors containing antibody variable regions. The predicted ability of targeted inhibitors of complement activation to provide an effective local concentration with low levels of systemic inhibition also diminishes the possibility of compromising host defense mechanisms, particularly with long term systemic complement inhibition (this is a less important consideration for CD59-based inhibitors). CR2-targeted inhibitors can also target infectious agents that activate complement.

2. Example 2

Targeted Complement Inhibition and Activation a) Complement Inhibitors (Inflammation/Bioincompatibility)

Complement inhibitors hold considerable promise for the therapy of many autoimmune and inflammatory diseases, and disease states associated with bioincompatibility. A safe and effective pharmaceutical inhibitor of complement is not currently available. Research has largely focused on developing soluble inhibitors based on host membrane-bound complement-regulatory proteins. Recombinant forms of soluble CR1, MCP, DAF and Crry have been produced by removal of membrane-linking regions, and all proteins have been shown to be effective at reducing inflammation and complement-mediated tissue damage in various models of disease. Soluble CR1 and an antibody that blocks the function of complement protein C5 are in clinical trials. There are, however, serious questions concerning the clinical use of systemically administered soluble complement inhibitors. Complement plays a crucial role in both innate and adaptive immunity, and the generation of C3b is critical for the opsonization and leukocyte-mediated clearance of many pathogenic microorganisms. In addition, the fluid phase complement activation product C5a has been shown to be important in controlling infection and can be important in the clearance of pathogenic substances from the circulation. Systemic inhibition of complement is therefore likely to have serious consequences for the host regarding its ability to control infection. Complement is also crucial for the effective catabolism of immune complexes, and this is a particularly important consideration in the use of complement inhibitors for the treatment of autoimmune and immune complex diseases.

The targeting of complement inhibitors to sites of complement activation and disease can allow a much lower effective serum concentration and significantly reduce the level of systemic complement inhibition. Increased efficacy is an important benefit of targeted complement inhibitors, and targeting can also address the problem of a short half life of soluble recombinant complement inhibitors in the circulation.

Figure 8:
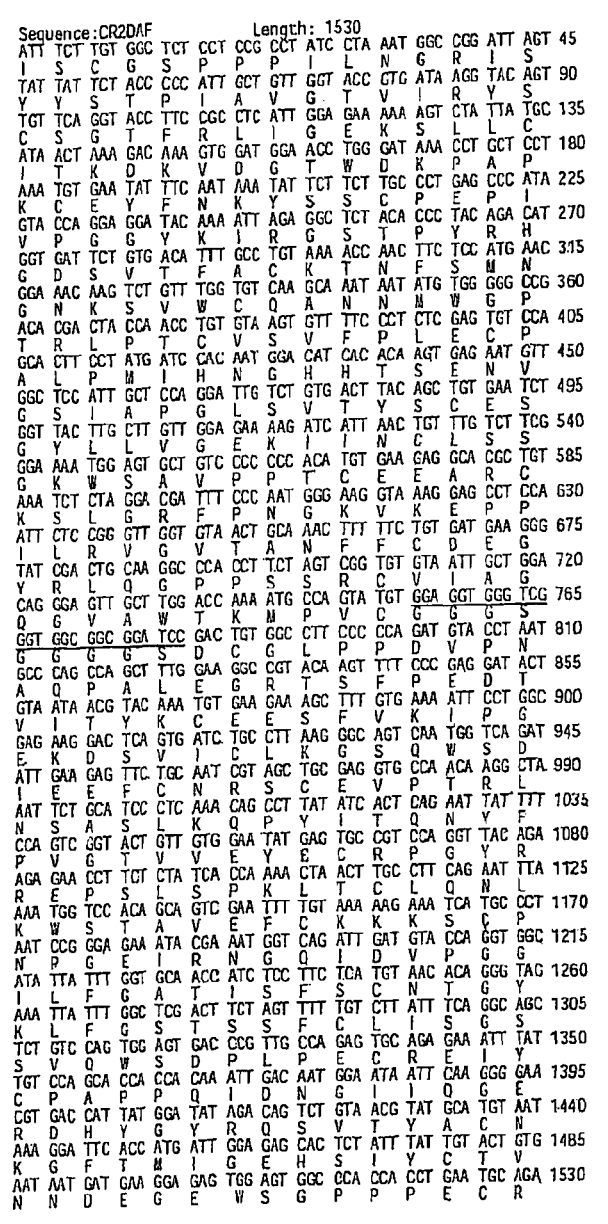

In addition to the above considerations with regard to the targeting of complement inhibitors, selectively blocking different parts of the complement pathway can allow the generation of beneficial complement activation products, but inhibit the generation of complement activation products involved in disease pathogenesis. For example, inhibitors of complement activation (such as CR1, DAF, Crry) inhibit C3b, C5a and C5b-9 generation. Antibodies to C5 inhibit C5a and C5b-9 generation. On the other hand, CD59-based inhibitors do not effect C3b and C5a generation, but block only C5b-9 formation (see FIG. 8). The terminal complement pathway and C5b-9 generation has been shown to be important in promoting inflammation and is in particular implicated in the progression of some diseases of the kidney (such as immune complex glomerulonephritis). Thus, for certain diseases, a CD59-based inhibitor can inhibit disease pathogenesis without interfering with the generation of early complement activation products that are important for host defense and immune complex clearance. However, soluble CD59 is not an effective inhibitor of complement (unlike inhibitors of activation DAF, CR1, MCP or Crry), and is unlikely to have any clinical application. Cell targeted CD59, however, can represent a viable therapeutic. Data using antibody-mediated targeting of CD59 [Zhang et al., 1999, J. Clin. Invest., 103, 55-61], and the data presented herein with CR2-mediated targeting of CD59 show that CD59 targeted to a cell membrane is significantly more effective than soluble untargeted CD59.

b) Complement Activators (Cancer)

The initial promise of anti-tumor complement activating monoclonal antibodies as cancer immunotherapeutic agents has not been realized. One reason for this is the expression of complement inhibitory proteins on tumor cells (complement inhibitors are often upregulated on tumor cells). Thus, although certain antibodies have been shown to target tumors in humans and to activate complement on the tumor cell surface, the tumor cells resist complement-mediated destruction. There is a large body of evidence from in vitro studies indicating an important role for complement inhibitors in tumor resistance to antibody therapy. In addition, reports [Caragine, et al., 2002, Cancer Res, 62, 1110-15; Chen et al., 2000, Cancer Res., 60 3013-18; Baranyi et al., 1994, Immunology, 82, 522-8] have established that complement inhibitors expressed on the surface of tumor cells in vivo have functional consequences with regard to complement deposition and tumorigenesis. Enhancing complement deposition on tumor cells allows more effective immune-mediated clearance of tumor cells and improve prospects for successful immunotherapy using complement-activating anti-tumor antibodies. Enhanced complement activation overwhelms tumor cell expressed complement inhibitory proteins.

c) Results—1

(1) Targeted Complement Inhibitor Fusion Protein

Examples of human fusion proteins that have been expressed, purified and characterized for targeting and assessed for complement inhibitory function in vitro as previously described include the following: CR2-DAF, CR2-CD59, DAF-CR2, and CD59-CR2. The nucleotide sequences and predicted amino acid sequences of mature human fusion proteins are shown in FIGS. 8-11.

Figure 2:
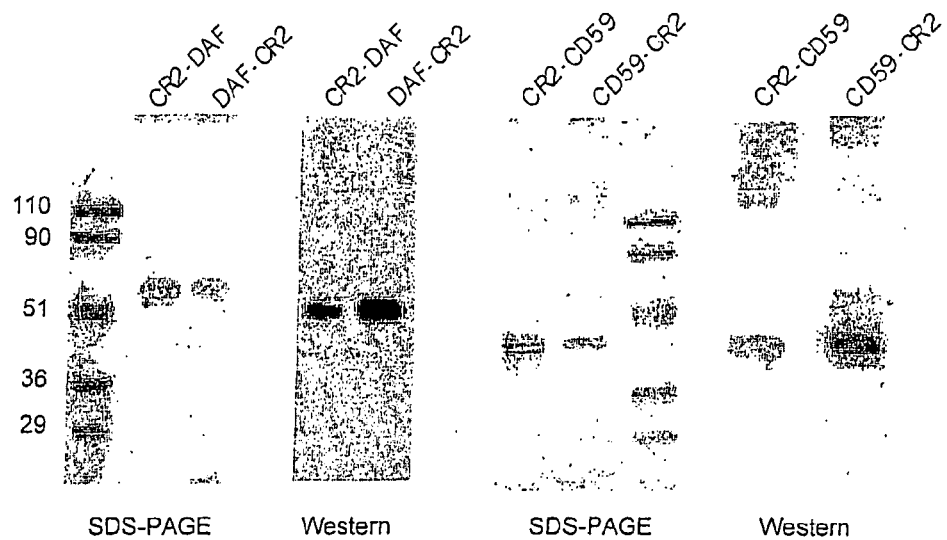

(2) Expression and Purification cDNA plasmid constructs encoding the fusion proteins were transfected into CHO cells and stably expressing clones isolated. Clones expressing highest levels of fusion protein were selected. The selected clones were grown in bioreactors and fusion proteins isolated from culture supernatant by affinity chromatography. Affinity columns were prepared using anti-DAF and anti-CD59 antibodies conjugated to sepharose. Recombinant proteins were analyzed by SDS-PAGE and Western blot (FIG. 2).

(3) Binding of Fusion Proteins to C3 Ligands.

(a) Flow Cytometry

Flow cytometry experiments were conducted as previously described. All of the CR2 containing fusion proteins bound to C3-coated CHO cells, as analyzed by flow cytometry (FIG. 12). sDAF and sCD59 did not bind to C3-coated CHO cells.

(b) ELISA

ELISA experiments were conducted as previously described. In ELISA experiments, CR2-containing constructs were added to wells coated with purified C3dg. Binding was detected by means of anti-complement inhibitor antibodies and enzyme-conjugated secondary antibodies. All CR2 containing constructs, but not sCD59 and sDAF bound to C3d.

(c) Surface Plasmon Resonance

Biotinylated C3dg (CR2 ligand) was bound to streptavidin coated BIAcore chips and binding kinetics of CR2 containing fusion proteins measured (FIGS. 13-16). sDAF and sCD59 did not bind to captured C3dg. Fusion proteins with CR2 at N-terminus bound with highest affinity. CD59 containing fusion proteins bound with higher affinity than corresponding DAF containing fusion proteins.

(4) Complement Inhibitory Function of Fusion Proteins

The functional activity of the fusion proteins and soluble untargeted complement inhibitors was analyzed by measuring the effect of the proteins on complement-mediated cell lysis. Assays using Chinese hamster ovary (CHO) cells (FIGS. 17 and 18) and sheep erythrocytes (E) (FIGS. 19 and 20) were used.

The targeted complement inhibitors provided significantly more protection from complement-mediated than soluble untargeted complement inhibitors. Fusion proteins containing CR2 at the N-terminus were the most effective for both DAF and CD59 containing fusion proteins. N-terminal CR2 fusion proteins also bound C3d with a higher affinity than C-terminal CR2 fusion proteins in BIAcore experiments (see above). CR2-DAF was significantly more effective than CR2-CD59 at providing protection from complement-mediated lysis in these assays. Of note, however, untargeted sCD59 possesses very weak complement inhibitory activity even at high concentration (unlike sDAF), and the targeting of CD59 to the cell surface is a requirement for CD59 function.

The relative effectiveness of targeted vs. untargeted complement inhibitors for CHO cells and E is different. However, erythrocytes are lysed by "one hit" (ie. formation of a single MAC causes E lysis), whereas nucleated cells (such as CHO) posses addition resistance mechanisms (such as capping and shedding of MACs) and require deposition of multiple MACs for lysis. These differences likely account for differences in lysis inhibition data, and CHO cells likely represent the more physiologically relevant target for these in vitro experiments.

D) Results—2

(1) Targeted Complement Activating Fusion/Conjugated Proteins

Human CR2-IgG1 Fc has been expressed and purified and shown to appropriately target C3 opsonized cells in vitro. Expression plasmids containing encoding sequences for human and mouse sCR2 (for conjugation with CVF) and mouse fusion proteins have been prepared. Nucleotide sequence and predicted amino acid sequences of mature human fusion proteins are shown in FIG. 21

(2) Expression and Purification cDNA encoding the first 4 SCRs of CR2 was linked to genomic sequence encoding human IgG1 Fc region. Plasmid encoding the fusion protein was transfected into CHO cells and stably expressing clones isolated. Clones expressing highest levels of fusion protein were selected. The selected clone was grown in a bioreactor and fusion proteins isolated from culture supernatant by protein A affinity chromatography. Recombinant protein was analyzed by SDS-PAGE (FIG. 22) and Western blot. Protein migrated at expected molecular weight under reducing and nonreducing conditions (CR2-Fc is disulfide linked dimer). A murine plasmid construct encoding CR2-mouse IgG3 has been constructed.

(3) Binding of Fusion Proteins to C3 Ligands.

(a) Flow Cytometry

CR2-Fc bound to C3-coated CHO cells, as analyzed by, flow cytometry (FIG. 23).

(b) ELISA

In ELISA experiments, CR2-Fc was added to wells coated with purified C3dg. Binding was detected by means of anti-human Fc antibodies and enzyme-conjugated secondary antibodies. CR2-Fc bound to C3d.

(c) Surface Plasmon Resonance

Biotinylated C3dg (CR2 ligand) was bound to streptavidin coated BIAcore chips and binding of CR2-Fc demonstrated (FIG. 24).

3. Example 3 a) Antibody Targeted Complement Inhibitors in a Rat Model of Acute Tubulointerstitial Injury:

A panel of well characterized mouse anti-rat kidney monoclonal antibodies was used (49, 50, incorporated herein by reference for their teaching regarding these antibodies and their sequences). The variable region DNA from a total of 5 antibodies was isolated by standard PCR techniques (35, incorporated herein by reference for its teachings regarding PCR). All were successfully cloned and some were expressed as single chain antibodies. All single chain antibodies recognized either a rat kidney epithelial or endothelial cell line in vitro. One of the mAbs, K9/9, binds to a glycoprotein identified on the epithelial cell surface, and has specificity for the glomerular capillary wall and proximal tubules in vivo (49). This antibody was chosen as a targeting vehicle for investigation of targeted Crry- and CD59-mediated complement inhibition in a rat model of acute tubulointerstitial injury. Although the K9/9 mAb was shown to induce glomerular damage in a previous study (49), the antibody was only pathogenic when administered together with Freunds adjuvant. In fact the pathogenic nature of K9/9 mAb (with adjuvant) was not reproduced.

There is a link between proteinuria and progressive renal damage and there is data to support the hypothesis that proteinuria itself results in interstitial fibrosis and inflammation. The mechanism by which proteinuria leads to nephrotoxic injury is not known, but there is evidence that complement plays a key role and that the MAC is the principal mediator of tubulointerstitial injury due to proteinuria. (The role of complement and proteinuria in tubulointerstitial injury has been recently reviewed (51, 52)). Previous characterization of K9/9 mAb (see above (49)) suggested that the mAb targets appropriately for an investigation into the therapeutic use of targeted complement inhibitors in a rat model tubulointerstitial injury induced by proteinuria. The availability of an inhibitor that can specifically block MAC formation would allows an assessment of the role of MAC in tubulointerstitial injury under clinically relevant conditions.

Plasmid constructs encoding single chain K9/9 antibody linked to rat Crry or rat CD59 were prepared (depicted in FIG. 27). Constructs expressing soluble rat Crry (sCrry) and single chain K9/9 (targeting vehicle only) were also prepared. All recombinant proteins were expressed into the culture medium at over 15 mg/liter by *Pichia* fermentation in a 15 liter New Brunswick fermentor.

Recombinant proteins were characterized for targeting and complement inhibitory activity in vitro as described above using a rat epithelial cell line as target cells. Single chain K9/9, K9/9-Crry and K9/9-CD59 specifically bound to rat epithelia cells in vitro. sCrry and K9/9-Crry inhibited complement deposition and lysis, and K9/9-CD59 inhibited complement-mediated lysis. Both targeted complement inhibitors, sCrry and K9/9 single chain Ab were characterized in the rat puromycin aminonucleoside (PAN) nephrosis model (53, incorporated herein by reference for its teaching of sCrry and K9/9) (sCD59 was not evaluated since untargeted CD59 has only very poor complement inhibitory activity (54)). First, to confirm kidney targeting of K9/9 fusion proteins, in vivo binding specificity was determined by biodistribution of iodinated proteins as described above (54, 41). Single chain K9/9 and K9/9 fusion proteins, but not sCrry, specifically targeted to rat kidneys and was detectable at 48 hr after administration (FIG. 28). Biodistribution at 24 hr after administration was similar, and there was no radiolabel remaining in the blood at 24 hr.

In therapeutic studies, groups of 4 rats received PAN (150 mg/kg) at day 0 and either PBS or complement inhibitor (40 mg/kg) on days 4, 7 and 10. Urine (metabolic cages) and blood was collected and animals sacrificed on day 11. PAN treatment significantly impaired renal function as measured by creatinine clearance (FIG. 29, second bar from left). There was a slight, but not significant improvement in renal function in rats receiving sCrry therapy. However, creatinine clearance was significantly improved in PAN treated rats receiving either targeted Crry or CD59 therapy (p<0.01). There was no significant difference in creatinine clearance between control (non-proteinuric) rats and PAN treated rats receiving either of the targeted inhibitors (FIG. 29). As expected, PAN-induced proteinuria was high in all rats whether treated with complement inhibitors or not (table 1). Kidney sections prepared from rats treated with PAN and receiving no therapy showed dilation of tubular lumina and tubular and epithelial cell degeneration as assessed by loss of brush border (see FIG. 30*b*, also in appendix). Minimal improvement was seen with sCrry therapy (FIG. 30*d*). In contrast tubular dilation and degeneration was significantly suppressed in PAN-treated rats receiving targeted Crry and CD59 (FIG. 30*c* shows K9/9-Crry, but histology was indistinguishable with K9/9-CD59). These data demonstrate therapeutic efficacy of complement inhibition in this model, demonstrate significant benefit of targeted vs untargeted complement inhibition and directly demonstrate an important role for MAC-mediated damage in tubulointerstial injury induced by proteinuria. sCD59 is not an effective inhibitor and this study demonstrates that appropriately targeted CD59 allows for the specific inhibition of the MAC in vivo.

In a separate experiment the circulatory half life of iodinated recombinant proteins was determined as described (54, 41, incorporated herein by reference for the techniques taught therein). The half lives (t½) of the proteins were as follows: sCrry: 19 min, K9/9-Crry: 23 min, K9/9-CD59, 29 min, single chain K9/9: 21 min. To determine the effect of the recombinant proteins on systemic complement inhibition, rats were injected with proteins at 40 mg/Kg and blood collected at times corresponding to 1, 3, 5 and 7×t½. Complement inhibitory activity in serum was determined by measuring hemolytic activity (sensitized sheep erythrocytes). As expected, K9/9-CD59 had minimal inhibitory activity in serum (untargeted assay system) (FIG. 31). By about 3 hr (7×t½) after the injection of sCrry and K9/9-Crry, there was minimal complement inhibitory activity remaining in serum. The short t½ of targeted and untargeted inhibitors, together with biodistribution data and the fact that sCrry is not protective, demonstrate that the kidney-bound complement inhibitors are effective at inhibiting complement locally and for a prolonged period.

These data establish the use of targeted complement inhibitors in vivo and demonstrate important benefits of targeted versus untargeted systemic complement inhibition in a model of disease. Although a different targeting vehicle is used in these studies (an antibody fragment), the same principles apply for other targeting vehicles, such as CR2.

4. Example 4

Disclosed herein are examples of constructs of the present invention made in accordance with the teaching herein. The terminology used has the following meaning: SCR=short consensus repeats; LP=Leader Peptide. The constructs all have the basic formula of CR2-linker-complement modulator or complement modulator-linker-CR2. Notations in parenthesis indicate details within a particular section of the composition. For example, "(complete)" means that the entire mature protein is used in the construct, whereas "(SCR2-4)" indicates that SCR1 is not part of the construct. It is understood that a linker can be a chemical linker, a natural linker peptide, or amino acid linking sequences (e.g., $(Gly_4Ser)_3$). It is understood that this list is not limiting and only provides examples of some of the constructs disclosed in the present application.

CR2 (complete)-$(Gly_4Ser)_3$--DAF
CR2 (complete)-$(Gly_4Ser)_3$-human CD59
CR2 (complete)-$(Gly_4Ser)_3$--MCP
CR2 (complete)-$(Gly_4Ser)_3$-CR1
CR2 (complete)-$(Gly_4Ser)_3$--Crry
CR2 (complete)-$(Gly_4Ser)_3$-mouse CD59
CR2 (complete)-$(Gly_4Ser)_3$-human IgG1 Fc
CR2 (complete)-$(Gly_4Ser)_3$-human IgM Fc
CR2 (complete)-$(Gly_4Ser)_3$-murine IgG3 Fc
CR2 (complete)-$(Gly_4Ser)_3$-murine IgM Fc
CR2 (complete)-$(Gly_4Ser)_3$--CVF
CR2 (complete)-$(Gly_3Ser)_4$--DAF
CR2 (complete)-$(Gly_3Ser)_4$-human CD59
CR2 (complete)-$(Gly_3Ser)_4$--MCP
CR2 (complete)-$(Gly_3Ser)_4$-CR1
CR2 (complete)-$(Gly_3Ser)_4$--Crry
CR2 (complete)-$(Gly_3Ser)_4$-mouse CD59
CR2 (complete)-$(Gly_3Ser)_4$-human IgG1 Fc
CR2 (complete)-$(Gly_3Ser)_4$-human IgM Fc
CR2 (complete)-$(Gly_3Ser)_4$-murine IgG3 Fc CR2 (complete)-(Gly$_3$Ser)$_4$-murine IgM Fc
CR2 (complete)-(Gly$_3$Ser)$_4$-CVF
CR2 (complete)-(Gly$_4$Ser)$_3$-DAF (SCRs 2-4)
CR2 (complete)-(Gly$_3$Ser)$_4$-DAF (SCRs 2-4)
CR2 (complete)-(Gly$_4$Ser)$_3$-CR1 (LP--SCR1-4-SCR8-11-SCR15-18)
CR2 (complete)-(Gly$_4$Ser)$_3$-Crry (5 N-terminal SCRs)
CR2 (complete)-VSVFPLE--DAF
CR2 (complete)-VSVFPLE--human CD59
CR2 (complete)-VSVFPLE--MCP
CR2 (complete)-VSVFPLE-CR1
CR2 (complete)-VSVFPLE--Crry
CR2 (complete)-VSVFPLE-mouse CD59
CR2 (complete)-VSVFPLE-human IgG1 Fc
CR2 (complete)-VSVFPLE-human IgM Fc
CR2 (complete)-VSVFPLE-murine IgG3 Fc
CR2 (complete)-VSVFPLE-murine IgM Fc
CR2 (complete)-VSVFPLE-CVF
CR2 (complete)---m-Maleimidobenzoyl-N-hydroxysuccinimide ester--DAF
CR2 (complete)---m-Maleimidobenzoyl-N-hydroxysuccinimide ester-human CD59
CR2 (complete)-m-Maleimidobenzoyl-N-hydroxysuccinimide ester--MCP
CR2 (complete)-m-Maleimidobenzoyl-N-hydroxysuccinimide ester-CR1
CR2 (complete)-m-Maleimidobenzoyl-N-hydroxysuccinimide ester--Crry
CR2 (complete)-m-Maleimidobenzoyl-N-hydroxysuccinimide ester-mouse CD59
CR2 (complete)-m-Maleimidobenzoyl-N-hydroxysuccinimide ester-human IgG1 Fc
CR2 (complete)-m-Maleimidobenzoyl-N-hydroxysuccinimide ester-human IgM Fc
CR2 (complete)-m-Maleimidobenzoyl-N-hydroxysuccinimide ester-murine IgG3 Fc
CR2 (complete)-m-Maleimidobenzoyl-N-hydroxysuccinimide ester-murine IgM Fc
CR2 (complete)-m-Maleimidobenzoyl-N-hydroxysuccinimide ester-CVF
CR2 (complete)-bismaleimidohexane--DAF
CR2 (complete)-bismaleimidohexane-human CD59
CR2 (complete)-bismaleimidohexane--MCP
CR2 (complete)-bismaleimidohexane-CR1
CR2 (complete)-bismaleimidohexane--Crry
CR2 (complete)-bismaleimidohexane-mouse CD59
CR2 (complete)-bismaleimidohexane-human IgG1 Fc
CR2 (complete)-bismaleimidohexane-human IgM Fc
CR2 (complete)-bismaleimidohexane-murine IgG3 Fc
CR2 (complete)-bismaleimidohexane-murine IgM Fc
CR2 (complete)-bismaleimidohexane-CVF
CR2 (SCR1-2)-(Gly$_4$Ser)$_3$--DAF
CR2 (SCR1-2)-(Gly$_4$Ser)$_3$-human CD59
CR2 (SCR1-2)-(Gly$_4$Ser)$_3$--MCP
CR2 (SCR1-2)-(Gly$_4$Ser)$_3$-CR1
CR2 (SCR1-2)-(Gly$_4$Ser)$_3$--Crry
CR2 (SCR1-2)-(Gly$_4$Ser)$_3$-mouse CD59
CR2 (SCR1-2)-(Gly$_4$Ser)$_3$-human IgG1 Fc
CR2 (SCR1-2)-(Gly$_4$Ser)$_3$-human IgM Fc
CR2 (SCR1-2)-(Gly$_4$Ser)$_3$-murine IgG3 Fc
CR2 (SCR1-2)-(Gly$_4$Ser)$_3$-murine IgM Fc
CR2 (SCR1-2)-(Gly$_4$Ser)$_3$--CVF
CR2 (SCR1-2)-(Gly$_3$Ser)$_4$--DAF
CR2 (SCR1-2)-(Gly$_3$Ser)$_4$-human CD59
CR2 (SCR1-2) (Gly$_3$Ser)$_4$--MCP
CR2 (SCR1-2)-(Gly$_3$Ser)$_4$-CR1
CR2 (SCR1-2)-(Gly$_3$Ser)$_4$--Crry
CR2 (SCR1-2)-(Gly$_3$Ser)$_4$-mouse CD59
CR2 (SCR1-2)-(Gly$_3$Ser)$_4$-human IgG1 Fc
CR2 (SCR1-2)-(Gly$_3$Ser)$_4$-human IgM Fc
CR2 (SCR1-2)-(Gly$_3$Ser)$_4$-murine IgG3 Fc
CR2 (SCR1-2)-(Gly$_3$Ser)$_4$-murine IgM Fc
CR2 (SCR1-2)-(Gly$_3$Ser)$_4$-CVF
CR2 (SCR1-2)-(Gly$_4$Ser)$_3$-DAF (SCRs 2-4)
CR2 (SCR1-2)-(Gly$_3$Ser)$_4$-DAF (SCRs 2-4)
CR2 (SCR1-2)-(Gly$_4$Ser)$_3$-CR1 (LP--SCR1-4-SCR8-11-SCR15-18)
CR2 (SCR1-2)-(Gly$_4$Ser)$_3$-Crry (5 N-terminal SCRs)
CR2 (SCR1-2)-VSVFPLE--DAF
CR2 (SCR1-2)-VSVFPLE-human CD59
CR2 (SCR1-2)-VSVFPLE--MCP
CR2 (SCR1-2)-VSVFPLE-CR1
CR2 (SCR1-2)-VSVFPLE--Crry
CR2 (SCR1-2)-VSVFPLE-mouse CD59
CR2 (SCR1-2)-VSVFPLE-human IgG1 Fc
CR2 (SCR1-2)-VSVFPLE-human IgM Fc
CR2 (SCR1-2)-VSVFPLE-murine IgG3 Fc
CR2 (SCR1-2)-VSVFPLE-murine IgM Fc
CR2 (SCR1-2)-VSVFPLE-CVF
CR2 (SCR1-2)---m-Maleimidobenzoyl-N-hydroxysuccinimide ester--DAF
CR2 (SCR1-2)---m-Maleimidobenzoyl-N-hydroxysuccinimide ester-human CD59
CR2 (SCR1-2)---m-Maleimidobenzoyl-N-hydroxysuccinimide ester--MCP
CR2 (SCR1-2)-m-Maleimidobenzoyl-N-hydroxysuccinimide ester-CR1
CR2 (SCR1-2)-m-Maleimidobenzoyl-N-hydroxysuccinimide ester--Crry
CR2 (SCR1-2)-m-Maleimidobenzoyl-N-hydroxysuccinimide ester-mouse CD59
CR2 (SCR1-2)-m-Maleimidobenzoyl-N-hydroxysuccinimide ester-human IgG1 Fc
CR2 (SCR1-2)-m-Maleimidobenzoyl-N-hydroxysuccinimide ester-human IgM Fc
CR2 (SCR1-2) m-Maleimidobenzoyl-N-hydroxysuccinimide ester-murine IgG3 Fc
CR2 (SCR1-2)-m-Maleimidobenzoyl-N-hydroxysuccinimide ester-murine IgM Fc
CR2 (SCR1-2)-m-Maleimidobenzoyl-N-hydroxysuccinimide ester-CVF
CR2 (SCR1-2)-bismaleimidohexane--DAF
CR2 (SCR1-2)-bismaleimidohexane-human CD59
CR2 (SCR1-2)-bismaleimidohexane--MCP
CR2 (SCR1-2)-bismaleimidohexane-CR1
CR2 (SCR1-2)-bismaleimidohexane--Crry
CR2 (SCR1-2)-bismaleimidohexane-mouse CD59
CR2 (SCR1-2)-bismaleimidohexane-human IgG1 Fc
CR2 (SCR1-2)-bismaleimidohexane-human IgM Fe
CR2 (SCR1-2)-bismaleimidohexane-murine IgG3 Fc
CR2 (SCR1-2)-bismaleimidohexane-murine IgM Fc
CR2 (SCR1-2)-bismaleimidohexane-CVF
CR2 (SCR1-3)-(Gly$_4$Ser)$_3$--DAF
CR2 (SCR1-3)-(Gly$_4$Ser)$_3$-human CD59
CR2 (SCR1-3)-(Gly$_4$Ser)$_3$--MCP
CR2 (SCR1-3)-(Gly$_4$Ser)$_3$-CR1
CR2 (SCR1-3)-(Gly$_4$Ser)$_3$--Crry
CR2 (SCR1-3)-(Gly$_4$Ser)$_3$-mouse CD59
CR2 (SCR1-3)-(Gly$_4$Ser)$_3$-human IgG1 Fc
CR2 (SCR1-3)-(Gly$_4$Ser)$_3$-human IgM Fe
CR2 (SCR1-3)-(Gly$_4$Ser)$_3$-murine IgG3 Fc
CR2 (SCR1-3)-(Gly$_4$Ser)$_3$-murine IgM Fc
CR2 (SCR1-3)-(Gly$_4$Ser)$_3$--CVF
CR2 (SCR1-3)-(Gly$_3$Ser)$_4$--DAF CR2 (SCR1-3)-(Gly$_3$Ser)$_4$-human CD59
CR2 (SCR1-3)-(Gly$_3$Ser)$_4$--MCP
CR2 (SCR1-3)-(Gly$_3$Ser)$_4$-CR1
CR2 (SCR1-3)-(Gly$_3$Ser)$_4$--Crry
CR2 (SCR1-3)-(Gly$_3$Ser)$_4$-mouse CD59
CR2 (SCR1-3)-(Gly$_3$Ser)$_4$-human IgG1 Fc
CR2 (SCR1-3)-(Gly$_3$Ser)$_4$-human IgM Fc
CR2 (SCR1-3)-(Gly$_3$Ser)$_4$-murine IgG3 Fc
CR2 (SCR1-3)-(Gly$_3$Ser)$_4$-murine IgM Fc
CR2 (SCR1-3)-(Gly$_3$Ser)$_4$-CVF
CR2 (SCR1-3)-(Gly$_4$Ser)$_3$-DAF (SCRs 2-4)
CR2 (SCR1-3)-(Gly$_4$Ser)$_3$-DAF (SCRs 2-4)
CR2 (SCR1-3)-(Gly$_4$Ser)$_3$-CR1 (LP--SCR1-4-SCR8-11-SCR15-18)
CR2 (SCR1-3)-(Gly$_4$Ser)$_3$-Crry (5 N-terminal SCRs)
CR2 (SCR1-3)-VSVFPLE--DAF
CR2 (SCR1-3)-VSVFPLE-human CD59
CR2 (SCR1-3)-VSVFPLE--MCP
CR2 (SCR1-3)-VSVFPLE-CR1
CR2 (SCR1-3)-VSVFPLE--Crry
CR2 (SCR1-3)-VSVFPLE-mouse CD59
CR2 (SCR1-3)-VSVFPLE-human IgG1 Fc
CR2 (SCR1-3)-VSVFPLE-human IgM Fc
CR2 (SCR1-3)-VSVFPLE-murine IgG3 Fc
CR2 (SCR1-3)-VSVFPLE-murine IgM Fc
CR2 (SCR1-3)-VSVFPLE-CVF
CR2 (SCR1-3)---m-Maleimidobenzoyl-N-hydroxysuccinimide ester--DAF
CR2 (SCR1-3)---m-Maleimidobenzoyl-N-hydroxysuccinimide ester-human CD59
CR2 (SCR1-3)-m-Maleimidobenzoyl-N-hydroxysuccinimide ester--MCP
CR2 (SCR1-3)-m-Maleimidobenzoyl-N-hydroxysuccinimide ester-CR1
CR2 (SCR1-3)-m-Maleimidobenzoyl-N-hydroxysuccinimide ester--Crry
CR2 (SCR1-3)-m-Maleimidobenzoyl-N-hydroxysuccinimide ester-mouse CD59
CR2 (SCR1-3)-m-Maleimidobenzoyl-N-hydroxysuccinimide ester-human IgG1 Fc
CR2 (SCR1-3)-m-Maleimidobenzoyl-N-hydroxysuccinimide ester-human IgM Fc
CR2 (SCR1-3)-m-Maleimidobenzoyl-N-hydroxysuccinimide ester-murine IgG3 Fc
CR2 (SCR1-3)-m-Maleimidobenzoyl-N-hydroxysuccinimide ester-murine IgM Fc
CR2 (SCR1-3)-m-Maleimidobenzoyl-N-hydroxysuccinimide ester-CVF
CR2 (SCR1-3)-bismaleimidohexane--DAF
CR2 (SCR1-3)-bismaleimidohexane-human CD59
CR2 (SCR1-3)-bismaleimidohexane--MCP
CR2 (SCR1-3)-bismaleimidohexane-CR1
CR2 (SCR1-3)-bismaleimidohexane--Crry
CR2 (SCR1-3)-bismaleimidohexane-mouse CD59
CR2 (SCR1-3)-bismaleimidohexane-human IgG1 Fc
CR2 (SCR1-3) bismaleimidohexane-human IgM Fc
CR2 (SCR1-3)-bismaleimidohexane-murine IgG3 Fc
CR2 (SCR1-3)-bismaleimidohexane-murine IgM Fc
CR2 (SCR1-3)-bismaleimidohexane-CVF
CR2 (SCR1-4)-(Gly$_4$Ser)$_3$-DAF
CR2 (SCR1-4)-(Gly$_4$Ser)$_3$-human CD59
CR2 (SCR1-4)-(Gly$_4$Ser)$_3$--MCP
CR2 (SCR1-4)-(Gly$_4$Ser)$_3$-CR1
CR2 (SCR1-4)-(Gly$_4$Ser)$_3$--Crry
CR2 (SCR1-4)-(Gly$_4$Ser)$_3$-mouse CD59
CR2 (SCR1-4)-(Gly$_4$Ser)$_3$-human IgG1 Fc
CR2 (SCR1-4)-(Gly$_4$Ser)$_3$-human IgM Fc
CR2 (SCR1-4)-(Gly$_4$Ser)$_3$-murine IgG3 Fc
CR2 (SCR1-4)-(Gly$_4$Ser)$_3$-murine IgM Fc
CR2 (SCR1-4)-(Gly$_4$Ser)$_3$--CVF
CR2 (SCR1-4)-(Gly$_4$Ser)$_3$--DAF
CR2 (SCR1-4)-(Gly$_3$Ser)$_4$-human CD59
CR2 (SCR1-4)-(Gly$_3$Ser)$_4$--MCP
CR2 (SCR1-4)-(Gly$_3$Ser)$_4$-CR1
CR2 (SCR1-4)-(Gly$_3$Ser)$_4$--Crry
CR2 (SCR1-4)-(Gly$_3$Ser)$_4$-mouse CD59
CR2 (SCR1-4)-(Gly$_3$Ser)$_4$-human IgG1 Fc
CR2 (SCR1-4)-(Gly$_3$Ser)$_4$-human IgM Fc
CR2 (SCR1-4)-(Gly$_3$Ser)$_4$-murine IgG3 Fc
CR2 (SCR1-4)-(Gly$_3$Ser)$_4$-murine IgM Fe
CR2 (SCR1-4)-(Gly$_3$Ser)$_4$-CVF
CR2 (SCR1-4)-(Gly$_4$Ser)$_3$-DAF (SCRs 2-4)
CR2 (SCR1-4)-(Gly$_3$Ser)$_4$-DAF (SCRs 2-4)
CR2 (SCR1-4)-(Gly$_4$Ser)$_3$-CR1 (LP--SCR1-4-SCR8-11-SCR15-18)
CR2 (SCR1-4)-(Gly$_4$Ser)$_3$-Crry (5 N-terminal SCRs)
CR2 (SCR1-4)-VSVFPLE--DAF
CR2 (SCR1-4)-VSVFPLE-human CD59
CR2 (SCR1-4)-VSVFPLE--MCP
CR2 (SCR1-4)-VSVFPLE-CR1
CR2 (SCR1-4)-VSVFPLE--Crry
CR2 (SCR1-4)-VSVFPLE-mouse CD59
CR2 (SCR1-4)-VSVFPLE-human IgG1 Fc
CR2 (SCR1-4)-VSVFPLE-human IgM Fc
CR2 (SCR1-4) VSVFPLE-murine IgG3 Fc
CR2 (SCR1-4)-VSVFPLE-murine IgM Fc
CR2 (SCR1-4)-VSVFPLE-CVF
CR2 (SCR1-4)-m-Maleimidobenzoyl-N-hydroxysuccinimide ester--DAF
CR2 (SCR1-4)-m-Maleimidobenzoyl-N-hydroxysuccinimide ester-human CD59
CR2 (SCR1-4)-m-Maleimidobenzoyl-N-hydroxysuccinimide ester--MCP
CR2 (SCR1-4)-m-Maleimidobenzoyl-N-hydroxysuccinimide ester-CR1
CR2 (SCR1-4)-m-Maleimidobenzoyl-N-hydroxysuccinimide ester--Crry
CR2 (SCR1-4)-m-Maleimidobenzoyl-N-hydroxysuccinimide ester-mouse CD59
CR2 (SCR1-4)-m-Maleimidobenzoyl-N-hydroxysuccinimide ester-human IgG1 Fc
CR2 (SCR1-4)-m-Maleimidobenzoyl-N-hydroxysuccinimide ester-human IgM Fc
CR2 (SCR1-4)-m-Maleimidobenzoyl-N-hydroxysuccinimide ester-murine IgG3 Fc
CR2 (SCR1-4)-m-Maleimidobenzoyl-N-hydroxysuccinimide ester-murine IgM Fc
CR2 (SCR1-4)-m-Maleimidobenzoyl-N-hydroxysuccinimide ester
CR2 (SCR1-4)-bismaleimidohexane--DAF
CR2 (SCR1-4)-bismaleimidohexane-human CD59
CR2 (SCR1-4)-bismaleimidohexane--MCP
CR2 (SCR1-4)-bismaleimidohexane-CR1
CR2 (SCR1-4)-bismaleimidohexane--Crry
CR2 (SCR1-4)-bismaleimidohexane-mouse CD59
CR2 (SCR1-4)-bismaleimidohexane-human IgG1 Fc
CR2 (SCR1-4)-bismaleimidohexane-human IgM Fc
CR2 (SCR1-4)-bismaleimidohexane-murine IgG3 Fc
CR2 (SCR1-4)-bismaleimidohexane-murine IgM Fc
CR2 (SCR1-4)-bismaleimidohexane-CVF

G. REFERENCES

1. Wang, Y., Rollins, S. A., Madri, J. A., and Matis, L. A. 1995. Anti-C5 monoclonal antibody therapy prevents collagen-induced arthritis and ameliorates established disease. *Proc Natl Acad Sci USA* 92:8955-8959.
2. Wang, Y., Hu, Q., Madri, J. A., Rollins, S. A., Chodera, A., and Matis, L. A. 1996. Amelioration of lupus-like autoimmune disease in NZB/W F1 mice after treatment with a blocking monoclonal antibody specific for complement component C5. *Proc. Natl. Acad. Sci. USA* 93:8563-8568.
3. Kaplan, M. 2002. Eculizumab (Alexion). *Curr Opin Investig Drugs* 3:1017-1023.
4. Whiss, P. A. 2002. Pexelizumab Alexion. *Curr Opin Investig Drugs* 3:870-877.
5. Weisman, H. F., Bartow, T., Leppo, M. K., Marsh, H. C., Carson, G. R., Consino, M. F., Boyle, M. P., Roux, K. H., Weisfeldt, M. L., and Fearon, D. T. 1990. Soluble human complement receptor type 1: in vivo inhibitor of complement suppressing post-ischenic myocardial inflammation and necrosis. Science 249:146-151.
6. Rioux, P. 2001. TP-10 (AVANT Immunotherapeutics). *Curr Opin Investig Drugs* 2:364-371.
7. Higgins, P. J., Ko, J.-L., Lobell, R., Sardonini, C., Alessi, M. K., and Yeh, C. G. 1997. A soluble chimeric complement activating inhibitory protein that possesses both decay-accelerating and factor I cofactor activities. *J. Immunol.* 158:2872-2881.
8. Moran, P., Beasly, H., Gorrel, A., Martin, E., Gribling, P., Fuchs, H., Gillet, N., Burton, L. E., and Caras, I. W. 1992. Human recombinant soluble decay accelerating factor inhibits complement activation in vitro and in vivo. *J. Immunol.* 149:1736-1743.
9. Christiansen, D., Milland, J., Thorley, B. R., McKenzie, I. F., and Loveland, B. E.
1996. A functional analysis of recombinant soluble CD46 in vivo and a comparison with recombinant soluble forms of CD55 and CD35 in vitro. *eji* 26:578-585.
10. Salerno, C. T., Kulick, D. M., Yeh, C. G., Guzman-Paz, M., Higgins, P. J., Benson, B. A., Park, S. J., Shumway, S. J., Bolman, R. M., 3rd, and Dalmasso, A. P. 2002. A soluble chimeric inhibitor of C3 and C5 convertases, complement activation blocker-2, prolongs graft survival in pig-to-rhesus monkey heart transplantation. *Xenotransplantation* 9:125-134.
11. Kroshus, T. J., Salerno, C. T., Yeh, C. G., Higgins, P. J., Bolman, R. M., 3rd, and Dalmasso, A. P. 2000. A recombinant soluble chimeric complement inhibitor composed of human CD46 and CD55 reduces acute cardiac tissue injury in models of pig-to-human heart transplantation. *Transplantation* 69:2282-2289.
12. Rushmere, N. K., Van Den Berg, C. W., and Morgan, B. P. 2000. Production and functional characterization of a soluble recombinant form of mouse CD59. *Immunology* 99:326-332.
13. Quigg, R. J., He, C., Hack, B. K., Alexander, J. J., and Morgan, B. P. 2000. Production and functional analysis of rat CD59 and chimeric CD59-Crry as active soluble proteins in *Pichia pastoris*. *Immunology* 99:46-53.
14. Sugita, Y., Ito, K., Shiozuka, K., Gushima, H., Tomita, M., and Masuho, Y. 1994. Recombinant soluble CD59 inhibits reactive haemolysis with complement. *Immunol.* 82:34-41.
15. Meri, S., Lehto, T., Sutton, C. W., Tyynela, J., and Baumann, M. 1996. Structural composition and functional characterization of soluble CD59: heterogeneity of the oligosaccharide and glycophosphoinositol (GPI) anchor revealed by laser-desorption mass spectrometric analysis. *Biochem J* 316 (Pt 3):923-935.
16. Mulligan, M. S., Warner, R. L., Ritterhaus, C. W., Thomas, L. J., Ryan, U.S., Foreman, K. E., Crouch, L. D., Till, G. O., and Ward, P. A. 1999. Endothelial targeting and enhanced antiinflammatory effects of complement inhibitors possessing silayl lewisX moieties. *J. Immunol.* 162:4952-4959.
17. Ritterhaus, C. W., Thomas, L. J., Miller, D. P., Picard, M. D., Georhegan-Barek, K. M., Scesney, S. M., Henry, L. D., Sen, A. C., Bertino, A. M., Hannig, G., et al. 1999. Recombinant glycoproteins that inhibit complement activation and also bind the selectin adhesion molecules. *J. Biol. Chem.* 274:11237-11244.
18. Zhang H f, H., Lu, S., Morrison, S. L., and Tomlinson, S. 2001. Targeting of functional antibody-decay accelerating factor (DAF) fusion proteins to a cell surface. *J Biol Chem* 14:14.
19. Zhang, H.-F., Yu, J., Bajwa, E., Morrison, S. L., and Tomlinson, S. 1999. Targeting of functional antibody-CD59 fusion proteins to a cell surface. *J. Clin. Invest.* 103:55-66.
20. Linton, S. M., Williams, A. S., Dodd, I., Smith, R., Williams, B. D., and Morgan, B. P. 2000. Therapeutic efficacy of a novel membrane-targeted complement regulator in antigen-induced arthritis in the rat. *Arthritis Rheum* 43:2590-2597.
21. Smith, G. P., and Smith, R. A. 2001. Membrane-targeted complement inhibitors. *Mol Immunol* 38:249-255.
22. Carroll, M. C. 1998. The role of complement and complement receptors in induction and regulation of immunity. *Annu. Rev. Immunol.* 16:545-568.
23. Carroll, M. C. 2000. The role of complement in B cell activation and tolerance. *Adv Immunol* 74:61-88.
24. Holers, V. M. 1989. Complement receptors. *Year Immunol* 4:231-240.
25. Dierich, M. P., Schulz, T. F., Eigentler, A., Huemer, H., and Schwable, W. 1988. Structural and functional relationships among receptors and regulators of the complement system. *Mol Immunol* 25:1043-1051.
26. Lowell, C. A., Klickstein, L. B., Carter, R. H., Mitchell, J. A., Fearon, D. T., and Ahearn, J. M. 1989. Mapping of the Epstein-Barr virus and C3dg binding sites to a common domain on complement receptor type 2. *J Exp Med* 170:1931-1946.
27. Szakonyi, G., Guthridge, J. M., Li, D., Young, K., Holers, V. M., and Chen, X. S. 2001. Structure of complement receptor 2 in complex with its C3d ligand. *Science* 292:1725-1728.
28. Law, S. K., Fearon, D. T., and Levine, R. P. 1979. Action of the C3b-inactivator on the cell-bound C3b. *J Immunol* 122:759-765.
29. Seya, T., and Nagasawa, S. 1985. Limited proteolysis of complement protein C3b by regulatory enzyme C3b inactivator: isolation and characterization of a biologically active fragment, C3d, g. *J Biochem (Tokyo)* 97:373-382.
30. Quigg, R. A., Kozono, Y., Berthiaume, D., Lim, A., Salant, J., Weinfeld, A., Griffin, P., Kremmer, E., and Holers, V. M. 1998. Blockade of antibody-induced glomerulonephritis with Crry-Ig, a soluble murine complement inhibitor. *J. Immunol.* 160:4553-4560.
31. Harlow, E., and Lane, D. 1988. *Antibodies: A laboratory manual*. New York: Cold Spring Harbor Laboratory.
32. Kim, S. 1993. Liposomes as carriers of cancer chemotherapy. Current sataus and future prospects. *Drugs* 46:618-638.
33. Davies, A., Simmons, D. L., Hale, G., Harrison, R. A., Tighe, H., Lachmann, P. J., and Waldmann, H. 1989. CD59, an Ly-6 protein expressed in human lymphoid cells, regulates the action of the complement membrane attack complex of homologous cells. *Journal of Experimental Medicine* 170:637-654.
34. Guthridge, J. M., Young, K., Gipson, M. G., Sarrias, M. R., Szakonyi, G., Chen, X. S., Malaspina, A., Donoghue, E., James, J. A., Lambris, J. D., et al. 2001. Epitope mapping using the X-ray crystallographic structure of complement receptor type 2 (CR2)/CD21: identification of a highly inhibitory monoclonal antibody that directly recognizes the CR2-C3d interface. *J Immunol* 167:5758-5766.
35. 1995. *PCR Primer. A laboratory manual*. Cold Spring Harbor: Cold Spring Harbor Laboratory Press.
36. Guthridge, J. M., Rakstang, J. K., Young, K. A., Hinshelwood, J., Aslam, M., Robertson, A., Gipson, M. G., Sarrias, M. R., Moore, W. T., Meagher, M., et al. 2001. Structural studies in solution of the recombinant N-terminal pair of short consensus/complement repeat domains of complement receptor type 2 (CR2/CD21) and interactions with its ligand C3dg. *Biochemistry* 40:5931-5941.
37. Yu, J., Caragine, T., Chen, S., Morgan, B. P., Frey, A. F., and Tomlinson, S. 1999. Protection of human breast cancer cells from complement-mediated lysis by expression of heterologous CD59. *Clin. Exp. Immunol.* 115:13-18.
38. Duits, A. J., Jainandunsing, S. M., van de Winkel, J. G., and Capel, P. J. 1991. Selective enhancement of Leu-CAM expression by interleukin 6 during differentiation of human promonocytic U937 cells. *Scand J Immunol* 33:151-159.
39. Rothlein, R., and Springer, T. A. 1986. The requirement for lymphocyte function-associated antigen 1 in homotypic leukocyte adhesion stimulated by phorbol ester. *J Exp Med* 163:1132-1149.
40. Ross, G. D., Reed, W., Dalzell, J. G., Becker, S. E., and Hogg, N. 1992. Macrophage cytoskeleton association with CR3 and CR4 regulates receptor mobility and phagocytosis of iC3b-opsonized erythrocytes. *J Leukoc Biol* 51:109-117.
41. Sharkey, R. M., Motta-Hennessy, C., Pawlyk, D., Siegel, J. A., and Goldenberg, D. M. 1990. Biodistribution and dose estimates for yttrium and iodine labeled monoclonal antibody IgG and fragments in nude in nude mice bearing human colonic tumor xenografts. *Cancer Res.* 50:2330-2336.
42. Sharkey, R. M., Natale, A., Goldenberg, D. M., and Mattes, M. J. 1991. Rapid blood clearance of immunoglobulin G2a and immunoglobulin G2b in nude mice. *Cancer Res* 51:3102-3107.
43. Andrews, B. S., Eisenberg, R. A., Theofilopoulos, A. N., Izui, S., Wilson, C. B., McConahey, P. J., Murphy, E. D., Roths, J. B., and Dixon, F. J. 1978. Spontaneous murine lupus-like syndromes. Clinical and immunopathological manifestations in several strains. *J Exp Med* 148:1198-1215.
44. Hebell, T., Ahearn, J. M., and Fearon, D. T. 1991. Suppression of the immune response by a soluble complement receptor of B lymphocytes. *Science* 254:102-105.
45. Aslam, M., and Perkins, S. J. 2001. Folded-back solution structure of monomeric factor H of human complement by synchrotron X-ray and neutron scattering, analytical ultracentrifugation and constrained molecular modelling. *J Mol Biol* 309:1117-1138.
46. Koski, C. L., Ramm, L. E., Hammer, C. H., Mayer, M. M., and Shin, M. L. 1983. Cytolysis of nucleated cells by complement: cell death displays multi-hit characteristics. *Proc Natl Acad Sci USA* 80:3816-3820.
47. Ramm, L. E., Whitlow, M. B., and Mayer, M. M. 1982. Transmembrane channel formation by complement: functional analysis of the number of C5b6, C7, C8, and C9 molecules required for a single channel. *Proc Natl Acad Sci USA* 79:4751-4755.
48. Takeda, J., Kozono, H., Takata, Y., Hong, K., Kinoshita, T., Sayama, K., Tanaka, E., and Inoue, K. 1986. Number of hits necessary for complement-mediated hemolysis. *Microbiol Immunol* 30:461-468.
49. Mendrick, D. L., and H. G. Rennke. 1988. Induction of proteinuria in the rat by a monoclonal antibody against SGP-115/107. *Kidney Int* 33:818-830.
50. Mendrick, D. L., H. G. Rennke, R. S. Cotran, T. A. Springer, and A. K. Abbas. 1983. Monoclonal antibodies against rat glomerular antigens: production and specificity. *Laboratory Investigation* 49:107-117.
51. Hsu, S. I., and W. G. Couser. 2003. Chronic progression of tubulointerstitial damage in proteinuric renal disease is mediated by complement activation: a therapeutic role for complement inhibitors? *J Am Soc Nephrol* 14:S186-191.
52. Sheerin, N. S., and S. H. Sacks. 2002. Leaked protein and interstitial damage in the kidney: is complement the missing link? *Clin Exp Immunol* 130:1-3.
53. Hori, Y., K. Yamada, N. Hanafusa, T. Okuda, N. Okada, T. Miyata, W. G. Couser, K. Kurokawa, T. Fujita, and M. Nangaku. 1999. Crry, a complement regulatory protein, modulates renal interstitial disease induced by proteinuria. *Kidney Int* 56:2096-2106.
54. Song, H., C. He, C. Knaak, J. M. Guthridge, V. M. Holers, and S. Tomlinson. 2003. Complement receptor 2-mediated targeting of complement inhibitors to sites of complement activation. *J Clin Invest* 111:1875-1885.

H. SEQUENCES

1. DAF
Nucleotide Sequence corresponds to SEQ ID NO: 1
Amino Acid Sequence corresponds to SEQ ID NO: 2
2. CD59
Nucleotide Sequence corresponds to SEQ ID NO: 3
Amino Acid Sequence corresponds to SEQ ID NO: 4
3. CR2-DAF
Nucleotide Sequence corresponds to SEQ ID NO: 5
Amino Acid Sequence corresponds to SEQ ID NO: 6
4. CR2-Human CD59
Nucleotide Sequence corresponds to SEQ ID NO: 7
Amino Acid Sequence corresponds to SEQ ID NO: 8
5. DAF-CR2
Nucleotide Sequence corresponds to SEQ ID NO: 9
Amino Acid Sequence corresponds to SEQ ID NO: 10
6. Human CD59-CR2
Nucleotide Sequence corresponds to SEQ ID NO: 11
Amino Acid Sequence corresponds to SEQ ID NO: 12
7. CR1
Nucleotide Sequence corresponds to SEQ ID NO: 13
Amino Acid Sequence corresponds to SEQ ID NO: 14
8. MCP
Nucleotide Sequence corresponds to SEQ ID NO: 15
Amino Acid Sequence corresponds to SEQ ID NO: 16
9. Mouse Crry
Amino Acid Sequence corresponds to SEQ ID NO: 17
10. Human IgG1 Fc
Amino Acid Sequence corresponds to SEQ ID NO: 18
11. Human IgM Fe
Amino Acid Sequence corresponds to SEQ ID NO: 19
12. CR2-Human IgG1 Fc
Nucleotide Sequence corresponds to SEQ ID NO: 20
Amino Acid Sequence corresponds to SEQ ID NO: 21

13. Mouse IgG3 Fc
Amino Acid Sequence corresponds to SEQ ID NO: 22
14. Cobra Venom Factor
Nucleotide Sequence corresponds to SEQ ID NO: 23
Amino Acid Sequence corresponds to SEQ ID NO: 24
15. Human CR2
Nucleotide Sequence corresponds to SEQ ID NO: 25
Amino Acid Sequence corresponds to SEQ ID NO: 26
16. Mouse CR2
Nucleotide Sequence corresponds to SEQ ID NO: 27
Amino Acid Sequence corresponds to SEQ ID NO: 28
17. Human CR2
Amino Acid Sequence corresponds to SEQ ID NO: 29

What is claimed is:

1. A composition comprising a construct, wherein the construct is a fusion protein consisting of:
    (a) a complement receptor 2 (CR2) or a fragment thereof, wherein the fragment consists of at least the first two N-terminal short consensus repeat (SCR) domains of the CR2 protein;
    (b) a modulator of complement activity, wherein the modulator consists of one or more active sites of CR1; and
    (c) optionally, a linker linking (a) and (b).

2. The composition of claim 1, wherein the sequence of the modulator consists of SEQ ID NO. 14.

3. The composition of claim 1, wherein the modulator consists of murine CR1 or human CR1.

4. The composition of claim 1, wherein the CR2 or fragment thereof is fused to the N-terminus of the modulator.

5. The composition of claim 1, wherein the CR2 or fragment thereof is fused to the C-terminus of the modulator.

6. The composition of claim 1, wherein the CR2 is a full-length CR2 protein.

7. The composition of claim 1, wherein the CR2 or fragment thereof consists of the four N-terminal SCR domains of the CR2 protein.

8. The composition of claim 1, wherein the modulator consists of the entire extracellular region of CR1.

9. The composition of claim 1, wherein at least one of the one or more active sites of CR1 consists of a leader peptide, wherein the sequence of the leader peptide consists of amino acids 6-46 of SEQ ID NO:14.

10. The composition of claim 1, wherein said modulator consists of SCR1-4 of CR1.

11. The composition of claim 1, wherein said modulator consists of SCR8-11 of CR1.

12. The composition of claim 1, wherein said modulator consists of SCR15-18 of CR1.

13. The composition of claim 1, wherein at least one of the one or more active sites of CR1 consists of the C1q binding site of CR1.

* * * * *

SEQUENCE LISTING

<160> NUMBER OF SEQ ID NOS: 29

<210> SEQ ID NO 1
<211> LENGTH: 1041
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 1
gactgtggcc ttcccccaga tgtacctaat gcccagccag ctttggaagg ccgtacaagt      60
tttcccgagg atactgtaat aacgtacaaa tgtgaagaaa gctttgtgaa aattcctggc     120
gagaaggact cagtgatctg ccttaagggc agtcaatggt cagatattga agagttctgc     180
aatcgtagct gcgaggtgcc aacaaggcta aattctgcat ccctcaaaca gccttatatc     240
actcagaatt attttccagt cggtactgtt gtggaatatg agtgccgtcc aggttacaga     300
agagaacctt ctctatcacc aaaactaact tgccttcaga atttaaaatg gtccacagca     360
gtcgaatttt gtaaaaagaa atcatgccct aatccgggag aaatacgaaa tggtcagatt     420
gatgtaccag gtggcatatt atttggtgca accatctcct tctcatgtaa cacagggtac     480
aaattatttg gctcgacttc tagtttttgt cttatttcag gcagctctgt ccagtggagt     540
gacccgttgc cagagtgcag agaaatttat tgtccagcac caccacaaat tgacaatgga     600
ataattcaag gggaacgtga ccattatgga tatagacagt ctgtaacgta tgcatgtaat     660
aaaggattca ccatgattgg agagcactct atttattgta ctgtgaataa tgatgaagga     720
gagtggagtg ccccaccacc tgaatgcaga ggaaaatctc taacttccaa ggtcccacca     780
acagttcaga aacctaccac agtaaatgtt ccaactacag aagtctcacc aacttctcag     840
aaaaccacca caaaaaccac cacaccaaat gctcaagcaa cacggagtac acctgttcc      900 aggacaacca agcattttca tgaaacaacc ccaaataaag gaagtggaac cacttcaggt     960
actacccgtc ttctatctgg gcacacgtgt ttcacgttga caggtttgct tgggacgcta    1020
gtaaccatgg gcttgctgac t                                              1041

<210> SEQ ID NO 2
<211> LENGTH: 380
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 2

Met Thr Val Ala Arg Pro Ser Val Pro Ala Ala Leu Pro Leu Leu Gly
  1               5                  10                  15

Glu Leu Pro Arg Leu Leu Leu Leu Val Leu Leu Cys Leu Pro Ala Val
                 20                  25                  30

Trp Asp Cys Gly Leu Pro Pro Asp Val Pro Asn Ala Gln Pro Ala Leu
             35                  40                  45

Glu Gly Arg Thr Ser Phe Pro Glu Asp Thr Val Ile Thr Tyr Lys Cys
 50                  55                  60

Glu Glu Ser Phe Val Lys Ile Pro Gly Glu Lys Asp Ser Val Ile Cys
 65                  70                  75                  80

Leu Lys Gly Ser Gln Trp Ser Asp Ile Glu Glu Phe Cys Asn Arg Ser
                 85                  90                  95

Cys Glu Val Pro Thr Arg Leu Asn Ser Ala Ser Leu Lys Gln Pro Tyr
            100                 105                 110

Ile Thr Gln Asn Tyr Phe Pro Val Gly Thr Val Val Glu Tyr Glu Cys
        115                 120                 125

Arg Pro Gly Tyr Arg Arg Glu Pro Ser Leu Ser Pro Lys Leu Thr Cys
    130                 135                 140

Leu Gln Asn Leu Lys Trp Ser Thr Ala Val Glu Phe Cys Lys Lys Lys
145                 150                 155                 160

Ser Cys Pro Asn Pro Gly Glu Ile Arg Asn Gly Gln Ile Asp Val Pro
                165                 170                 175

Gly Gly Ile Leu Phe Gly Ala Thr Ile Ser Phe Ser Cys Asn Thr Gly
            180                 185                 190

Tyr Lys Leu Phe Gly Ser Thr Ser Ser Phe Cys Leu Ile Ser Gly Ser
        195                 200                 205

Ser Val Gln Trp Ser Asp Pro Leu Pro Glu Cys Arg Glu Ile Tyr Cys
    210                 215                 220

Pro Ala Pro Pro Gln Ile Asp Asn Gly Ile Ile Gln Gly Glu Arg Asp
225                 230                 235                 240

His Tyr Gly Tyr Arg Gln Ser Val Thr Tyr Ala Cys Asn Lys Gly Phe
                245                 250                 255

Thr Met Ile Gly Glu His Ser Ile Tyr Cys Thr Val Asn Asn Asp Glu
            260                 265                 270

Gly Glu Trp Ser Gly Pro Pro Glu Cys Arg Gly Lys Ser Leu Thr
        275                 280                 285

Ser Lys Val Pro Pro Thr Val Gln Lys Pro Thr Thr Val Asn Val Pro
    290                 295                 300

Thr Thr Glu Val Ser Pro Thr Ser Gln Lys Thr Thr Thr Lys Thr Thr
305                 310                 315                 320

Thr Pro Asn Ala Gln Ala Thr Arg Ser Thr Pro Val Ser Arg Thr Thr
                325                 330                 335

Lys His Phe His Glu Thr Thr Pro Asn Lys Gly Ser Gly Thr Thr Ser
            340                 345                 350

Gly Thr Thr Arg Leu Leu Ser Gly His Thr Cys Phe Thr Leu Thr Gly
        355                 360                 365

Leu Leu Gly Thr Leu Val Thr Met Gly Leu Leu Thr
    370                 375                 380

<210> SEQ ID NO 3
<211> LENGTH: 306
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 3
cagtgctaca actgtcctaa cccaactgct gactgcaaaa cagccgtcaa ttgttcatct      60
gattttgatg cgtgtctcat taccaaagct gggttacaag tgtataacaa gtgttggaag     120
tttgagcatt gcaatttcaa cgacgtcaca acccgcttga gggaaaatga gctaacgtac     180

| | | |
|---|---|---|
| tactgctgca agaaggacct gtgtaacttt aacgaacagc ttgaaaatgg tgggacatcc | 240 | |
| ttatcagaga aaacagttct tctgctggtg actccatttc tggcagcagc ctggagcctt | 300 | |
| catccc | 306 | |

<210> SEQ ID NO 4
<211> LENGTH: 126
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 4

```
Met Gly Ile Gln Gly Gly Ser Val Leu Phe Gly Leu Leu Leu Val Leu
  1               5                  10                  15

Ala Val Phe Cys His Ser Gly His Gln Cys Tyr Asn Cys Pro Asn Pro
             20                  25                  30

Thr Ala Asp Cys Lys Thr Ala Val Asn Cys Ser Ser Asp Phe Asp Ala
         35                  40                  45

Cys Leu Ile Thr Lys Ala Gly Leu Gln Val Tyr Asn Lys Cys Trp Lys
     50                  55                  60

Phe Glu His Cys Asn Phe Asn Asp Val Thr Thr Arg Leu Arg Glu Asn
 65                  70                  75                  80

Glu Leu Thr Tyr Tyr Cys Cys Lys Lys Asp Leu Cys Asn Phe Asn Glu
                 85                  90                  95

Gln Leu Glu Asn Gly Gly Thr Ser Leu Ser Glu Lys Thr Val Leu Leu
            100                 105                 110

Leu Val Thr Pro Phe Leu Ala Ala Ala Trp Ser Leu His Pro
        115                 120                 125
```

<210> SEQ ID NO 5
<211> LENGTH: 1485
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 5

| | |
|---|---|
| atttcttgtg gctctcctcc gcctatccta aatggccgga ttagttatta ttctacccc | 60 |
| attgctgttg gtaccgtgat aaggtacagt tgttcaggta ccttccgcct cattggagaa | 120 |
| aaagtctat tatgcataac taagacaaa gtggatggaa cctgggataa acctgctcct | 180 |
| aaatgtgaat atttcaataa atattcttct tgccctgagc ccatagtacc aggaggatac | 240 |
| aaaattagag gctctacacc ctacagacat ggtgattctg tgcatttgc ctgtaaaacc | 300 |
| aacttctcca tgaacggaaa caagtctgtt tggtgtcaag caaataatat gtggggggcg | 360 |
| acacgactac caacctgtgt aagtgttttc cctctcgagt gtccagcact cctatgatc | 420 |
| cacaatggac atcacacaag tgagaatgtt ggctccattg ctccaggatt gtctgtgact | 480 |
| tacagctgtg aatctggtta cttgcttgtt ggagaaaaga tcattaactg tttgtcttcg | 540 |
| ggaaaatgga gtgctgtccc ccccacatgt gaagaggcac gctgtaaatc tctaggacga | 600 |
| tttcccaatg ggaaggtaaa ggagcctcca attctccggg ttggtgtaac tgcaaacttt | 660 |
| ttctgtgatg aagggtatcg actgcaaggc ccaccttcta gtcggtgtgt aattgctgga | 720 |
| cagggagttg cttggaccaa aatgccagta tgtggaggtg ggtcgggtgg cggcggatcc | 780 |
| gactgtggcc ttcccccaga tgtacctaat gcccagccag ctttggaagg ccgtacaagt | 840 |

-continued

```
tttcccgagg atactgtaat aacgtacaaa tgtgaagaaa gctttgtgaa aattcctggc    900
gagaaggact cagtgatctg ccttaagggc agtcaatggt cagatattga agagttctgc    960
aatcgtagct gcgaggtgcc aacaaggcta aattctgcat ccctcaaaca gccttatatc   1020
actcagaatt attttccagt cggtactgtt gtggaatatg agtgccgtcc aggttacaga   1080
agagaacctt ctctatcacc aaaactaact tgccttcaga atttaaaatg gtccacagca   1140
gtcgaatttt gtaaaaagaa atcatgccct aatccgggag aaatacgaaa tggtcagatt   1200
gatgtaccag gtggcatatt atttggtgca accatctcct tctcatgtaa cacagggtac   1260
aaattatttg gctcgacttc tagttttttgt cttatttcag cagctctgt ccagtggagt   1320 gacccgttgc cagagtgcag agaaatttat tgtccagcac caccacaaat tgacaatgga   1380
ataattcaag gggaacgtga ccattatgga tatagacagt ctgtaacgta tgcatgtaat   1440
aaaggattca ccatgattgg agagcactct atttattgta ctgtg                   1485
```

<210> SEQ ID NO 6
<211> LENGTH: 495
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 6

```
Ile Ser Cys Gly Ser Pro Pro Ile Leu Asn Gly Arg Ile Ser Tyr
  1               5                  10                  15

Tyr Ser Thr Pro Ile Ala Val Gly Thr Val Ile Arg Tyr Ser Cys Ser
                 20                  25                  30

Gly Thr Phe Arg Leu Ile Gly Glu Lys Ser Leu Leu Cys Ile Thr Lys
             35                  40                  45

Asp Lys Val Asp Gly Thr Trp Asp Lys Pro Ala Pro Lys Cys Glu Tyr
         50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
    130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Gly Gly Gly Ser Gly
                245                 250                 255
```

```
Gly Gly Gly Ser Asp Cys Gly Leu Pro Pro Asp Val Pro Asn Ala Gln
            260                 265                 270

Pro Ala Leu Glu Gly Arg Thr Ser Phe Pro Glu Asp Thr Val Ile Thr
        275                 280                 285

Tyr Lys Cys Glu Glu Ser Phe Val Lys Ile Pro Gly Glu Lys Asp Ser
290                 295                 300

Val Ile Cys Leu Lys Gly Ser Gln Trp Ser Asp Ile Glu Glu Phe Cys
305                 310                 315                 320

Asn Arg Ser Cys Glu Val Pro Thr Arg Leu Asn Ser Ala Ser Leu Lys
                325                 330                 335

Gln Pro Tyr Ile Thr Gln Asn Tyr Phe Pro Val Gly Thr Val Val Glu
            340                 345                 350

Tyr Glu Cys Arg Pro Gly Tyr Arg Arg Glu Pro Ser Leu Ser Pro Lys
        355                 360                 365

Leu Thr Cys Leu Gln Asn Leu Lys Trp Ser Thr Ala Val Glu Phe Cys
370                 375                 380

Lys Lys Lys Ser Cys Pro Asn Pro Gly Glu Ile Arg Asn Gly Gln Ile
385                 390                 395                 400

Asp Val Pro Gly Gly Ile Leu Phe Gly Ala Thr Ile Ser Phe Ser Cys
                405                 410                 415

Asn Thr Gly Tyr Lys Leu Phe Gly Ser Thr Ser Ser Phe Cys Leu Ile
            420                 425                 430

Ser Gly Ser Ser Val Gln Trp Ser Asp Pro Leu Pro Glu Cys Arg Glu
        435                 440                 445

Ile Tyr Cys Pro Ala Pro Pro Gln Ile Asp Asn Gly Ile Ile Gln Gly
        450                 455                 460

Glu Arg Asp His Tyr Gly Tyr Arg Gln Ser Val Thr Tyr Ala Cys Asn
465                 470                 475                 480

Lys Gly Phe Thr Met Ile Gly Glu His Ser Ile Tyr Cys Thr Val
            485                 490                 495

<210> SEQ ID NO 7
<211> LENGTH: 1002
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7
atttcttgtg gctctcctcc gcctatccta aatggccgga ttagttatta ttctaccccc      60
attgctgttg gtaccgtgat aaggtacagt tgttcaggta ccttccgcct cattggagaa     120
aaaagtctat tatgcataac taaagacaaa gtggatggaa cctgggataa acctgctcct     180
aaatgtgaat atttcaataa atattcttct tgccctgagc ccatagtacc aggaggatac     240
aaaattagag gctctacacc ctacagacat ggtgattctg tgacatttgc ctgtaaaacc     300
aacttctcca tgaacggaaa caagtctgtt tggtgtcaag caaataatat gtgggggccg     360
acacgactac caacctgtgt aagtgttttc cctctcgagt gtccagcact tcctatgatc     420
cacaatggac atcacacaag tgagaatgtt ggctccattg ctccaggatt gtctgtgact     480
tacagctgtg aatctggtta cttgcttgtt ggagaaaaga tcattaactg tttgtcttcg     540
ggaaaatgga gtgctgtccc ccccacatgt gaagaggcac gctgtaaatc tctaggacga     600
tttcccaatg ggaaggtaaa ggagcctcca attctccggg ttggtgtaac tgcaaacttt     660
ttctgtgatg aagggtatcg actgcaaggc ccaccttcta gtcggtgtgt aattgctgga     720
```

-continued

```
cagggagttg cttggaccaa atgccagta tgttcaggag gaggaggttc cctgcagtgc      780
tacaactgtc ctaacccaac tgctgactgc aaaacagccg tcaattgttc atctgatttt      840
gatgcgtgtc tcattaccaa agctgggtta caagtgtata acaagtgttg gaagtttgag      900
cattgcaatt tcaacgacgt cacaacccgc ttgagggaaa atgagctaac gtactactgc      960
tgcaagaagg acctgtgtaa ctttaacgaa cagcttgaaa at                         1002
```

<210> SEQ ID NO 8
<211> LENGTH: 334
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 8

```
Ile Ser Cys Gly Ser Pro Pro Ile Leu Asn Gly Arg Ile Ser Tyr
 1               5                  10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
            35                  40                  45

Asp Lys Val Asp Gly Thr Trp Asp Lys Pro Ala Pro Lys Cys Glu Tyr
 50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Ser Gly Gly Gly Gly
                245                 250                 255

Ser Leu Gln Cys Tyr Asn Cys Pro Asn Pro Thr Ala Asp Cys Lys Thr
            260                 265                 270

Ala Val Asn Cys Ser Ser Asp Phe Asp Ala Cys Leu Ile Thr Lys Ala
        275                 280                 285

Gly Leu Gln Val Tyr Asn Lys Cys Trp Lys Phe Glu His Cys Asn Phe
    290                 295                 300

Asn Asp Val Thr Thr Arg Leu Arg Glu Asn Glu Leu Thr Tyr Tyr Cys
```

Cys Lys Lys Asp Leu Cys Asn Phe Asn Glu Gln Leu Glu Asn
              325                 330

<210> SEQ ID NO 9
<211> LENGTH: 1554
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 9
gactgtggcc ttcccccaga tgtacctaat gcccagccag ctttggaagg ccgtacaagt      60
tttcccgagg atactgtaat aacgtacaaa tgtgaagaaa gctttgtgaa aattcctggc     120
gagaaggact cagtgatctg ccttaagggc agtcaatggt cagatattga agagttctgc     180
aatcgtagct gcgaggtgcc aacaaggcta aattctgcat ccctcaaaca gccttatatc     240
actcagaatt attttccagt cggtactgtt gtggaatatg agtgccgtcc aggttacaga     300
agagaacctt ctctatcacc aaaactaact tgccttcaga atttaaaatg tccacagca     360
gtcgaatttt gtaaaaagaa atcatgccct aatccgggag aaatacgaaa tggtcagatt     420
gatgtaccag gtggcatatt attggtgca accatctcct tctcatgtaa cacagggtac     480
aaattatttg gctcgacttc tagttttgt cttatttcag gcagctctgt ccagtggagt     540
gacccgttgc cagagtgcag agaaatttat tgtccagcac caccacaaat tgacaatgga     600
ataattcaag gggaacgtga ccattatgga tatagacagt ctgtaacgta tgcatgtaat     660
aaaggattca ccatgattgg agagcactct atttattgta ctgtgaataa tgatgaagga     720
gagtggagtg gcccaccacc tgaatgcaga tcctctggtg gcggtggctc gggcggaggt     780
gggtcgggtg gcggcggatc catttcttgt ggctctcctc cgcctatcct aaatggccgg     840
attagttatt attctacccc cattgctgtt ggtaccgtga taggtacag ttgttcaggt     900
accttccgcc tcattggaga aaaagtctta ttatgcataa ctaaagacaa agtggatgga     960
acctgggata aacctgctcc taaatgtgaa tatttcaata atattcttc ttgccctgag    1020
cccatagtac caggaggata caaaattaga ggctctacac cctacagaca tggtgattct    1080
gtgacatttg cctgtaaaac caacttctcc atgaacggaa acaagtctgt ttggtgtcaa    1140
gcaaataata tgtgggggcc gacacgacta ccaacctgtg taagtgtttt ccctctcgag    1200
tgtccagcac ttcctatgat ccacaatgga catcacacaa gtgagaatgt ggctccatt     1260
gctccaggat tgtctgtgac ttacagctgt gaatctggtt acttgcttgt tggagaaaag    1320
atcattaact gtttgtcttc gggaaaatgg agtgctgtcc cccccacatg tgaagaggca    1380
cgctgtaaat ctctaggacg atttcccaat gggaaggtaa aggagcctcc aattctccgg    1440
gttggtgtaa ctgcaaactt tttctgtgat gaagggtatc gactgcaagg cccaccttct    1500
agtcggtgtg taattgctgg acaggagtt gcttggacca aaatgccagt atgt          1554

<210> SEQ ID NO 10
<211> LENGTH: 518
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 10

Asp Cys Gly Leu Pro Pro Asp Val Pro Asn Ala Gln Pro Ala Leu Glu

-continued

```
  1               5                   10                  15
Gly Arg Thr Ser Phe Pro Glu Asp Thr Val Ile Thr Tyr Lys Cys Glu
                20                  25                  30

Glu Ser Phe Val Lys Ile Pro Gly Glu Lys Asp Ser Val Ile Cys Leu
                35                  40                  45

Lys Gly Ser Gln Trp Ser Asp Ile Glu Glu Phe Cys Asn Arg Ser Cys
 50                  55                  60

Glu Val Pro Thr Arg Leu Asn Ser Ala Ser Leu Lys Gln Pro Tyr Ile
 65                  70                  75                  80

Thr Gln Asn Tyr Phe Pro Val Gly Thr Val Glu Tyr Glu Cys Arg
                85                  90                  95

Pro Gly Tyr Arg Arg Glu Pro Ser Leu Ser Pro Lys Leu Thr Cys Leu
                100                 105                 110

Gln Asn Leu Lys Trp Ser Thr Ala Val Glu Phe Cys Lys Lys Lys Ser
                115                 120                 125

Cys Pro Asn Pro Gly Glu Ile Arg Asn Gly Gln Ile Asp Val Pro Gly
 130                 135                 140

Gly Ile Leu Phe Gly Ala Thr Ile Ser Phe Ser Cys Asn Thr Gly Tyr
145                 150                 155                 160

Lys Leu Phe Gly Ser Thr Ser Ser Phe Cys Leu Ile Ser Gly Ser Ser
                165                 170                 175

Val Gln Trp Ser Asp Pro Leu Pro Glu Cys Arg Glu Ile Tyr Cys Pro
                180                 185                 190

Ala Pro Pro Gln Ile Asp Asn Gly Ile Ile Gln Gly Glu Arg Asp His
                195                 200                 205

Tyr Gly Tyr Arg Gln Ser Val Thr Tyr Ala Cys Asn Lys Gly Phe Thr
                210                 215                 220

Met Ile Gly Glu His Ser Ile Tyr Cys Thr Val Asn Asn Asp Glu Gly
225                 230                 235                 240

Glu Trp Ser Gly Pro Pro Glu Cys Arg Ser Ser Gly Gly Gly
                245                 250                 255

Ser Gly Gly Gly Gly Ser Gly Gly Gly Ser Ile Ser Cys Gly Ser
                260                 265                 270

Pro Pro Pro Ile Leu Asn Gly Arg Ile Ser Tyr Tyr Ser Thr Pro Ile
                275                 280                 285

Ala Val Gly Thr Val Ile Arg Tyr Ser Cys Ser Gly Thr Phe Arg Leu
                290                 295                 300

Ile Gly Glu Lys Ser Leu Leu Cys Ile Thr Lys Asp Lys Val Asp Gly
305                 310                 315                 320

Thr Trp Asp Lys Pro Ala Pro Lys Cys Glu Tyr Phe Asn Lys Tyr Ser
                325                 330                 335

Ser Cys Pro Glu Pro Ile Val Pro Gly Gly Tyr Lys Ile Arg Gly Ser
                340                 345                 350

Thr Pro Tyr Arg His Gly Asp Ser Val Thr Phe Ala Cys Lys Thr Asn
                355                 360                 365

Phe Ser Met Asn Gly Asn Lys Ser Val Trp Cys Gln Ala Asn Asn Met
370                 375                 380

Trp Gly Pro Thr Arg Leu Pro Thr Cys Val Ser Val Phe Pro Leu Glu
385                 390                 395                 400

Cys Pro Ala Leu Pro Met Ile His Asn Gly His His Thr Ser Glu Asn
                405                 410                 415

Val Gly Ser Ile Ala Pro Gly Leu Ser Val Thr Tyr Ser Cys Glu Ser
                420                 425                 430
```

```
Gly Tyr Leu Leu Val Gly Glu Lys Ile Ile Asn Cys Leu Ser Ser Gly
        435                 440                 445
Lys Trp Ser Ala Val Pro Pro Thr Cys Glu Glu Ala Arg Cys Lys Ser
    450                 455                 460
Leu Gly Arg Phe Pro Asn Gly Lys Val Lys Glu Pro Pro Ile Leu Arg
465                 470                 475                 480
Val Gly Val Thr Ala Asn Phe Phe Cys Asp Glu Gly Tyr Arg Leu Gln
                485                 490                 495
Gly Pro Pro Ser Ser Arg Cys Val Ile Ala Gly Gln Gly Val Ala Trp
            500                 505                 510
Thr Lys Met Pro Val Cys
        515

<210> SEQ ID NO 11
<211> LENGTH: 990
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 11
ctgcagtgct acaactgtcc taacccaact gctgactgca aacagccgt caattgttca      60 tctgattttg atgcgtgtct cattaccaaa gctgggttac aagtgtataa caagtgttgg    120
aagtttgagc attgcaattt caacgacgtc acaacccgct gagggaaaa tgagctaacg     180 tactactgct gcaagaagga cctgtgtaac tttaacgaac agcttgaaaa ttcctctggt    240
ggcggtggct ccggcggagg tgggtccggt ggcggcggat ccatttcttg tggctctcct    300
ccgcctatcc taaatggccg gattagttat tattctaccc ccattgctgt tggtaccgtg    360
ataaggtaca gttgttcagg taccttccgc ctcattggag aaaaagtct attatgcata    420 actaaagaca aagtggatgg aacctgggat aaacctgctc taaatgtga atatttcaat    480 aaatattctt cttgccctga gcccatagta ccaggaggat acaaaattag aggctctaca    540
ccctacagac atggtgattc tgtgacattt gcctgtaaaa ccaacttctc catgaacgga    600
aacaagtctg tttggtgtca agcaaataat atgtggggc cgacacgact accaacctgt    660
gtaagtgttt tccctctcga gtgtccagca cttcctatga tccacaatgg acatcacaca    720
agtgagaatg ttggctccat tgctccagga ttgtctgtga cttacagctg tgaatctggt    780
tacttgcttg ttggagaaaa gatcattaac tgtttgtctt cgggaaaatg gagtgctgtc    840
ccccccacat gtgaagaggc acgctgtaaa tctctaggac gatttcccaa tgggaaggta    900
aaggagcctc caattctccg ggttggtgta actgcaaact ttttctgtga tgaagggtat    960
cgactgcaag gcccacccttc tagtcggtgt                                    990

<210> SEQ ID NO 12
<211> LENGTH: 330
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 12

Leu Gln Cys Tyr Asn Cys Pro Asn Pro Thr Ala Asp Cys Lys Thr Ala
  1               5                  10                  15

Val Asn Cys Ser Ser Asp Phe Asp Ala Cys Leu Ile Thr Lys Ala Gly
                20                  25                  30
```

```
Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
50                  55                  60

Lys Lys Asp Leu Cys Asn Phe Asn Glu Gln Leu Glu Asn Ser Ser Gly
65                  70                  75                  80

Gly Gly Gly Ser Gly Gly Gly Ser Gly Gly Gly Ser Ile Ser
                85                  90                  95

Cys Gly Ser Pro Pro Ile Leu Asn Gly Arg Ile Ser Tyr Tyr Ser
                100             105                 110

Thr Pro Ile Ala Val Gly Thr Val Ile Arg Tyr Ser Cys Ser Gly Thr
            115                 120                 125

Phe Arg Leu Ile Gly Glu Lys Ser Leu Leu Cys Ile Thr Lys Asp Lys
        130                 135                 140

Val Asp Gly Thr Trp Asp Lys Pro Ala Pro Lys Cys Glu Tyr Phe Asn
145                 150                 155                 160

Lys Tyr Ser Ser Cys Pro Glu Pro Ile Val Pro Gly Gly Tyr Lys Ile
                165                 170                 175

Arg Gly Ser Thr Pro Tyr Arg His Gly Asp Ser Val Thr Phe Ala Cys
            180                 185                 190

Lys Thr Asn Phe Ser Met Asn Gly Asn Lys Ser Val Trp Cys Gln Ala
        195                 200                 205

Asn Asn Met Trp Gly Pro Thr Arg Leu Pro Thr Cys Val Ser Val Phe
    210                 215                 220

Pro Leu Glu Cys Pro Ala Leu Pro Met Ile His Asn Gly His His Thr
225                 230                 235                 240

Ser Glu Asn Val Gly Ser Ile Ala Pro Gly Leu Ser Val Thr Tyr Ser
                245                 250                 255

Cys Glu Ser Gly Tyr Leu Leu Val Gly Glu Lys Ile Ile Asn Cys Leu
            260                 265                 270

Ser Ser Gly Lys Trp Ser Ala Val Pro Pro Thr Cys Glu Glu Ala Arg
        275                 280                 285

Cys Lys Ser Leu Gly Arg Phe Pro Asn Gly Lys Val Lys Glu Pro Pro
    290                 295                 300

Ile Leu Arg Val Gly Val Thr Ala Asn Phe Phe Cys Asp Glu Gly Tyr
305                 310                 315                 320

Arg Leu Gln Gly Pro Pro Ser Ser Arg Cys
                325                 330

<210> SEQ ID NO 13
<211> LENGTH: 5994
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 13
caatgcaatg ccccagaatg gcttccattt gccaggccta ccaacctaac tgatgagttt      60
gagtttccca ttgggacata tctgaactat gaatgccgcc ctggttattc cggaagaccg     120
ttttctatca tctgcctaaa aaactcagtc tggactggtg ctaaggacag gtgcagacgt     180
aaatcatgtc gtaatcctcc agatcctgtg aatggcatgg tgcatgtgat caaaggcatc     240
cagttcggat cccaaattaa atattcttgt actaaaggat accgactcat tggttcctcg     300
tctgccacat gcatcatctc aggtgatact gtcatttggg ataatgaaac acctatttgt     360
```

```
gacagaattc cttgtgggct acccccacc atcaccaatg gagatttcat tagcaccaac      420
agagagaatt ttcactatgg atcagtggtg acctaccgct gcaatcctgg aagcggaggg      480
agaaaggtgt ttgagcttgt gggtgagccc tccatatact gcaccagcaa tgacgatcaa      540
gtgggcatct ggagcggccc cgcccctcag tgcattatac ctaacaaatg cacgcctcca      600
aatgtggaaa atggaatatt ggtatctgac aacagaagct tattttcctt aaatgaagtt      660
gtggagttta ggtgtcagcc tggctttgtc atgaaaggac cccgccgtgt gaagtgccag      720
gccctgaaca atgggagcc ggagctacca agctgctcca gggtatgtca gccacctcca      780
gatgtcctgc atgctgagcg tacccaaagg gacaaggaca acttttcacc tgggcaggaa      840
gtgttctaca gctgtgagcc cggctacgac ctcagagggg ctgcgtctat gcgctgcaca      900
ccccagggag actggagccc tgcagccccc acatgtgaag tgaaatcctg tgatgacttc      960
atgggccaac ttcttaatgg ccgtgtgcta tttccagtaa atctccagct tggagcaaaa     1020
gtggattttg tttgtgatga aggatttcaa ttaaaaggca gctctgctag ttactgtgtc     1080
ttggctggaa tggaaagcct tggaatagc agtgttccag tgtgtgaaca atcttttgt     1140 ccaagtcctc cagttattcc taatgggaga cacacaggaa aacctctgga agtctttccc     1200
tttggaaaag cagtaaatta cacatgcgac ccccacccag acagagggac gagcttcgac     1260
ctcattggag agagcaccat ccgctgcaca agtgaccctc aagggaatgg ggtttggagc     1320
agccctgccc ctcgctgtgg aattctgggt cactgtcaag ccccagatca ttttctgttt     1380
gccaagttga aacccaaac caatgcatct gactttccca ttgggacatc tttaaagtac     1440
gaatgccgtc ctgagtacta cgggaggcca ttctctatca catgtctaga taacctggtc     1500
tggtcaagtc ccaaagatgt ctgtaaacgt aaatcatgta aaactcctcc agatccagtg     1560
aatggcatgg tgcatgtgat cacagacatc caggttggat ccagaatcaa ctattcttgt     1620
actacagggc accgactcat tggtcactca tctgctgaat gtatcctctc gggcaatgct     1680
gcccattgga gcacgaagcc gccaatttgt caacgaattc cttgtgggct acccccacc     1740 atcgccaatg gagatttcat tagcaccaac agagagaatt ttcactatgg atcagtggtg     1800
acctaccgct gcaatcctgg aagcggaggg agaaaggtgt ttgagcttgt gggtgagccc     1860
tccatatact gcaccagcaa tgacgatcaa gtgggcatct ggagcggccc ggcccctcag     1920
tgcattatac ctaacaaatg cacgcctcca aatgtggaaa atggaatatt ggtatctgac     1980
aacagaagct tattttcctt aaatgaagtt gtggagttta ggtgtcagcc tggctttgtc     2040
atgaaaggac cccgccgtgt gaagtgccag gccctgaaca atgggagcc ggagctacca     2100 agctgctcca gggtatgtca gccacctcca gatgtcctgc atgctgagcg tacccaaagg     2160
gacaaggaca acttttcacc cgggcaggaa gtgttctaca gctgtgagcc cggctatgac     2220
ctcagagggg ctgcgtctat gcgctgcaca ccccagggag actggagccc tgcagccccc     2280
acatgtgaag tgaaatcctg tgatgacttc atgggccaac ttcttaatgg ccgtgtgcta     2340
tttccagtaa atctccagct tggagcaaaa gtggattttg tttgtgatga aggatttcaa     2400
ttaaaaggca gctctgctag ttattgtgtc ttggctggaa tggaaagcct tggaatagc     2460 agtgttccag tgtgtgaaca atcttttgt ccaagtcctc cagttattcc taatgggaga     2520
cacacaggaa aacctctgga agtctttccc tttggaaaag cagtaaatta cacatgcgac     2580
ccccacccag acagagggac gagcttcgac ctcattggag agagcaccat ccgctgcaca     2640
agtgaccctc aagggaatgg ggtttggagc agccctgccc ctcgctgtgg aattctgggt     2700
cactgtcaag ccccagatca ttttctgttt gccaagttga aacccaaac caatgcatct     2760
```

```
gactttccca ttgggacatc tttaaagtac gaatgccgtc ctgagtacta cgggaggcca    2820
ttctctatca catgtctaga taacctggtc tggtcaagtc ccaaagatgt ctgtaaacgt    2880
aaatcatgta aaactcctcc agatccagtg aatggcatgg tgcatgtgat cacagacatc    2940
caggttggat ccagaatcaa ctattcttgt actacagggc accgactcat tggtcactca    3000
tctgctgaat gtatcctctc aggcaatact gcccattgga gcacgaagcc gccaatttgt    3060
caacgaattc cttgtgggct accccaacc atcgccaatg gagatttcat tagcaccaac    3120
agagagaatt ttcactatgg atcagtggtg acctaccgct gcaatcttgg aagcagaggg    3180 agaaggtgt ttgagcttgt gggtgagccc tccatatact gcaccagcaa tgacgatcaa    3240
gtgggcatct ggagcggccc cgcccctcag tgcattatac ctaacaaatg cacgcctcca    3300
aatgtggaaa atgaatatt ggtatctgac aacagaagct tattttcctt aaatgaagtt    3360
gtggagttta ggtgtcagcc tggctttgtc atgaaaggac cccgccgtgt gaagtgccag    3420
gccctgaaca atgggagcc agagttacca agctgctcca gggtgtgtca gccgcctcca    3480
gaaatcctgc atggtgagca taccccaagc catcaggaca acttttcacc tgggcaggaa    3540
gtgttctaca gctgtgagcc tggctatgac ctcagagggg ctgcgtctct gcactgcaca    3600
ccccagggag actggagccc tgaagccccg agatgtgcag tgaaatcctg tgatgacttc    3660
ttgggtcaac tccctcatgg ccgtgtgcta tttccactta atctccagct tggggcaaag    3720
gtgtcctttg tctgtgatga agggtttcgc ttaaagggca gttccgttag tcattgtgtc    3780
ttggttggaa tgagaagcct ttggaataac agtgttcctg tgtgtgaaca tatcttttgt    3840
ccaaatcctc cagctatcct taatgggaga cacacaggaa ctccctctgg agatattccc    3900 tatgaaaag aaatatctta cacatgtgac ccccacccag acagagggat gaccttcaac    3960
ctcattgggg agagcaccat ccgctgcaca agtgaccctc atgggaatgg ggtttggagc    4020
agccctgccc ctcgctgtga actttctgtt cgtgctggtc actgtaaaac cccagagcag    4080
tttccatttg ccagtcctac gatcccaatt aatgactttg agtttccagt cgggacatct    4140
ttgaattatg aatgccgtcc tgggtatttt gggaaaatgt tctctatctc ctgcctagaa    4200
aacttggtct ggtcaagtgt tgaagacaac tgtagacgaa aatcatgtgg acctccacca    4260
gaacccttca tggaatggt gcatataaac acagatacac agtttggatc aacagttaat    4320
tattcttgta tgaagggtt tcgactcatt ggttccccat ctactacttg tctcgtctca    4380
ggcaataatg tcacatggga taagaaggca cctatttgtg agatcatatc ttgtgagcca    4440
cctccaacca tatccaatgg agacttctac agcaacaata gaacatcttt tcacaatgga    4500
acggtggtaa cttaccagtg ccacactgga ccagatggag aacagctgtt tgagcttgtg    4560
ggagaacggt caatatattg caccagcaaa gatgatcaag ttggtgtttg gagcagccct    4620 cccctcggt gtatttctac taataaatgc acagctccag aagttgaaaa tgcaattaga    4680
gtaccaggaa acaggagttt cttttccctc actgagatca tcagatttag atgtcagccc    4740
gggtttgtca tggtagggtc ccacactgtg cagtgccaga ccaatggcag atgggggccc    4800
aagctgccac actgctccag ggtgtgtcag ccgcctccag aaatcctgca tggtgagcat    4860
accctaagcc atcaggacaa cttttcacct gggcaggaag tgttctacag ctgtgagccc    4920
agctatgacc tcagaggggc tgcgtctctg cactgcacgc cccagggaga ctggagccct    4980 gaagcccta gatgtacagt gaaatcctgt gatgacttcc tgggccaact ccctcatggc    5040
cgtgtgctac ttccacttaa tctccagctt ggggcaaagg tgtcctttgt ttgcgatgaa    5100
gggttccgat aaaaggcag gtctgctagt cattgtgtct tggctggaat gaaagccctt    5160
```

-continued

```
tggaatagca gtgttccagt gtgtgaacaa atcttttgtc caaatcctcc agctatcctt    5220
aatgggagac acacaggaac tcccttggga gatattccct atggaaaaga aatatcttac    5280
gcatgcgaca cccacccaga cagagggatg accttcaacc tcattgggga gagctccatc    5340
cgctgcacaa gtgaccctca agggaatggg gtttggagca gccctgcccc tcgctgtgaa    5400
ctttctgttc ctgctgcctg cccacatcca cccaagatcc aaaacgggca ttacattgga    5460
ggacacgtat ctctatatct tcctgggatg acaatcagct acacttgtga ccccggctac    5520
ctgttagtgg gaaagggctt cattttctgt acagaccagg gaatctggag ccaattggat    5580
cattattgca agaagtaaaa ttgtagcttc ccactgttta tgaatggaat ctcgaaggag    5640
ttagaaatga aaaagtata tcactatgga gattatgtga ctttgaagtg tgaagatggg    5700
tatactctgg aaggcagtcc ctggagccag tgccaggcgg atgacagatg ggaccctcct    5760
ctggccaaat gtacctctcg tgcacatgat gctctcatag ttggcacttt atctggtacg    5820
atcttcttta ttttactcat cattttcctc tcttggataa ttctaaagca cagaaaaggc    5880
aataatgcac atgaaaaccc taagaagtg gctatccatt acattctca aggaggcagc    5940 agcgttcatc cccgaactct gcaaacaaat gaagaaaata gcagggtcct tcct           5994
```

<210> SEQ ID NO 14
<211> LENGTH: 2048
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 14

```
Met Cys Leu Gly Arg Met Gly Ala Ser Ser Pro Arg Ser Pro Glu Pro
  1               5                  10                  15

Val Gly Pro Pro Ala Pro Gly Leu Pro Phe Cys Cys Gly Gly Ser Leu
                 20                  25                  30

Leu Ala Val Val Val Leu Leu Ala Leu Pro Val Ala Trp Gly Gln Cys
             35                  40                  45

Asn Ala Gln Cys Asn Ala Pro Glu Trp Leu Pro Phe Ala Arg Pro Thr
         50                  55                  60

Asn Leu Thr Asp Glu Phe Glu Phe Pro Ile Gly Thr Tyr Leu Asn Tyr
 65                  70                  75                  80

Glu Cys Arg Pro Gly Tyr Ser Gly Arg Pro Phe Ser Ile Ile Cys Leu
                 85                  90                  95

Lys Asn Ser Val Trp Thr Gly Ala Lys Asp Arg Cys Arg Arg Lys Ser
                100                 105                 110

Cys Arg Asn Pro Pro Asp Pro Val Asn Gly Met Val His Val Ile Lys
            115                 120                 125

Gly Ile Gln Phe Gly Ser Gln Ile Lys Tyr Ser Cys Thr Lys Gly Tyr
        130                 135                 140

Arg Leu Ile Gly Ser Ser Ser Ala Thr Cys Ile Ile Ser Gly Asp Thr
145                 150                 155                 160

Val Ile Trp Asp Asn Glu Thr Pro Ile Cys Asp Arg Ile Pro Cys Gly
                165                 170                 175

Leu Pro Pro Thr Ile Thr Asn Gly Asp Phe Ile Ser Thr Asn Arg Glu
            180                 185                 190

Asn Phe His Tyr Gly Ser Val Val Thr Tyr Arg Cys Asn Pro Gly Ser
        195                 200                 205

Gly Gly Arg Lys Val Phe Glu Leu Val Gly Glu Pro Ser Ile Tyr Cys
    210                 215                 220
```

```
Thr Ser Asn Asp Asp Gln Val Gly Ile Trp Ser Gly Pro Ala Pro Gln
225                 230                 235                 240

Cys Ile Ile Pro Asn Lys Cys Thr Pro Pro Asn Val Glu Asn Gly Ile
            245                 250                 255

Leu Val Ser Asp Asn Arg Ser Leu Phe Ser Leu Asn Glu Val Val Glu
        260                 265                 270

Phe Arg Cys Gln Pro Gly Phe Val Met Lys Gly Pro Arg Arg Val Lys
            275                 280                 285

Cys Gln Ala Leu Asn Lys Trp Glu Pro Glu Leu Pro Ser Cys Ser Arg
        290                 295                 300

Val Cys Gln Pro Pro Pro Asp Val Leu His Ala Glu Arg Thr Gln Arg
305                 310                 315                 320

Asp Lys Asp Asn Phe Ser Pro Gly Gln Glu Val Phe Tyr Ser Cys Glu
                325                 330                 335

Pro Gly Tyr Asp Leu Arg Gly Ala Ala Ser Met Arg Cys Thr Pro Gln
            340                 345                 350

Gly Asp Trp Ser Pro Ala Ala Pro Thr Cys Glu Val Lys Ser Cys Asp
            355                 360                 365

Asp Phe Met Gly Gln Leu Leu Asn Gly Arg Val Leu Phe Pro Val Asn
        370                 375                 380

Leu Gln Leu Gly Ala Lys Val Asp Phe Val Cys Asp Glu Gly Phe Gln
385                 390                 395                 400

Leu Lys Gly Ser Ser Ala Ser Tyr Cys Val Leu Ala Gly Met Glu Ser
            405                 410                 415

Leu Trp Asn Ser Ser Val Pro Val Cys Glu Gln Ile Phe Cys Pro Ser
            420                 425                 430

Pro Pro Val Ile Pro Asn Gly Arg His Thr Gly Lys Pro Leu Glu Val
            435                 440                 445

Phe Pro Phe Gly Lys Ala Val Asn Tyr Thr Cys Asp Pro His Pro Asp
        450                 455                 460

Arg Gly Thr Ser Phe Asp Leu Ile Gly Glu Ser Thr Ile Arg Cys Thr
465                 470                 475                 480

Ser Asp Pro Gln Gly Asn Gly Val Trp Ser Ser Pro Ala Pro Arg Cys
                485                 490                 495

Gly Ile Leu Gly His Cys Gln Ala Pro Asp His Phe Leu Phe Ala Lys
            500                 505                 510

Leu Lys Thr Gln Thr Asn Ala Ser Asp Phe Pro Ile Gly Thr Ser Leu
        515                 520                 525

Lys Tyr Glu Cys Arg Pro Glu Tyr Tyr Gly Arg Pro Phe Ser Ile Thr
        530                 535                 540

Cys Leu Asp Asn Leu Val Trp Ser Ser Pro Lys Asp Val Cys Lys Arg
545                 550                 555                 560

Lys Ser Cys Lys Thr Pro Pro Asp Pro Val Asn Gly Met Val His Val
            565                 570                 575

Ile Thr Asp Ile Gln Val Gly Ser Arg Ile Asn Tyr Ser Cys Thr Thr
            580                 585                 590

Gly His Arg Leu Ile Gly His Ser Ser Ala Glu Cys Ile Leu Ser Gly
        595                 600                 605

Asn Ala Ala His Trp Ser Thr Lys Pro Pro Ile Cys Gln Arg Ile Pro
        610                 615                 620

Cys Gly Leu Pro Pro Thr Ile Ala Asn Gly Asp Phe Ile Ser Thr Asn
625                 630                 635                 640

Arg Glu Asn Phe His Tyr Gly Ser Val Val Thr Tyr Arg Cys Asn Pro
```

```
                    645                 650                 655
Gly Ser Gly Gly Arg Lys Val Phe Glu Leu Val Gly Glu Pro Ser Ile
            660                 665                 670

Tyr Cys Thr Ser Asn Asp Asp Gln Val Gly Ile Trp Ser Gly Pro Ala
            675                 680                 685

Pro Gln Cys Ile Ile Pro Asn Lys Cys Thr Pro Pro Asn Val Glu Asn
690                 695                 700

Gly Ile Leu Val Ser Asp Asn Arg Ser Leu Phe Ser Leu Asn Glu Val
705                 710                 715                 720

Val Glu Phe Arg Cys Gln Pro Gly Phe Val Met Lys Gly Pro Arg Arg
                725                 730                 735

Val Lys Cys Gln Ala Leu Asn Lys Trp Glu Pro Glu Leu Pro Ser Cys
            740                 745                 750

Ser Arg Val Cys Gln Pro Pro Asp Val Leu His Ala Glu Arg Thr
            755                 760                 765

Gln Arg Asp Lys Asp Asn Phe Ser Pro Gly Glu Val Phe Tyr Ser
    770                 775                 780

Cys Glu Pro Gly Tyr Asp Leu Arg Gly Ala Ala Ser Met Arg Cys Thr
785                 790                 795                 800

Pro Gln Gly Asp Trp Ser Pro Ala Ala Pro Thr Cys Glu Val Lys Ser
                805                 810                 815

Cys Asp Asp Phe Met Gly Gln Leu Leu Asn Gly Arg Val Leu Phe Pro
            820                 825                 830

Val Asn Leu Gln Leu Gly Ala Lys Val Asp Phe Val Cys Asp Glu Gly
            835                 840                 845

Phe Gln Leu Lys Gly Ser Ser Ala Ser Tyr Cys Val Leu Ala Gly Met
    850                 855                 860

Glu Ser Leu Trp Asn Ser Ser Val Pro Val Cys Glu Gln Ile Phe Cys
865                 870                 875                 880

Pro Ser Pro Pro Val Ile Pro Asn Gly Arg His Thr Gly Lys Pro Leu
                885                 890                 895

Glu Val Phe Pro Phe Gly Lys Ala Val Asn Tyr Thr Cys Asp Pro His
            900                 905                 910

Pro Asp Arg Gly Thr Ser Phe Asp Leu Ile Gly Glu Ser Thr Ile Arg
            915                 920                 925

Cys Thr Ser Asp Pro Gln Gly Asn Gly Val Trp Ser Ser Pro Ala Pro
            930                 935                 940

Arg Cys Gly Ile Leu Gly His Cys Gln Ala Pro Asp His Phe Leu Phe
945                 950                 955                 960

Ala Lys Leu Lys Thr Gln Thr Asn Ala Ser Asp Phe Pro Ile Gly Thr
                965                 970                 975

Ser Leu Lys Tyr Glu Cys Arg Pro Glu Tyr Tyr Gly Arg Pro Phe Ser
            980                 985                 990

Ile Thr Cys Leu Asp Asn Leu Val Trp Ser Ser Pro Lys Asp Val Cys
            995                 1000                1005

Lys Arg Lys Ser Cys Lys Thr Pro Pro Asp Pro Val Asn Gly Met Val
    1010                1015                1020

His Val Ile Thr Asp Ile Gln Val Gly Ser Arg Ile Asn Tyr Ser Cys
1025                1030                1035                1040

Thr Thr Gly His Arg Leu Ile Gly His Ser Ser Ala Glu Cys Ile Leu
                1045                1050                1055

Ser Gly Asn Thr Ala His Trp Ser Thr Lys Pro Pro Ile Cys Gln Arg
            1060                1065                1070
```

```
Ile Pro Cys Gly Leu Pro Pro Thr Ile Ala Asn Gly Asp Phe Ile Ser
    1075                1080                1085

Thr Asn Arg Glu Asn Phe His Tyr Gly Ser Val Val Thr Tyr Arg Cys
    1090                1095                1100

Asn Leu Gly Ser Arg Gly Arg Lys Val Phe Glu Leu Val Gly Glu Pro
1105                1110                1115                1120

Ser Ile Tyr Cys Thr Ser Asn Asp Asp Gln Val Gly Ile Trp Ser Gly
            1125                1130                1135

Pro Ala Pro Gln Cys Ile Ile Pro Asn Lys Cys Thr Pro Pro Asn Val
                1140                1145                1150

Glu Asn Gly Ile Leu Val Ser Asp Asn Arg Ser Leu Phe Ser Leu Asn
    1155                1160                1165

Glu Val Val Glu Phe Arg Cys Gln Pro Gly Phe Val Met Lys Gly Pro
    1170                1175                1180

Arg Arg Val Lys Cys Gln Ala Leu Asn Lys Trp Glu Pro Glu Leu Pro
1185                1190                1195                1200

Ser Cys Ser Arg Val Cys Gln Pro Pro Glu Ile Leu His Gly Glu
            1205                1210                1215

His Thr Pro Ser His Gln Asp Asn Phe Ser Pro Gly Gln Glu Val Phe
    1220                1225                1230

Tyr Ser Cys Glu Pro Gly Tyr Asp Leu Arg Gly Ala Ala Ser Leu His
    1235                1240                1245

Cys Thr Pro Gln Gly Asp Trp Ser Pro Glu Ala Pro Arg Cys Ala Val
    1250                1255                1260

Lys Ser Cys Asp Asp Phe Leu Gly Gln Leu Pro His Gly Arg Val Leu
1265                1270                1275                1280

Phe Pro Leu Asn Leu Gln Leu Gly Ala Lys Val Ser Phe Val Cys Asp
            1285                1290                1295

Glu Gly Phe Arg Leu Lys Gly Ser Ser Val Ser His Cys Val Leu Val
    1300                1305                1310

Gly Met Arg Ser Leu Trp Asn Asn Ser Val Pro Val Cys Glu His Ile
    1315                1320                1325

Phe Cys Pro Asn Pro Pro Ala Ile Leu Asn Gly Arg His Thr Gly Thr
    1330                1335                1340

Pro Ser Gly Asp Ile Pro Tyr Gly Lys Glu Ile Ser Tyr Thr Cys Asp
1345                1350                1355                1360

Pro His Pro Asp Arg Gly Met Thr Phe Asn Leu Ile Gly Glu Ser Thr
            1365                1370                1375

Ile Arg Cys Thr Ser Asp Pro His Gly Asn Gly Val Trp Ser Ser Pro
            1380                1385                1390

Ala Pro Arg Cys Glu Leu Ser Val Arg Ala Gly His Cys Lys Thr Pro
            1395                1400                1405

Glu Gln Phe Pro Phe Ala Ser Pro Thr Ile Pro Ile Asn Asp Phe Glu
    1410                1415                1420

Phe Pro Val Gly Thr Ser Leu Asn Tyr Glu Cys Arg Pro Gly Tyr Phe
1425                1430                1435                1440

Gly Lys Met Phe Ser Ile Ser Cys Leu Glu Asn Leu Val Trp Ser Ser
            1445                1450                1455

Val Glu Asp Asn Cys Arg Arg Lys Ser Cys Gly Pro Pro Glu Pro
            1460                1465                1470

Phe Asn Gly Met Val His Ile Asn Thr Asp Thr Gln Phe Gly Ser Thr
    1475                1480                1485

Val Asn Tyr Ser Cys Asn Glu Gly Phe Arg Leu Ile Gly Ser Pro Ser
    1490                1495                1500
```

```
Thr Thr Cys Leu Val Ser Gly Asn Asn Val Thr Trp Asp Lys Lys Ala
1505                1510                1515                1520

Pro Ile Cys Glu Ile Ile Ser Cys Glu Pro Pro Thr Ile Ser Asn
            1525                1530                1535

Gly Asp Phe Tyr Ser Asn Asn Arg Thr Ser Phe His Asn Gly Thr Val
                1540                1545                1550

Val Thr Tyr Gln Cys His Thr Gly Pro Asp Gly Glu Gln Leu Phe Glu
            1555                1560                1565

Leu Val Gly Glu Arg Ser Ile Tyr Cys Thr Ser Lys Asp Asp Gln Val
                1570                1575                1580

Gly Val Trp Ser Ser Pro Pro Arg Cys Ile Ser Thr Asn Lys Cys
1585                1590                1595                1600

Thr Ala Pro Glu Val Glu Asn Ala Ile Arg Val Pro Gly Asn Arg Ser
                1605                1610                1615

Phe Phe Ser Leu Thr Glu Ile Ile Arg Phe Arg Cys Gln Pro Gly Phe
                1620                1625                1630

Val Met Val Gly Ser His Thr Val Gln Cys Gln Thr Asn Gly Arg Trp
            1635                1640                1645

Gly Pro Lys Leu Pro His Cys Ser Arg Val Cys Gln Pro Pro Pro Glu
            1650                1655                1660

Ile Leu His Gly Glu His Thr Leu Ser His Gln Asp Asn Phe Ser Pro
1665                1670                1675                1680

Gly Gln Glu Val Phe Tyr Ser Cys Glu Pro Ser Tyr Asp Leu Arg Gly
                1685                1690                1695

Ala Ala Ser Leu His Cys Thr Pro Gln Gly Asp Trp Ser Pro Glu Ala
                1700                1705                1710

Pro Arg Cys Thr Val Lys Ser Cys Asp Asp Phe Leu Gly Gln Leu Pro
            1715                1720                1725

His Gly Arg Val Leu Leu Pro Leu Asn Leu Gln Leu Gly Ala Lys Val
            1730                1735                1740

Ser Phe Val Cys Asp Glu Gly Phe Arg Leu Lys Gly Arg Ser Ala Ser
1745                1750                1755                1760

His Cys Val Leu Ala Gly Met Lys Ala Leu Trp Asn Ser Ser Val Pro
                1765                1770                1775

Val Cys Glu Gln Ile Phe Cys Pro Asn Pro Pro Ala Ile Leu Asn Gly
                1780                1785                1790

Arg His Thr Gly Thr Pro Phe Gly Asp Ile Pro Tyr Gly Lys Glu Ile
                1795                1800                1805

Ser Tyr Ala Cys Asp Thr His Pro Asp Arg Gly Met Thr Phe Asn Leu
                1810                1815                1820

Ile Gly Glu Ser Ser Ile Arg Cys Thr Ser Asp Pro Gln Gly Asn Gly
1825                1830                1835                1840

Val Trp Ser Ser Pro Ala Pro Arg Cys Glu Leu Ser Val Pro Ala Ala
                1845                1850                1855

Cys Pro His Pro Pro Lys Ile Gln Asn Gly His Tyr Ile Gly Gly His
                1860                1865                1870

Val Ser Leu Tyr Leu Pro Gly Met Thr Ile Ser Tyr Thr Cys Asp Pro
            1875                1880                1885

Gly Tyr Leu Leu Val Gly Lys Gly Phe Ile Phe Cys Thr Asp Gln Gly
            1890                1895                1900

Ile Trp Ser Gln Leu Asp His Tyr Cys Lys Glu Val Asn Cys Ser Phe
1905                1910                1915                1920

Pro Leu Phe Met Asn Gly Ile Ser Lys Glu Leu Glu Met Lys Lys Val
```

Tyr His Tyr Gly Asp Tyr Val Thr Leu Lys Cys Glu Asp Gly Tyr Thr
    1925                1930                1935
                1940                1945                1950

Leu Glu Gly Ser Pro Trp Ser Gln Cys Gln Ala Asp Asp Arg Trp Asp
        1955                1960                1965

Pro Pro Leu Ala Lys Cys Thr Ser Arg Ala His Asp Ala Leu Ile Val
    1970                1975                1980

Gly Thr Leu Ser Gly Thr Ile Phe Phe Ile Leu Ile Ile Phe Leu
1985                1990                1995                2000

Ser Trp Ile Ile Leu Lys His Arg Lys Gly Asn Asn Ala His Glu Asn
            2005                2010                2015

Pro Lys Glu Val Ala Ile His Leu His Ser Gln Gly Gly Ser Ser Val
        2020                2025                2030

His Pro Arg Thr Leu Gln Thr Asn Glu Glu Asn Ser Arg Val Leu Pro
    2035                2040                2045

<210> SEQ ID NO 15
<211> LENGTH: 1029
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 15

| | |
|---|---:|
| tgtgaggagc caccaacatt tgaagctatg gagctcattg gtaaaccaaa accctactat | 60 |
| gagattggtg aacgagtaga ttataagtgt aaaaaaggat acttctatat acctcctctt | 120 |
| gccacccata ctatttgtga tcggaatcat acatggctac ctgtctcaga tgacgcctgt | 180 |
| tatagagaaa catgtccata tacgggatcc tttaaatg ccaagcagt ccctgcaaat | 240 |
| gggacttacg agtttggtta tcagatgcac tttatttgta atgagggtta ttacttaatt | 300 |
| ggtgaagaaa ttctatattg tgaacttaaa ggatcagtag caatttggag cggtaagccc | 360 |
| ccaatatgtg aaaaggtttt gtgtacacca cctccaaaaa taaaaaatgg aaaacacacc | 420 |
| tttagtgaag tagaagtatt tgagtatctt gatgcagtaa cttatagttg tgatcctgca | 480 |
| cctggaccag atccattttc acttattgga gagagcacga tttattgtgg tgacaattca | 540 |
| gtgtggagtc gtgctgctcc agagtgtaaa gtggtcaaat gtcgatttcc agtagtcgaa | 600 |
| aatggaaaac agatatcagg atttggaaaa aaatttttact acaaagcaac agttatgttt | 660 |
| gaatgcgata agggttttta cctcgatggc agcgacacaa ttgtctgtga cagtaacagt | 720 |
| acttgggatc ccccagttcc aaagtgtctt aaagtgtcga cttcttccac tacaaaatct | 780 |
| ccagcgtcca gtgcctcagg tcctaggcct acttacaagc ctccagtctc aaattatcca | 840 |
| ggatatccta aacctgagga aggaatactt gacagtttgg atgtttgggt cattgctgtg | 900 |
| attgttattg ccatagttgt tggagttgca gtaatttgtg ttgtcccgta cagatatctt | 960 |
| caaaggagga agaagaaagg cacataccta actgatgaga cccacagaga agtaaaattt | 1020 |
| acttctctc | 1029 |

<210> SEQ ID NO 16
<211> LENGTH: 378
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 16

```
Met Glu Pro Pro Gly Arg Arg Glu Cys Pro Phe Pro Ser Trp Arg Phe
 1               5                  10                 15

Phe Pro Gly Leu Leu Leu Ala Ala Met Val Leu Leu Leu Tyr Ser Phe
            20                  25                  30

Ser Asp Ala Cys Glu Glu Pro Thr Phe Glu Ala Met Glu Leu Ile
        35                  40                  45

Gly Lys Pro Lys Pro Tyr Tyr Glu Ile Gly Arg Val Asp Tyr Lys
    50                  55                  60

Cys Lys Lys Gly Tyr Phe Tyr Ile Pro Pro Leu Ala Thr His Thr Ile
 65              70                  75                  80

Cys Asp Arg Asn His Thr Trp Leu Pro Val Ser Asp Asp Ala Cys Tyr
                85                  90                  95

Arg Glu Thr Cys Pro Tyr Ile Arg Asp Pro Leu Asn Gly Gln Ala Val
            100                 105                 110

Pro Ala Asn Gly Thr Tyr Glu Phe Gly Tyr Gln Met His Phe Ile Cys
            115                 120                 125

Asn Glu Gly Tyr Tyr Leu Ile Gly Glu Glu Ile Leu Tyr Cys Glu Leu
            130                 135                 140

Lys Gly Ser Val Ala Ile Trp Ser Gly Lys Pro Ile Cys Glu Lys
145                 150                 155                 160

Val Leu Cys Thr Pro Pro Lys Ile Lys Asn Gly Lys His Thr Phe
            165                 170                 175

Ser Glu Val Glu Val Phe Glu Tyr Leu Asp Ala Val Thr Tyr Ser Cys
            180                 185                 190

Asp Pro Ala Pro Gly Pro Asp Pro Phe Ser Leu Ile Gly Glu Ser Thr
            195                 200                 205

Ile Tyr Cys Gly Asp Asn Ser Val Trp Ser Arg Ala Ala Pro Glu Cys
            210                 215                 220

Lys Val Val Lys Cys Arg Phe Pro Val Val Glu Asn Gly Lys Gln Ile
225                 230                 235                 240

Ser Gly Phe Gly Lys Lys Phe Tyr Tyr Lys Ala Thr Val Met Phe Glu
                245                 250                 255

Cys Asp Lys Gly Phe Tyr Leu Asp Gly Ser Asp Thr Ile Val Cys Asp
            260                 265                 270

Ser Asn Ser Thr Trp Asp Pro Pro Val Pro Lys Cys Leu Lys Val Ser
            275                 280                 285

Thr Ser Ser Thr Thr Lys Ser Pro Ala Ser Ser Ala Ser Gly Pro Arg
290                 295                 300

Pro Thr Tyr Lys Pro Pro Val Ser Asn Tyr Pro Gly Tyr Pro Lys Pro
305                 310                 315                 320

Glu Glu Gly Ile Leu Asp Ser Leu Asp Val Trp Val Ile Ala Val Ile
                325                 330                 335

Val Ile Ala Ile Val Val Gly Val Ala Val Ile Cys Val Val Pro Tyr
            340                 345                 350

Arg Tyr Leu Gln Arg Arg Lys Lys Lys Gly Thr Tyr Leu Thr Asp Glu
            355                 360                 365

Thr His Arg Glu Val Lys Phe Thr Ser Leu
            370                 375
```

<210> SEQ ID NO 17
<211> LENGTH: 440
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 17

```
Met Glu Val Ser Ser Arg Ser Glu Pro Leu Asp Pro Val Trp Leu
  1               5                  10                  15

Leu Val Ala Phe Gly Arg Gly Val Lys Leu Glu Val Leu Leu Leu
             20                  25                  30

Phe Leu Leu Pro Phe Thr Leu Gly His Cys Pro Ala Pro Ser Gln Leu
         35                  40                  45

Pro Ser Ala Lys Pro Ile Asn Leu Thr Asp Glu Ser Met Phe Pro Ile
 50                  55                  60

Gly Thr Tyr Leu Leu Tyr Glu Cys Leu Pro Gly Tyr Ile Lys Arg Gln
 65                  70                  75                  80

Phe Ser Ile Thr Cys Lys Gln Asp Ser Thr Trp Thr Ser Ala Glu Asp
                 85                  90                  95

Lys Cys Ile Arg Lys Gln Cys Lys Thr Pro Ser Asp Pro Glu Asn Gly
                100                 105                 110

Leu Val His Val His Thr Gly Ile Gln Phe Gly Ser Arg Ile Asn Tyr
            115                 120                 125

Thr Cys Asn Gln Gly Tyr Arg Leu Ile Gly Ser Ser Ser Ala Val Cys
            130                 135                 140

Val Ile Thr Asp Gln Ser Val Asp Trp Asp Thr Glu Ala Pro Ile Cys
145                 150                 155                 160

Glu Trp Ile Pro Cys Glu Ile Pro Pro Gly Ile Pro Asn Gly Asp Phe
                165                 170                 175

Phe Ser Ser Thr Arg Glu Asp Phe His Tyr Gly Met Val Val Thr Tyr
            180                 185                 190

Arg Cys Asn Thr Asp Ala Arg Gly Lys Ala Leu Phe Asn Leu Val Gly
            195                 200                 205

Glu Pro Ser Leu Tyr Cys Thr Ser Asn Asp Gly Glu Ile Gly Val Trp
        210                 215                 220

Ser Gly Pro Pro Pro Gln Cys Ile Glu Leu Asn Lys Cys Thr Pro Pro
225                 230                 235                 240

Pro Tyr Val Glu Asn Ala Val Met Leu Ser Glu Asn Arg Ser Leu Phe
                245                 250                 255

Ser Leu Arg Asp Ile Val Glu Phe Arg Cys His Pro Gly Phe Ile Met
            260                 265                 270

Lys Gly Ala Ser Ser Val His Cys Gln Ser Leu Asn Lys Trp Glu Pro
        275                 280                 285

Glu Leu Pro Ser Cys Phe Lys Gly Val Ile Cys Arg Leu Pro Gln Glu
    290                 295                 300

Met Ser Gly Phe Gln Lys Gly Leu Gly Met Lys Lys Glu Tyr Tyr Tyr
305                 310                 315                 320

Gly Glu Asn Val Thr Leu Glu Cys Glu Asp Gly Tyr Thr Leu Glu Gly
                325                 330                 335

Ser Ser Gln Ser Gln Cys Gln Ser Asp Gly Ser Trp Asn Pro Leu Leu
            340                 345                 350

Ala Lys Cys Val Ser Arg Ser Ile Ser Gly Leu Ile Val Gly Ile Phe
        355                 360                 365

Ile Gly Ile Ile Val Phe Ile Leu Val Ile Ile Val Phe Ile Trp Met
    370                 375                 380

Ile Leu Lys Tyr Lys Lys Arg Asn Thr Thr Asp Glu Lys Tyr Lys Glu
385                 390                 395                 400

Val Gly Ile His Leu Asn Tyr Lys Glu Asp Ser Cys Val Arg Leu Gln
```

```
                    405                 410                 415
Ser Leu Leu Thr Ser Gln Glu Asn Ser Ser Thr Thr Ser Pro Ala Arg
            420                 425                 430

Asn Ser Leu Thr Gln Glu Val Ser
        435                 440

<210> SEQ ID NO 18
<211> LENGTH: 232
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 18

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Pro Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 454
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 19

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30
```

```
Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Ser Lys Ser Lys Leu Ile Cys Gln Ala Thr Gly Phe Ser Pro Arg Gln
            130                 135                 140

Ile Gln Val Ser Trp Leu Arg Glu Gly Lys Gln Val Gly Ser Gly Val
145                 150                 155                 160

Thr Thr Asp Gln Val Gln Ala Glu Ala Lys Glu Ser Gly Pro Thr Thr
                165                 170                 175

Tyr Lys Val Thr Ser Thr Leu Thr Ile Lys Glu Ser Asp Trp Leu Ser
            180                 185                 190

Gln Ser Met Phe Thr Cys Arg Val Asp His Arg Gly Leu Thr Phe Gln
            195                 200                 205

Gln Asn Ala Ser Ser Met Cys Val Pro Asp Gln Asp Thr Ala Ile Arg
            210                 215                 220

Val Phe Ala Ile Pro Pro Ser Phe Ala Ser Ile Phe Leu Thr Lys Ser
225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
            260                 265                 270

Asn Ile Ser Glu Ser His Pro Asn Ala Thr Phe Ser Ala Val Gly Glu
            275                 280                 285

Ala Ser Ile Cys Glu Asp Asp Trp Asn Ser Gly Glu Arg Phe Thr Cys
            290                 295                 300

Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
                340                 345                 350

Leu Val Thr Gly Phe Ser Pro Ala Asp Val Phe Val Gln Trp Met Gln
            355                 360                 365

Arg Gly Gln Pro Leu Ser Pro Glu Lys Tyr Val Thr Ser Ala Pro Met
            370                 375                 380

Pro Glu Pro Gln Ala Pro Gly Arg Tyr Phe Ala His Ser Ile Leu Thr
385                 390                 395                 400

Val Ser Glu Glu Glu Trp Asn Thr Gly Glu Thr Tyr Thr Cys Val Val
                405                 410                 415

Ala His Glu Ala Leu Pro Asn Arg Val Thr Glu Arg Thr Val Asp Lys
                420                 425                 430

Ser Thr Gly Lys Pro Thr Leu Tyr Asn Val Ser Leu Val Met Ser Asp
            435                 440                 445

Thr Ala Gly Thr Cys Tyr
```

<210> SEQ ID NO 20
<211> LENGTH: 1530
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 20

```
atgggcgccg cgggcctgct cggggttttc ttggctctcg tcgcaccggg ggtcctcggg      60
atttcttgtg gctctcctcc gcctatccta aatggccgga ttagttatta ttctaccccc     120
attgctgttg gtaccgtgat aaggtacagt tgttcaggta ccttccgcct cattggagaa     180
aaaagtctat tatgcataac taaagacaaa gtggatggaa cctgggataa acctgctcct     240
aaatgtgaat atttcaataa atattcttct tgccctgagc ccatagtacc aggaggatac     300
aaaattagag gctctacacc ctacagacat ggtgattctg tgacatttgc ctgtaaaacc     360
aacttctcca tgaacggaaa caagtctgtt tggtgtcaag caaataatat gtggggccg      420
acacgactac caacctgtgt aagtgttttc cctctcgagt gtccagcact tcctatgatc     480
cacaatggac atcacacaag tgagaatgtt ggctccattg ctccaggatt gtctgtgact     540
tacagctgtg aatctggtta cttgcttgtt ggagaaaaga tcattaactg tttgtcttcg     600
ggaaaatgga gtgctgtccc ccccacatgt gaagaggcac gctgtaaatc tctaggacga     660
tttcccaatg ggaaggtaaa ggagcctcca attctccggg ttggtgtaac tgcaaacttt     720
ttctgtgatg aagggtatcg actgcaaggc ccaccttcta gtcggtgtgt aattgctgga     780
cagggagttg cttggaccaa aatgccagta tgtgaagaaa ttttttgccc actgcggccg     840
cagtctagag acaaaactca cacatgccca ccgtgcccag cacctgaact cctgggggga     900
ccgtcagtct tcctcttccc cccaaaaccc aaggacaccc tcatgatctc ccggacccct     960
gaggtcacat gcgtggtggt ggacgtgagc cacgaagacc ctgaggtcaa gttcaactgg    1020
tacgtggacg gcgtggaggt gcataatgcc aagacaaagc cgcgggagga gcagtacaac    1080
agcacgtacc gtgtggtcag cgtcctcacc gtcctgcacc aggactggct gaatggcaag    1140
gagtacaagt gcaaggtctc caacaaagcc ctcccagtcc ccatcgagaa aaccatctcc    1200
aaagccaaag ggcagccccg agaaccacag gtgtacaccc tgcccccatc ccgggaggag    1260
atgaccaaga accaggtcag cctgacctgc ctggtcaaag gcttctatcc cagcgacatc    1320
gccgtggagt gggagagcaa tgggcagccg gagaacaact acaagaccac gcctcccgtg    1380
ctggactccg acggctcctt cttcctctat agcaagctca ccgtggacaa gagcaggtgg    1440
cagcagggga acgtcttctc atgctccgtg atgcatgagg ctctgcacaa ccactacacg    1500
cagaagagcc tctccctgtc cccgggtaaa                                     1530
```

<210> SEQ ID NO 21
<211> LENGTH: 510
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 21

```
Met Gly Ala Ala Gly Leu Leu Gly Val Phe Leu Ala Leu Val Ala Pro
 1               5                  10                  15

Gly Val Leu Gly Ile Ser Cys Gly Ser Pro Pro Pro Ile Leu Asn Gly
```

-continued

```
             20                  25                  30
Arg Ile Ser Tyr Tyr Ser Thr Pro Ile Ala Val Gly Thr Val Ile Arg
         35                  40                  45

Tyr Ser Cys Ser Gly Thr Phe Arg Leu Ile Gly Glu Lys Ser Leu Leu
         50                  55                  60

Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                     85                  90                  95

Pro Gly Gly Tyr Lys Ile Arg Gly Ser Thr Pro Tyr Arg His Gly Asp
                    100                 105                 110

Ser Val Thr Phe Ala Cys Lys Thr Asn Phe Ser Met Asn Gly Asn Lys
                115                 120                 125

Ser Val Trp Cys Gln Ala Asn Asn Met Trp Gly Pro Thr Arg Leu Pro
            130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                    165                 170                 175

Leu Ser Val Thr Tyr Ser Cys Glu Ser Gly Tyr Leu Leu Val Gly Glu
                180                 185                 190

Lys Ile Ile Asn Cys Leu Ser Ser Gly Lys Trp Ser Ala Val Pro Pro
            195                 200                 205

Thr Cys Glu Glu Ala Arg Cys Lys Ser Leu Gly Arg Phe Pro Asn Gly
210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                    245                 250                 255

Val Ile Ala Gly Gln Gly Val Ala Trp Thr Lys Met Pro Val Cys Glu
                260                 265                 270

Glu Ile Phe Cys Pro Leu Arg Pro Gln Ser Arg Asp Lys Thr His Thr
            275                 280                 285

Cys Pro Pro Cys Pro Ala Pro Glu Leu Leu Gly Gly Pro Ser Val Phe
290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                    325                 330                 335

Lys Phe Asn Trp Tyr Val Asp Gly Val Glu Val His Asn Ala Lys Thr
                340                 345                 350

Lys Pro Arg Glu Glu Gln Tyr Asn Ser Thr Tyr Arg Val Val Ser Val
            355                 360                 365

Leu Thr Val Leu His Gln Asp Trp Leu Asn Gly Lys Glu Tyr Lys Cys
        370                 375                 380

Lys Val Ser Asn Lys Ala Leu Pro Val Pro Ile Glu Lys Thr Ile Ser
385                 390                 395                 400

Lys Ala Lys Gly Gln Pro Arg Glu Pro Gln Val Tyr Thr Leu Pro Pro
                    405                 410                 415

Ser Arg Glu Glu Met Thr Lys Asn Gln Val Ser Leu Thr Cys Leu Val
                420                 425                 430

Lys Gly Phe Tyr Pro Ser Asp Ile Ala Val Glu Trp Glu Ser Asn Gly
            435                 440                 445
```

```
Gln Pro Glu Asn Asn Tyr Lys Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 22
<211> LENGTH: 233
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 22

Glu Pro Arg Ile Pro Lys Pro Ser Thr Pro Pro Gly Ser Ser Cys Pro
1               5                   10                  15

Pro Gly Asn Ile Leu Gly Gly Pro Ser Val Phe Ile Phe Pro Pro Lys
            20                  25                  30

Pro Lys Asp Ala Leu Met Ile Ser Leu Thr Pro Lys Val Thr Cys Val
        35                  40                  45

Val Val Asp Val Ser Glu Asp Asp Pro Asp Val His Val Ser Trp Phe
50                  55                  60

Val Asp Asn Lys Glu Val His Thr Ala Trp Thr Gln Pro Arg Glu Ala
65                  70                  75                  80

Gln Tyr Asn Ser Thr Phe Arg Val Val Ser Ala Leu Pro Ile Gln His
                85                  90                  95

Gln Asp Trp Met Arg Gly Lys Glu Phe Lys Cys Lys Val Asn Asn Lys
            100                 105                 110

Ala Leu Pro Ala Pro Ile Glu Arg Thr Ile Ser Lys Pro Lys Gly Arg
        115                 120                 125

Ala Gln Thr Pro Gln Val Tyr Thr Ile Pro Pro Arg Glu Gln Met
130                 135                 140

Ser Lys Lys Lys Val Ser Leu Thr Cys Leu Val Thr Asn Phe Phe Ser
145                 150                 155                 160

Glu Ala Ile Ser Val Glu Trp Glu Arg Asn Gly Glu Leu Glu Gln Asp
                165                 170                 175

Tyr Lys Asn Thr Pro Pro Ile Leu Asp Ser Asp Gly Thr Tyr Phe Leu
            180                 185                 190

Tyr Ser Lys Leu Thr Val Asp Thr Asp Ser Trp Leu Gln Gly Glu Ile
        195                 200                 205

Phe Thr Cys Ser Val Val His Glu Ala Leu His Asn His His Thr Gln
    210                 215                 220

Lys Asn Leu Ser Arg Ser Pro Gly Lys
225                 230

<210> SEQ ID NO 23
<211> LENGTH: 4860
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 23
gctctctaca cccctcatcac ccctgctgtt ttgcgaacag acacagaaga gcaaattttg    60
```

```
gtggaggccc atggagacag tactccaaaa cagcttgaca tctttgttca tgattttcca    120
cggaagcaga aaccttgtt ccaaaccaga gtagatatga atccagcagg aggcatgctt    180
gtcactccaa ctatagagat tccagcaaaa gaagtgagta cggactccag gcaaaatcaa    240
tatgtggttg tgcaagtaac tggtcctcaa gtgagattgg aaaaggtggt tctcctttct    300
taccagagta gctttctgtt tatccagaca gataaaggca tctatacacc agggtctcca    360
gtactctatc gtgttttttc tatggatcac aacacaagca agatgaacaa aactgtgatt    420
gttgagtttc agactccaga aggcattctt gtcagttcta attcagttga cctaaacttc    480
ttctggcctt acaatttacc agaccttgtc agtttgggga cttggaggat gtgtgccaaa    540
tatgaacatt ccccagagaa ttatactgca tattttgatg tcaggaaata tgtgttgcca    600
agctttgaag tccgtctgca accatcagag aagtttttt acattgacgg caatgaaaat    660
ttccacgtgt ctatcactgc aaggtacttg tatggagagg aagtggaagg tgtggccttt    720
gtcctctttg gagtgaaaat agatgatgct aaaaagagta ttccagactc actcacgaga    780
attccgatta ttgatggaga tgggaaagca acactaaaaa gagatacatt ccgttctcga    840
tttccaaatc tcaatgagct tgttgggcat actctgtatg catctgtaac agtcatgaca    900
gaatcaggca gtgatatggt agtgactgag caaagcggca ttcatattgt ggcatctccc    960
tatcagatcc acttcacaaa acccccaaa tatttcaagc caggaatgcc atatgaactg    1020
acggtgtatg ttaccaaccc tgatggctca ccagctgccc atgtgccagt ggtatcagag    1080
gcctttcatt ctatgggaac cactttgagt gatgggactg ctaagctcat cctgaacata    1140
ccattgaatg ctcaaagcct accaatcact gttagaacta accatggaga cctcccaaga    1200
gaacgccagg caacaaagtc catgacagcc atagcctacc aaacccaggg aggatctgga    1260
aactatcttc atgtagccat tacatctaca gagattaagc ccggagataa cttacctgtc    1320
aatttcaatg tgaagggcaa tgcaaattca ctgaagcaga tcaaatattt cacatacctc    1380
atattgaata aagggaagat tttcaaggtt ggcaggcaac ccaggagaga tgggcagaat    1440
ctggtgacca tgaatctgca tatcactcca gatctcatcc cttccttccg gtttgtggct    1500
tactaccaag tgggaaacaa cgaaattgtg gctgattctg tctgggtgga tgtgaaggat    1560
acctgcatgg gaacgttggt tgtgaaagga gacaatctaa tacaaatgcc aggagctgca    1620
atgaaaatca aattggaagg ggatccaggt gctcgggttg gtcttgtggc tgtggacaaa    1680
gcagtatatg ttctcaatga taaatataag attagccaag ctaagatatg ggacacaata    1740
gaaaagagtg acttttggctg tacagctggc agtggccaga ataatctggg tgtgtttgaa    1800
gatgctggac tggctctgac aaccagcact aatctcaaca ccaaacagag atcagctgca    1860
aagtgtcctc agcctgcaaa tcggaggcgt cgcagttctg ttttgctgct tgacagcaac    1920
gcaagcaaag cggcagaatt tcaggatcaa gacctgcgta atgctgtga agatgtcatg    1980 catgagaacc ccatggggta cacttgtgaa aagcgtgcaa aatacatcca ggagggagat    2040
gcttgtaagg ctgccttcct tgaatgctgt cgctacatca gggggtccg agatgaaaac    2100 caacgggaga gcgagttgtt tctggcaaga gatgataatg aagatggttt catagcagat    2160
agtgatatca tctcaaggtc tgatttcccc aagagttggt tgtggctaac aaaggacttg    2220
accgaggagc taacagtca agggatttca agcaagacaa tgtcttttta tctgagggat    2280
tccatcacaa cctgggtggt gctggctgta agctttacac ccaccaaagg gatctgtgtg    2340
gctgaacctt atgaaataag agtcatgaaa gtcttcttca ttgatcttca aatgccatat    2400
tcagtagtga agaatgagca ggtggagatt cgagctattc tgcacaacta cgttaacgag    2460
```

```
gatatttatg tgcgagtgga actgttatac aacccagcct tctgcagtgc ttccacaaaa    2520
ggacaaagat accgacagca gttcccaatt aaagccctgt cctccagagc agtaccgttt    2580
gtgatagtcc cattagagca aggattgcat gatgttgaga ttaaagcaag tgtccaggaa    2640
gcgttgtggt cagacggtgt gaggaagaaa ctgaaagttg tacctgaagg ggtacagaaa    2700
tccattgtga ctattgttaa actggaccca agggcaaaag gagttggtgg aacacagcta    2760
gaagtgatca aagcccgcaa attagatgac agagtgcctg acacagaaat tgaaaccaag    2820
attatcatcc aaggtgaccc tgtggctcag attattgaaa actcaattga tggaagtaaa    2880
ctcaaccatc tcattatcac tccttctggc tgtggggagc aaaatatgat ccgcatggcc    2940
gcaccagtta ttgccaccta ctacctggac accacagagc agtgggagac tctcggcata    3000
aatcgcagga ctgaagctgt caatcagatc gtgactggtt atgcccagca gatggtgtac    3060
aagaaagcag atcattccta tgcagcattt acaaaccgtg catctagttc ttggctaaca    3120
gcatatgtcg taaaagtctt tgccatggct gccaaaatgg tagcaggcat tagtcatgaa    3180
atcatttgtg gaggtgtgag gtggctgatt ctgaacaggc aacaaccaga tggagcgttc    3240
aaagaaaatg cccctgtact ttctggaaca atgcagggag gaattcaagg tgctgaagaa    3300
gaagtatatt taacagcttt cattctggtt gcgttgttgg aatccaaaac aatctgcaat    3360
gactatgtca atagtctaga cagcagcatc aagaaggcca caattatttt actcaaaaag    3420
tatgagaaac tgcaaaggcc ttacactaca gccctcacag cctatgcttt ggctgctgca    3480
gaccaactca atgatgacag ggtactcatg gcagcatcaa caggaaggga tcattgggaa    3540
gaatacaatg ctcacaccca caacattgaa ggcacttcct atgccttgtt ggccctgctg    3600
aaaatgaaga aatttgatca aactggtccc tagtcagat ggctgacaga tcagaatttt    3660
tatggggaaa catatggaca aacccaagca acagttatgg catttcaagc tcttgctgaa    3720
tatgagattc agatgcctac ccataaggac ttaaacttag atattactat tgaactgcca    3780
gatcgagaag tacctataag gtacagaatt aattatgaaa atgctctcct ggctcggaca    3840
gtagagacca aactcaacca agacatcact gtgacagcat caggtgatgg aaaagcaaca    3900
atgaccattt tgacattcta taacgcacag ttgcaggaga aggcaaatgt tgcaataaaa    3960
tttcatctta atgtttctgt tgaaaacatc cacttgaatg caatgggagc caagggagcc    4020
ctcatgctca agatctgcac aaggtatctg ggagaagttg attctacaat gacaataatt    4080
gatatttcta tgctgactgg ttttctccct gatgctgaag accttacaag gctttctaaa    4140
ggagtggaca gatacatctc cagatatgaa gttgacaata atatggctca gaaagtagct    4200
gttatcattt acttaaacaa ggtctcccac tctgaagatg aatgcctgca ctttaagatt    4260
ctcaagcatt ttgaagttgg cttcattcag ccaggatcag tcaaggtgta cagctactac    4320
aatctagatg aaaaatgtac caagttctac catccagata aaggaacagg ccttctcaat    4380
aagatatgta ttggtaacgt tgccgatgt gcaggagaaa cctgttcctc gctcaaccat    4440
caggaaagga ttgatgttcc attacaaatt gaaaaagcct gcgagacgaa tgtggattat    4500
gtctacaaaa ccaagctgct tcgaatagaa gaacaagatg gtaatgatat ctatgtcatg    4560
gatgttttag aagttattaa acaaggtact gacgaaaatc cacgagcaaa gacccaccag    4620
tacataagtc aaaggaaatg ccaggaggct ctgaatctga aggtgaatga tgattatctg    4680
atctggggtt ccaggagtga cctgttgccc acgaaagata aatttcccta catcattaca    4740
aagaacacat ggattgagag atggccacat gaagacgaat gtcaggaaga agaattccaa    4800
aagttgtgtg atgactttgc tcagtttagc tacacattga ctgagtttgg ctgccctact    4860
```

-continued

<210> SEQ ID NO 24
<211> LENGTH: 1620
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 24

```
Ala Leu Tyr Thr Leu Ile Thr Pro Ala Val Leu Arg Thr Asp Thr Glu
  1               5                  10                  15

Glu Gln Ile Leu Val Glu Ala His Gly Asp Ser Thr Pro Lys Gln Leu
             20                  25                  30

Asp Ile Phe Val His Asp Phe Pro Arg Lys Gln Lys Thr Leu Phe Gln
         35                  40                  45

Thr Arg Val Asp Met Asn Pro Ala Gly Gly Met Leu Val Thr Pro Thr
     50                  55                  60

Ile Glu Ile Pro Ala Lys Glu Val Ser Thr Asp Ser Arg Gln Asn Gln
 65                  70                  75                  80

Tyr Val Val Val Gln Val Thr Gly Pro Gln Val Arg Leu Glu Lys Val
                 85                  90                  95

Val Leu Leu Ser Tyr Gln Ser Ser Phe Leu Phe Ile Gln Thr Asp Lys
            100                 105                 110

Gly Ile Tyr Thr Pro Gly Ser Pro Val Leu Tyr Arg Val Phe Ser Met
        115                 120                 125

Asp His Asn Thr Ser Lys Met Asn Lys Thr Val Ile Val Glu Phe Gln
    130                 135                 140

Thr Pro Glu Gly Ile Leu Val Ser Ser Asn Ser Val Asp Leu Asn Phe
145                 150                 155                 160

Phe Trp Pro Tyr Asn Leu Pro Asp Leu Val Ser Leu Gly Thr Trp Arg
                165                 170                 175

Ile Val Ala Lys Tyr Glu His Ser Pro Glu Asn Tyr Thr Ala Tyr Phe
            180                 185                 190

Asp Val Arg Lys Tyr Val Leu Pro Ser Phe Glu Val Arg Leu Gln Pro
        195                 200                 205

Ser Glu Lys Phe Phe Tyr Ile Asp Gly Asn Glu Asn Phe His Val Ser
    210                 215                 220

Ile Thr Ala Arg Tyr Leu Tyr Gly Glu Glu Val Glu Gly Val Ala Phe
225                 230                 235                 240

Val Leu Phe Gly Val Lys Ile Asp Ala Lys Lys Ser Ile Pro Asp
                245                 250                 255

Ser Leu Thr Arg Ile Pro Ile Ile Asp Gly Asp Gly Lys Ala Thr Leu
            260                 265                 270

Lys Arg Asp Thr Phe Arg Ser Arg Phe Pro Asn Leu Asn Glu Leu Val
        275                 280                 285

Gly His Thr Leu Tyr Ala Ser Val Thr Val Met Thr Glu Ser Gly Ser
    290                 295                 300

Asp Met Val Val Thr Glu Gln Ser Gly Ile His Ile Val Ala Ser Pro
305                 310                 315                 320

Tyr Gln Ile His Phe Thr Lys Thr Pro Lys Tyr Phe Lys Pro Gly Met
                325                 330                 335

Pro Tyr Glu Leu Thr Val Tyr Val Thr Asn Pro Asp Gly Ser Pro Ala
            340                 345                 350

Ala His Val Pro Val Val Ser Glu Ala Phe His Ser Met Gly Thr Thr
        355                 360                 365
```

```
Leu Ser Asp Gly Thr Ala Lys Leu Ile Leu Asn Ile Pro Leu Asn Ala
    370                 375                 380

Gln Ser Leu Pro Ile Thr Val Arg Thr Asn His Gly Asp Leu Pro Arg
385                 390                 395                 400

Glu Arg Gln Ala Thr Lys Ser Met Thr Ala Ile Ala Tyr Gln Thr Gln
                405                 410                 415

Gly Gly Ser Gly Asn Tyr Leu His Val Ala Ile Thr Ser Thr Glu Ile
            420                 425                 430

Lys Pro Gly Asp Asn Leu Pro Val Asn Phe Asn Val Lys Gly Asn Ala
        435                 440                 445

Asn Ser Leu Lys Gln Ile Lys Tyr Phe Thr Tyr Leu Ile Leu Asn Lys
    450                 455                 460

Gly Lys Ile Phe Lys Val Gly Arg Gln Pro Arg Arg Asp Gly Gln Asn
465                 470                 475                 480

Leu Val Thr Met Asn Leu His Ile Thr Pro Asp Leu Ile Pro Ser Phe
                485                 490                 495

Arg Phe Val Ala Tyr Tyr Gln Val Gly Asn Asn Glu Ile Val Ala Asp
            500                 505                 510

Ser Val Trp Val Asp Val Lys Asp Thr Cys Met Gly Thr Leu Val Val
        515                 520                 525

Lys Gly Asp Asn Leu Ile Gln Met Pro Gly Ala Ala Met Lys Ile Lys
    530                 535                 540

Leu Glu Gly Asp Pro Gly Ala Arg Val Gly Leu Val Ala Val Asp Lys
545                 550                 555                 560

Ala Val Tyr Val Leu Asn Asp Lys Tyr Lys Ile Ser Gln Ala Lys Ile
                565                 570                 575

Trp Asp Thr Ile Glu Lys Ser Asp Phe Gly Cys Thr Ala Gly Ser Gly
            580                 585                 590

Gln Asn Asn Leu Gly Val Phe Glu Asp Ala Gly Leu Ala Leu Thr Thr
        595                 600                 605

Ser Thr Asn Leu Asn Thr Lys Gln Arg Ser Ala Ala Lys Cys Pro Gln
    610                 615                 620

Pro Ala Asn Arg Arg Arg Arg Ser Ser Val Leu Leu Leu Asp Ser Asn
625                 630                 635                 640

Ala Ser Lys Ala Ala Glu Phe Gln Asp Gln Asp Leu Arg Lys Cys Cys
                645                 650                 655

Glu Asp Val Met His Glu Asn Pro Met Gly Tyr Thr Cys Glu Lys Arg
            660                 665                 670

Ala Lys Tyr Ile Gln Glu Gly Asp Ala Cys Lys Ala Ala Phe Leu Glu
        675                 680                 685

Cys Cys Arg Tyr Ile Lys Gly Val Arg Asp Glu Asn Gln Arg Glu Ser
    690                 695                 700

Glu Leu Phe Leu Ala Arg Asp Asp Asn Glu Asp Gly Phe Ile Ala Asp
705                 710                 715                 720

Ser Asp Ile Ile Ser Arg Ser Asp Phe Pro Lys Ser Trp Leu Trp Leu
                725                 730                 735

Thr Lys Asp Leu Thr Glu Glu Pro Asn Ser Gln Gly Ile Ser Ser Lys
            740                 745                 750

Thr Met Ser Phe Tyr Leu Arg Asp Ser Ile Thr Thr Trp Val Val Leu
        755                 760                 765

Ala Val Ser Phe Thr Pro Thr Lys Gly Ile Cys Val Ala Glu Pro Tyr
    770                 775                 780

Glu Ile Arg Val Met Lys Val Phe Phe Ile Asp Leu Gln Met Pro Tyr
```

```
               785                 790                 795                 800
Ser Val Val Lys Asn Glu Gln Val Glu Ile Arg Ala Ile Leu His Asn
                805                 810                 815

Tyr Val Asn Glu Asp Ile Tyr Val Arg Val Glu Leu Leu Tyr Asn Pro
            820                 825                 830

Ala Phe Cys Ser Ala Ser Thr Lys Gly Gln Arg Tyr Arg Gln Gln Phe
            835                 840                 845

Pro Ile Lys Ala Leu Ser Ser Arg Ala Val Pro Phe Val Ile Val Pro
        850                 855                 860

Leu Glu Gln Gly Leu His Asp Val Glu Ile Lys Ala Ser Val Gln Glu
865                 870                 875                 880

Ala Leu Trp Ser Asp Gly Val Arg Lys Lys Leu Lys Val Val Pro Glu
                885                 890                 895

Gly Val Gln Lys Ser Ile Val Thr Ile Val Lys Leu Asp Pro Arg Ala
            900                 905                 910

Lys Gly Val Gly Gly Thr Gln Leu Glu Val Ile Lys Ala Arg Lys Leu
            915                 920                 925

Asp Asp Arg Val Pro Asp Thr Glu Ile Glu Thr Lys Ile Ile Gln
        930                 935                 940

Gly Asp Pro Val Ala Gln Ile Ile Glu Asn Ser Ile Asp Gly Ser Lys
945                 950                 955                 960

Leu Asn His Leu Ile Ile Thr Pro Ser Gly Cys Gly Glu Gln Asn Met
                965                 970                 975

Ile Arg Met Ala Ala Pro Val Ile Ala Thr Tyr Tyr Leu Asp Thr Thr
            980                 985                 990

Glu Gln Trp Glu Thr Leu Gly Ile Asn Arg Arg Thr Glu Ala Val Asn
        995                 1000                1005

Gln Ile Val Thr Gly Tyr Ala Gln Gln Met Val Tyr Lys Lys Ala Asp
    1010                1015                1020

His Ser Tyr Ala Ala Phe Thr Asn Arg Ala Ser Ser Trp Leu Thr
1025                1030                1035                1040

Ala Tyr Val Val Lys Val Phe Ala Met Ala Ala Lys Met Val Ala Gly
                1045                1050                1055

Ile Ser His Glu Ile Ile Cys Gly Gly Val Arg Trp Leu Ile Leu Asn
            1060                1065                1070

Arg Gln Gln Pro Asp Gly Ala Phe Lys Glu Asn Ala Pro Val Leu Ser
        1075                1080                1085

Gly Thr Met Gln Gly Gly Ile Gln Gly Ala Glu Glu Val Tyr Leu
    1090                1095                1100

Thr Ala Phe Ile Leu Val Ala Leu Leu Glu Ser Lys Thr Ile Cys Asn
1105                1110                1115                1120

Asp Tyr Val Asn Ser Leu Asp Ser Ser Ile Lys Lys Ala Thr Asn Tyr
                1125                1130                1135

Leu Leu Lys Lys Tyr Glu Lys Leu Gln Arg Pro Tyr Thr Thr Ala Leu
            1140                1145                1150

Thr Ala Tyr Ala Leu Ala Ala Ala Asp Gln Leu Asn Asp Asp Arg Val
        1155                1160                1165

Leu Met Ala Ala Ser Thr Gly Arg Asp His Trp Glu Glu Tyr Asn Ala
    1170                1175                1180

His Thr His Asn Ile Glu Gly Thr Ser Tyr Ala Leu Leu Ala Leu Leu
1185                1190                1195                1200

Lys Met Lys Lys Phe Asp Gln Thr Gly Pro Ile Val Arg Trp Leu Thr
                1205                1210                1215
```

```
Asp Gln Asn Phe Tyr Gly Glu Thr Tyr Gly Gln Thr Gln Ala Thr Val
            1220                1225                1230
Met Ala Phe Gln Ala Leu Ala Glu Tyr Glu Ile Gln Met Pro Thr His
            1235                1240                1245
Lys Asp Leu Asn Leu Asp Ile Thr Ile Glu Leu Pro Asp Arg Glu Val
            1250                1255                1260
Pro Ile Arg Tyr Arg Ile Asn Tyr Glu Asn Ala Leu Leu Ala Arg Thr
1265                1270                1275                1280
Val Glu Thr Lys Leu Asn Gln Asp Ile Thr Val Ala Ser Gly Asp
            1285                1290                1295
Gly Lys Ala Thr Met Thr Ile Leu Thr Phe Tyr Asn Ala Gln Leu Gln
            1300                1305                1310
Glu Lys Ala Asn Val Cys Asn Lys Phe His Leu Asn Val Ser Val Glu
            1315                1320                1325
Asn Ile His Leu Asn Ala Met Gly Ala Lys Gly Ala Leu Met Leu Lys
            1330                1335                1340
Ile Cys Thr Arg Tyr Leu Gly Glu Val Asp Ser Thr Met Thr Ile Ile
1345                1350                1355                1360
Asp Ile Ser Met Leu Thr Gly Phe Leu Pro Asp Ala Glu Asp Leu Thr
            1365                1370                1375
Arg Leu Ser Lys Gly Val Asp Arg Tyr Ile Ser Arg Tyr Glu Val Asp
            1380                1385                1390
Asn Asn Met Ala Gln Lys Val Ala Val Ile Ile Tyr Leu Asn Lys Val
            1395                1400                1405
Ser His Ser Glu Asp Glu Cys Leu His Phe Lys Ile Leu Lys His Phe
            1410                1415                1420
Glu Val Gly Phe Ile Gln Pro Gly Ser Val Lys Val Tyr Ser Tyr Tyr
1425                1430                1435                1440
Asn Leu Asp Glu Lys Cys Thr Lys Phe Tyr His Pro Asp Lys Gly Thr
            1445                1450                1455
Gly Leu Leu Asn Lys Ile Cys Ile Gly Asn Val Cys Arg Cys Ala Gly
            1460                1465                1470
Glu Thr Cys Ser Ser Leu Asn His Gln Glu Arg Ile Asp Val Pro Leu
            1475                1480                1485
Gln Ile Glu Lys Ala Cys Glu Thr Asn Val Asp Tyr Val Tyr Lys Thr
            1490                1495                1500
Lys Leu Leu Arg Ile Glu Glu Gln Asp Gly Asn Asp Ile Tyr Val Met
1505                1510                1515                1520
Asp Val Leu Glu Val Ile Lys Gln Gly Thr Asp Glu Asn Pro Arg Ala
            1525                1530                1535
Lys Thr His Gln Tyr Ile Ser Gln Arg Lys Cys Gln Glu Ala Leu Asn
            1540                1545                1550
Leu Lys Val Asn Asp Asp Tyr Leu Ile Trp Gly Ser Arg Ser Asp Leu
            1555                1560                1565
Leu Pro Thr Lys Asp Lys Ile Ser Tyr Ile Ile Thr Lys Asn Thr Trp
            1570                1575                1580
Ile Glu Arg Trp Pro His Glu Asp Glu Cys Gln Glu Glu Phe Gln
1585                1590                1595                1600
Lys Leu Cys Asp Asp Phe Ala Gln Phe Ser Tyr Thr Leu Thr Glu Phe
            1605                1610                1615
Gly Cys Pro Thr
            1620

<210> SEQ ID NO 25
```

```
<211> LENGTH: 3039
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 25
atttcttgtg gctctcctcc gcctatccta aatggccgga ttagttatta ttctaccccc      60
attgctgttg gtaccgtgat aaggtacagt tgttcaggta ccttccgcct cattggagaa     120
aaaagtctat tatgcataac taaagacaaa gtggatggaa cctgggataa acctgctcct     180
aaatgtgaat atttcaataa atattcttct tgccctgagc ccatagtacc aggaggatac     240
aaaattagag gctctacacc ctacagacat ggtgattctg tgacatttgc ctgtaaaacc     300
aacttctcca tgaacggaaa caagtctgtt tggtgtcaag caaataatat gtgggggccg     360
acacgactac caacctgtgt aagtgttttc cctctcgagt gtccagcact tcctatgatc     420
cacaatggac atcacacaag tgagaatgtt ggctccattg ctccaggatt gtctgtgact     480
tacagctgtg aatctggtta cttgcttgtt ggagaaaaga tcattaactg tttgtcttcg     540
ggaaaatgga gtgctgtccc ccccacatgt gaagaggcac gctgtaaatc tctaggacga     600
tttcccaatg ggaaggtaaa ggagcctcca attctccggg ttggtgtaac tgcaaacttt     660
ttctgtgatg aagggtatcg actgcaaggc ccaccttcta gtcggtgtgt aattgctgga     720
cagggagttg cttggaccaa aatgccagta tgtgaagaaa ttttttgccc atcacctccc     780
cctattctca atggaagaca tataggcaac tcactagcaa atgtctcata tggaagcata     840
gtcacttaca cttgtgaccc ggacccagag gaaggagtga acttcatcct tattggagag     900
agcactctcc gttgtacagt tgatagtcag aagactggga cctggagtgg ccctgcccca     960
cgctgtgaac tttctacttc tgcggttcag tgtccacatc cccagatcct aagaggccga    1020
atggtatctg ggcagaaaga tcgatatacc tataacgaca ctgtgatatt tgcttgcatg    1080
tttggcttca ccttgaaggg cagcaagcaa atccgatgca atgcccaagg cacatgggag    1140
ccatctgcac cagtctgtga aaaggaatgc caggcccctc ctaacatcct caatgggcaa    1200
aaggaagata gacacatggt ccgctttgac cctggaacat ctataaaata tagctgtaac    1260
cctggctatg tgctggtggg agaagaatcc atacagtgta cctctgaggg ggtgtggaca    1320
ccccctgtac cccaatgcaa agtggcagcg tgtgaagcta caggaaggca actcttgaca    1380 aaacccagc accaatttgt tagaccagat gtcaactctt cttgtggtga agggtacaag    1440
ttaagtggga gtgtttatca ggagtgtcaa ggcacaattc cttggtttat ggagattcgt    1500
ctttgtaaag aaatcacctg cccaccaccc cctgttatct acaatggggc acacaccggg    1560
agttccttag aagattttcc atatggaacc acggtcactt acacatgtaa ccctgggcca    1620
gaaagaggag tggaattcag cctcattgga gagagcacca tccgttgtac aagcaatgat    1680
caagaaagag gcacctggag tggccctgct cccctatgta aactttccct ccttgctgtc    1740
cagtgctcac atgtccatat tgcaaatgga tacaagatat ctggcaagga agccccatat    1800
ttctacaatg cactgtgac attcaagtgt tatagtggat ttacttgaa gggcagtagt    1860 cagattcgtt gcaaagctga taacacctgg gatcctgaaa taccagtttg tgaaaaagaa    1920
acatgccagc atgtgagaca gagtcttcaa gaacttccag ctggttcacg tgtggagcta    1980
gttaatacgt cctgccaaga tgggtaccag ttgactggac atgcttatca gatgtgtcaa    2040
gatgctgaaa atgaatttg gttcaaaaag attccacttt gtaaagttat tcactgtcac    2100
cctccaccag tgattgtcaa tgggaagcac acagggatga tggcagaaaa ctttctatat    2160
```

-continued

```
ggaaatgaag tctcttatga atgtgaccaa ggattctatc tcctgggaga gaaaaaattg   2220
cagtgcagaa gtgattctaa aggacatgga tcttggagcg ggccttcccc acagtgctta   2280
cgatctcctc ctgtgactcg ctgccctaat ccagaagtca acatgggta caagctcaat    2340 aaaacacatt ctgcatattc ccacaatgac atagtgtatg ttgactgcaa tcctggcttc   2400
atcatgaatg gtagtcgcgt gattaggtgt catactgata acacatgggt gccaggtgtg   2460
ccaacttgta tgaaaaaagc cttcataggg tgtccacctc cgcctaagac ccctaacggg   2520
aaccatactg gtggaaacat agctcgattt tctcctggaa tgtcaatcct gtacagctgt   2580
gaccaaggct acctgctggt gggagaggca ctccttcttt gcacacatga gggaacctgg   2640
agccaacctg cccctcattg taaagaggta aactgtagct caccagcaga tatggatgga   2700
atccagaaag ggctggaacc aaggaaaatg tatcagtatg gagctgttgt aactctggag   2760
tgtgaagatg gtatatgct ggaaggcagt ccccagagcc agtgccaatc ggatcaccaa    2820
tggaaccctc ccctggcggt ttgcagatcc cgttcacttg ctcctgtcct ttgtggtatt   2880
gctgcaggtt tgatacttct taccttcttg attgtcatta ccttatacgt gatatcaaaa   2940
cacagagaac gcaattatta tacagataca agccagaaag aagcttttca tttagaagca   3000
cgagaagtat attctgttga tccatacaac ccagccagc                          3039
```

<210> SEQ ID NO 26
<211> LENGTH: 1033
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 26

```
Met Gly Ala Ala Gly Leu Leu Gly Val Phe Leu Ala Leu Val Ala Pro
  1               5                  10                  15

Gly Val Leu Gly Ile Ser Cys Gly Ser Pro Pro Pro Ile Leu Asn Gly
             20                  25                  30

Arg Ile Ser Tyr Tyr Ser Thr Pro Ile Ala Val Gly Thr Val Ile Arg
         35                  40                  45

Tyr Ser Cys Ser Gly Thr Phe Arg Leu Ile Gly Glu Lys Ser Leu Leu
     50                  55                  60

Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205
```

```
Thr Cys Glu Glu Ala Arg Cys Lys Ser Leu Gly Arg Phe Pro Asn Gly
    210                 215                 220
Lys Val Lys Glu Pro Pro Ile Leu Arg Val Gly Val Thr Ala Asn Phe
225                 230                 235                 240
Phe Cys Asp Glu Gly Tyr Arg Leu Gln Gly Pro Pro Ser Ser Arg Cys
            245                 250                 255
Val Ile Ala Gly Gln Gly Val Ala Trp Thr Lys Met Pro Val Cys Glu
                260                 265                 270
Glu Ile Phe Cys Pro Ser Pro Pro Ile Leu Asn Gly Arg His Ile
            275                 280                 285
Gly Asn Ser Leu Ala Asn Val Ser Tyr Gly Ser Ile Val Thr Tyr Thr
    290                 295                 300
Cys Asp Pro Asp Pro Glu Glu Gly Val Asn Phe Ile Leu Ile Gly Glu
305                 310                 315                 320
Ser Thr Leu Arg Cys Thr Val Asp Ser Gln Lys Thr Gly Thr Trp Ser
            325                 330                 335
Gly Pro Ala Pro Arg Cys Glu Leu Ser Thr Ser Ala Val Gln Cys Pro
                340                 345                 350
His Pro Gln Ile Leu Arg Gly Arg Met Val Ser Gly Gln Lys Asp Arg
            355                 360                 365
Tyr Thr Tyr Asn Asp Thr Val Ile Phe Ala Cys Met Phe Gly Phe Thr
    370                 375                 380
Leu Lys Gly Ser Lys Gln Ile Arg Cys Asn Ala Gln Gly Thr Trp Glu
385                 390                 395                 400
Pro Ser Ala Pro Val Cys Glu Lys Glu Cys Gln Ala Pro Pro Asn Ile
            405                 410                 415
Leu Asn Gly Gln Lys Glu Asp Arg His Met Val Arg Phe Asp Pro Gly
                420                 425                 430
Thr Ser Ile Lys Tyr Ser Cys Asn Pro Gly Tyr Val Leu Val Gly Glu
            435                 440                 445
Glu Ser Ile Gln Cys Thr Ser Glu Gly Val Trp Thr Pro Pro Val Pro
    450                 455                 460
Gln Cys Lys Val Ala Ala Cys Glu Ala Thr Gly Arg Gln Leu Leu Thr
465                 470                 475                 480
Lys Pro Gln His Gln Phe Val Arg Pro Asp Val Asn Ser Ser Cys Gly
            485                 490                 495
Glu Gly Tyr Lys Leu Ser Gly Ser Val Tyr Gln Glu Cys Gln Gly Thr
                500                 505                 510
Ile Pro Trp Phe Met Glu Ile Arg Leu Cys Lys Glu Ile Thr Cys Pro
            515                 520                 525
Pro Pro Pro Val Ile Tyr Asn Gly Ala His Thr Gly Ser Ser Leu Glu
    530                 535                 540
Asp Phe Pro Tyr Gly Thr Thr Val Thr Tyr Thr Cys Asn Pro Gly Pro
545                 550                 555                 560
Glu Arg Gly Val Glu Phe Ser Leu Ile Gly Glu Ser Thr Ile Arg Cys
            565                 570                 575
Thr Ser Asn Asp Gln Glu Arg Gly Thr Trp Ser Gly Pro Ala Pro Leu
                580                 585                 590
Cys Lys Leu Ser Leu Leu Ala Val Gln Cys Ser His Val His Ile Ala
            595                 600                 605
Asn Gly Tyr Lys Ile Ser Gly Lys Glu Ala Pro Tyr Phe Tyr Asn Asp
    610                 615                 620
Thr Val Thr Phe Lys Cys Tyr Ser Gly Phe Thr Leu Lys Gly Ser Ser
```

```
                625                 630                 635                 640
Gln Ile Arg Cys Lys Ala Asp Asn Thr Trp Asp Pro Glu Ile Pro Val
                    645                 650                 655
Cys Glu Lys Glu Thr Cys Gln His Val Arg Gln Ser Leu Gln Glu Leu
                660                 665                 670
Pro Ala Gly Ser Arg Val Glu Leu Val Asn Thr Ser Cys Gln Asp Gly
            675                 680                 685
Tyr Gln Leu Thr Gly His Ala Tyr Gln Met Cys Gln Asp Ala Glu Asn
        690                 695                 700
Gly Ile Trp Phe Lys Lys Ile Pro Leu Cys Lys Val Ile His Cys His
705                 710                 715                 720
Pro Pro Pro Val Ile Val Asn Gly Lys His Thr Gly Met Met Ala Glu
                725                 730                 735
Asn Phe Leu Tyr Gly Asn Glu Val Ser Tyr Glu Cys Asp Gln Gly Phe
                740                 745                 750
Tyr Leu Leu Gly Glu Lys Lys Leu Gln Cys Arg Ser Asp Ser Lys Gly
                755                 760                 765
His Gly Ser Trp Ser Gly Pro Ser Pro Gln Cys Leu Arg Ser Pro Pro
    770                 775                 780
Val Thr Arg Cys Pro Asn Pro Glu Val Lys His Gly Tyr Lys Leu Asn
785                 790                 795                 800
Lys Thr His Ser Ala Tyr Ser His Asn Asp Ile Val Tyr Val Asp Cys
                805                 810                 815
Asn Pro Gly Phe Ile Met Asn Gly Ser Arg Val Ile Arg Cys His Thr
                820                 825                 830
Asp Asn Thr Trp Val Pro Gly Val Pro Thr Cys Met Lys Lys Ala Phe
            835                 840                 845
Ile Gly Cys Pro Pro Pro Lys Thr Pro Asn Gly Asn His Thr Gly
        850                 855                 860
Gly Asn Ile Ala Arg Phe Ser Pro Gly Met Ser Ile Leu Tyr Ser Cys
865                 870                 875                 880
Asp Gln Gly Tyr Leu Leu Val Gly Glu Ala Leu Leu Leu Cys Thr His
                885                 890                 895
Glu Gly Thr Trp Ser Gln Pro Ala Pro His Cys Lys Glu Val Asn Cys
                900                 905                 910
Ser Ser Pro Ala Asp Met Asp Gly Ile Gln Lys Gly Leu Glu Pro Arg
            915                 920                 925
Lys Met Tyr Gln Tyr Gly Ala Val Val Thr Leu Glu Cys Glu Asp Gly
        930                 935                 940
Tyr Met Leu Glu Gly Ser Pro Gln Ser Gln Cys Gln Ser Asp His Gln
945                 950                 955                 960
Trp Asn Pro Pro Leu Ala Val Cys Arg Ser Arg Ser Leu Ala Pro Val
                965                 970                 975
Leu Cys Gly Ile Ala Ala Gly Leu Ile Leu Leu Thr Phe Leu Ile Val
            980                 985                 990
Ile Thr Leu Tyr Val Ile Ser Lys His Arg Glu Arg Asn Tyr Tyr Thr
        995                 1000                1005
Asp Thr Ser Gln Lys Glu Ala Phe His Leu Glu Ala Arg Glu Val Tyr
    1010                1015                1020
Ser Val Asp Pro Tyr Asn Pro Ala Ser
1025                1030

<210> SEQ ID NO 27
<211> LENGTH: 3042
```

<212> TYPE: DNA
<213> ORGANISM: Artificial Sequence
<220> FEATURE:
<223> OTHER INFORMATION: Description of Artificial Sequence:/note = synthetic construct

<400> SEQUENCE: 27

```
atttcttgtg accctcctcc tgaagtcaaa aatgctcgga aaccctatta ttctcttccc      60
atagttcctg gaactgttct gaggtacact tgttcaccta gctaccgcct cattggagaa     120
aaggctatct tttgtataag tgaaaatcaa gtgcatgcca cctgggataa agctcctcct     180
atatgtgaat ctgtgaataa aaccatttct tgctcagatc ccatagtacc aggggggattc     240
atgaataaag gatctaaggc accattcaga catggtgatt ctgtgacatt tacctgtaaa     300
gccaacttca ccatgaaagg aagcaaaact gtctggtgcc aggcaaatga atgtggggga     360
ccaacagctc tgccagtctg tgagagtgat ttccctctgg agtgcccatc acttccaacg     420
attcataatg gacaccacac aggacagcat gttgaccagt ttgttgctgg gttgtctgtg     480
acatacagtt gtgaacctgg ctatttgctc actggaaaaa agacaattaa gtgcttatct     540
tcaggagact gggatggtgt catcccgaca tgcaaagagg cccagtgtga acatccagga     600
aagtttccca atgggcaggt aaaggaacct ctgagccttc aggttggcac aactgtgtac     660
ttctcctgta tgaagggta ccaattacaa ggacaaccct ctagtcagtg tgtaattgtt     720
gaacagaaag ccatctggac taagaagcca gtatgtaaag aaattctctg cccaccacct     780
ccacctgttc gtaatggaag tcatacaggc agcttttcag aaaatgtacc atatggaagc     840
acagttacct acacctgtga cccaagccca gagaaaggcg tgagcttcac tcttattgga     900
gagaagacta tcaattgtac tactggtagt cagaagactg gatctggag tggccctgct     960
ccatattgtg tactttcaac ttctgcagtt ctgtgtttac aaccgaagat caaaagaggg    1020
caaatattat ctattttgaa agatagttat tcatataatg acactgtggc attttcttgt    1080
gaacctggct tcaccttgaa gggcaacagg agcattcgat gcaatgctca tggcacatgg    1140
gagccaccgg taccagtgtg tgaaaaagga tgtcaggctc ctcctaaaat tatcaatggg    1200
caaaaagaag atagttactt gctcaacttt gaccctggta catccataag atatagctgt    1260
gaccctggct atttactggt gggagaggac actatacatt gcaccctga ggggaagtgg    1320
acacccatta ctccccagtg cacagttgca gagtgtaagc cagtaggacc acatctcttt    1380
aagaggcctc agaatcagtt tattaggaca gctgttaatt cttcttgtga tgaagggttc    1440
cagttaagtg agagtgctta tcaactgtgt caaggtacaa ttccttggtt tatagaaatc    1500
cgtctttgta agaaatcac ctgcccacca cctcctgtta tacacaacgg gacacataca    1560
tggagttcct cagaagatgt cccatatgga actgtggtca catacatgtg ctatcctggg    1620
ccagaggaag gcgtaaaatt caaactcatc ggggagcaaa ccatccactg tacaagtgac    1680
agcagaggaa gaggctcctg gagtagcccc gctcctctct gtaaactttc cctcccagct    1740
gtccagtgca cagacgttca tgttgaaaat ggagtcaagc tcactgacaa taaagcccca    1800
tatttctaca atgatagtgt gatgttcaag tgtgatgatg gatatatttt gagtggaagc    1860
agtcagatcc ggtgtaaagc caataatacc tgggatcctg aaaaaccact ttgtaaaaaa    1920
gaaggatgtg agcctatgag agtacatggc cttccagatg attcacatat aaaactagtg    1980
aaaagaacct gtcaaaatgg gtaccagttg actggatata cttatgagaa gtgtcaaaat    2040
gctgagaatg ggacttggtt taaaagatt gaagtttgta cagttattct ctgtcaacct    2100
ccaccaaaaa ttgcaaatgg tggtcacaca ggcatgatgg caaagcactt cctatatgga    2160
```

```
                                              -continued aatgaagttt cttatgaatg tgatgaaggg ttctatcttt tgggagagaa aagtttgcag    2220
tgcgtaaatg attctaaagg tcatggctct tggagtggac ctccaccaca atgcttacaa    2280
tcttctcctc taactcattg ccccgatcca gaagtcaaac atggttacaa actcaataaa    2340
actcattctg cattttctca taatgacata gtacattttg tctgcaatca aggcttcatc    2400
atgaacggca gccacttgat aaggtgtcat actaataaca catggttacc aggtgtacca    2460
acttgtatca gaaaggcttc tttagggtgt cagtctccat ccacaatccc caatgggaat    2520
catactggtg ggagtatagc tcgatttccc cctggaatgt cagtcatgta cagttgctac    2580
caaggcttcc ttatggctgg agaggcacgt cttatctgta tcatgaggg tacctggagt     2640 caacctcccc cttttgcaa agaggtaaac tgtagcttcc ctgaagatac aaatggaatc     2700
cagaagggat ttcaacctgg gaaaacctat cgatttgggg ctactgtgac tctggaatgt    2760
gaggatgggt atccttgga gggaagtccc cagagccagt gccaggatga cagccaatgg     2820
aaccctccct tggctctttg caaataccgt aggtggtcaa ctattcctct tatttgtggt    2880
atttctgtgg gctcagcact tatcattttg atgagtgtcg gcttctgtat gatattaaaa    2940
cacagagaaa gcaattatta tacaaagaca agacccaaag aaggagctct tcatttagaa    3000
acacgagaag tatattctat tgatccatat aacccagcaa gc                       3042

<210> SEQ ID NO 28
<211> LENGTH: 1014
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 28

Ile Ser Cys Asp Pro Pro Glu Val Lys Asn Ala Arg Lys Pro Tyr
1               5                   10                  15

Tyr Ser Leu Pro Ile Val Pro Gly Thr Val Leu Arg Tyr Thr Cys Ser
            20                  25                  30

Pro Ser Tyr Arg Leu Ile Gly Glu Lys Ala Ile Phe Cys Ile Ser Glu
        35                  40                  45

Asn Gln Val His Ala Thr Trp Asp Lys Ala Pro Pro Ile Cys Glu Ser
    50                  55                  60

Val Asn Lys Thr Ile Ser Cys Ser Asp Pro Ile Val Pro Gly Gly Phe
65                  70                  75                  80

Met Asn Lys Gly Ser Lys Ala Pro Phe Arg His Gly Asp Ser Val Thr
                85                  90                  95

Phe Thr Cys Lys Ala Asn Phe Thr Met Lys Gly Ser Lys Thr Val Trp
            100                 105                 110

Cys Gln Ala Asn Glu Met Trp Gly Pro Thr Ala Leu Pro Val Cys Glu
        115                 120                 125

Ser Asp Phe Pro Leu Glu Cys Pro Ser Leu Pro Thr Ile His Asn Gly
    130                 135                 140

His His Thr Gly Gln His Val Asp Gln Phe Val Ala Gly Leu Ser Val
145                 150                 155                 160

Thr Tyr Ser Cys Glu Pro Gly Tyr Leu Leu Thr Gly Lys Lys Thr Ile
                165                 170                 175

Lys Cys Leu Ser Ser Gly Asp Trp Asp Gly Val Ile Pro Thr Cys Lys
            180                 185                 190

Glu Ala Gln Cys Glu His Pro Gly Lys Phe Pro Asn Gly Gln Val Lys
        195                 200                 205
```

-continued

```
Glu Pro Leu Ser Leu Gln Val Gly Thr Thr Val Tyr Phe Ser Cys Asn
    210                 215                 220
Glu Gly Tyr Gln Leu Gln Gly Gln Pro Ser Ser Gln Cys Val Ile Val
225                 230                 235                 240
Glu Gln Lys Ala Ile Trp Thr Lys Lys Pro Val Cys Lys Glu Ile Leu
                245                 250                 255
Cys Pro Pro Pro Pro Val Arg Asn Gly Ser His Thr Gly Ser Phe
                260                 265                 270
Ser Glu Asn Val Pro Tyr Gly Ser Thr Val Thr Tyr Thr Cys Asp Pro
            275                 280                 285
Ser Pro Glu Lys Gly Val Ser Phe Thr Leu Ile Gly Glu Lys Thr Ile
    290                 295                 300
Asn Cys Thr Thr Gly Ser Gln Lys Thr Gly Ile Trp Ser Gly Pro Ala
305                 310                 315                 320
Pro Tyr Cys Val Leu Ser Thr Ser Ala Val Leu Cys Leu Gln Pro Lys
                325                 330                 335
Ile Lys Arg Gly Gln Ile Leu Ser Ile Leu Lys Asp Ser Tyr Ser Tyr
                340                 345                 350
Asn Asp Thr Val Ala Phe Ser Cys Glu Pro Gly Phe Thr Leu Lys Gly
            355                 360                 365
Asn Arg Ser Ile Arg Cys Asn Ala His Gly Thr Trp Glu Pro Pro Val
    370                 375                 380
Pro Val Cys Glu Lys Gly Cys Gln Ala Pro Lys Ile Ile Asn Gly
385                 390                 395                 400
Gln Lys Glu Asp Ser Tyr Leu Leu Asn Phe Pro Gly Thr Ser Ile
                405                 410                 415
Arg Tyr Ser Cys Asp Pro Gly Tyr Leu Leu Val Gly Glu Asp Thr Ile
                420                 425                 430
His Cys Thr Pro Glu Gly Lys Trp Thr Pro Ile Thr Pro Gln Cys Thr
            435                 440                 445
Val Ala Glu Cys Lys Pro Val Gly Pro His Leu Phe Lys Arg Pro Gln
    450                 455                 460
Asn Gln Phe Ile Arg Thr Ala Val Asn Ser Ser Cys Asp Glu Gly Phe
465                 470                 475                 480
Gln Leu Ser Glu Ser Ala Tyr Gln Leu Cys Gln Gly Thr Ile Pro Trp
                485                 490                 495
Phe Ile Glu Ile Arg Leu Cys Lys Glu Ile Thr Cys Pro Pro Pro Pro
                500                 505                 510
Val Ile His Asn Gly Thr His Thr Trp Ser Ser Glu Asp Val Pro
            515                 520                 525
Tyr Gly Thr Val Val Thr Tyr Met Cys Tyr Pro Gly Pro Glu Glu Gly
    530                 535                 540
Val Lys Phe Lys Leu Ile Gly Glu Gln Thr Ile His Cys Thr Ser Asp
545                 550                 555                 560
Ser Arg Gly Arg Gly Ser Trp Ser Ser Pro Ala Pro Leu Cys Lys Leu
                565                 570                 575
Ser Leu Pro Ala Val Gln Cys Thr Asp Val His Val Glu Asn Gly Val
            580                 585                 590
Lys Leu Thr Asp Asn Lys Ala Pro Tyr Phe Tyr Asn Asp Ser Val Met
    595                 600                 605
Phe Lys Cys Asp Asp Gly Tyr Ile Leu Ser Gly Ser Ser Gln Ile Arg
610                 615                 620
Cys Lys Ala Asn Asn Thr Trp Asp Pro Glu Lys Pro Leu Cys Lys Lys
625                 630                 635                 640
```

-continued

```
Glu Gly Cys Glu Pro Met Arg Val His Gly Leu Pro Asp Asp Ser His
            645                 650                 655

Ile Lys Leu Val Lys Arg Thr Cys Gln Asn Gly Tyr Gln Leu Thr Gly
            660                 665                 670

Tyr Thr Tyr Glu Lys Cys Gln Asn Ala Glu Asn Gly Thr Trp Phe Lys
            675                 680                 685

Lys Ile Glu Val Cys Thr Val Ile Leu Cys Gln Pro Pro Lys Ile
690                 695                 700

Ala Asn Gly Gly His Thr Gly Met Met Ala Lys His Phe Leu Tyr Gly
705                 710                 715                 720

Asn Glu Val Ser Tyr Glu Cys Asp Glu Gly Phe Tyr Leu Leu Gly Glu
            725                 730                 735

Lys Ser Leu Gln Cys Val Asn Asp Ser Lys Gly His Gly Ser Trp Ser
            740                 745                 750

Gly Pro Pro Pro Gln Cys Leu Gln Ser Ser Pro Leu Thr His Cys Pro
            755                 760                 765

Asp Pro Glu Val Lys His Gly Tyr Lys Leu Asn Lys Thr His Ser Ala
            770                 775                 780

Phe Ser His Asn Asp Ile Val His Phe Val Cys Asn Gln Gly Phe Ile
785                 790                 795                 800

Met Asn Gly Ser His Leu Ile Arg Cys His Thr Asn Asn Thr Trp Leu
            805                 810                 815

Pro Gly Val Pro Thr Cys Ile Arg Lys Ala Ser Leu Gly Cys Gln Ser
            820                 825                 830

Pro Ser Thr Ile Pro Asn Gly Asn His Thr Gly Gly Ser Ile Ala Arg
            835                 840                 845

Phe Pro Pro Gly Met Ser Val Met Tyr Ser Cys Tyr Gly Phe Leu
            850                 855                 860

Met Ala Gly Glu Ala Arg Leu Ile Cys Thr His Glu Gly Thr Trp Ser
865                 870                 875                 880

Gln Pro Pro Pro Phe Cys Lys Glu Val Asn Cys Ser Phe Pro Glu Asp
            885                 890                 895

Thr Asn Gly Ile Gln Lys Gly Phe Gln Pro Gly Lys Thr Tyr Arg Phe
            900                 905                 910

Gly Ala Thr Val Thr Leu Glu Cys Glu Asp Gly Tyr Thr Leu Glu Gly
            915                 920                 925

Ser Pro Gln Ser Gln Cys Gln Asp Asp Ser Gln Trp Asn Pro Pro Leu
930                 935                 940

Ala Leu Cys Lys Tyr Arg Arg Trp Ser Thr Ile Pro Leu Ile Cys Gly
945                 950                 955                 960

Ile Ser Val Gly Ser Ala Leu Ile Ile Leu Met Ser Val Gly Phe Cys
            965                 970                 975

Met Ile Leu Lys His Arg Glu Ser Asn Tyr Tyr Thr Lys Thr Arg Pro
            980                 985                 990

Lys Glu Gly Ala Leu His Leu Glu Thr Arg Glu Val Tyr Ser Ile Asp
            995                 1000                1005

Pro Tyr Asn Pro Ala Ser
    1010
```

<210> SEQ ID NO 29
<211> LENGTH: 1033
<212> TYPE: PRT
<213> ORGANISM: Artificial Sequence
<220> FEATURE:
<223> OTHER INFORMATION: Description of Artificial Sequence:/note = synthetic construct

<400> SEQUENCE: 29

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Val Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
        355                 360                 365

Tyr Thr Tyr Asn Asp Thr Val Ile Phe Ala Cys Met Phe Gly Phe Thr
    370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
```

-continued

```
                405                 410                 415
Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
            450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                485                 490                 495

Glu Gly Tyr Lys Leu Ser Gly Ser Val Tyr Gln Glu Cys Gln Gly Thr
            500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
        530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
            580                 585                 590

Cys Lys Leu Ser Leu Leu Ala Val Gln Cys Ser His Val His Ile Ala
            595                 600                 605

Asn Gly Tyr Lys Ile Ser Gly Lys Glu Ala Pro Tyr Phe Tyr Asn Asp
        610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                645                 650                 655

Cys Glu Lys Glu Thr Cys Gln His Val Arg Gln Ser Leu Gln Glu Leu
            660                 665                 670

Pro Ala Gly Ser Arg Val Glu Leu Val Asn Thr Ser Cys Gln Asp Gly
            675                 680                 685

Tyr Gln Leu Thr Gly His Ala Tyr Gln Met Cys Gln Asp Ala Glu Asn
        690                 695                 700

Gly Ile Trp Phe Lys Lys Ile Pro Leu Cys Lys Val Ile His Cys His
705                 710                 715                 720

Pro Pro Pro Val Ile Val Asn Gly Lys His Thr Gly Met Met Ala Glu
                725                 730                 735

Asn Phe Leu Tyr Gly Asn Glu Val Ser Tyr Glu Cys Asp Gln Gly Phe
            740                 745                 750

Tyr Leu Leu Gly Glu Lys Lys Leu Gln Cys Arg Ser Asp Ser Lys Gly
            755                 760                 765

His Gly Ser Trp Ser Gly Pro Ser Pro Gln Cys Leu Arg Ser Pro Pro
        770                 775                 780

Val Thr Arg Cys Pro Asn Pro Glu Val Lys His Gly Tyr Lys Leu Asn
785                 790                 795                 800

Lys Thr His Ser Ala Tyr Ser His Asn Asp Ile Val Tyr Val Asp Cys
                805                 810                 815

Asn Pro Gly Phe Ile Met Asn Gly Ser Arg Val Ile Arg Cys His Thr
            820                 825                 830
```

-continued

```
Asp Asn Thr Trp Val Pro Gly Val Pro Thr Cys Met Lys Lys Ala Phe
        835             840             845

Ile Gly Cys Pro Pro Pro Lys Thr Pro Asn Gly Asn His Thr Gly
    850             855             860

Gly Asn Ile Ala Arg Phe Ser Pro Gly Met Ser Ile Leu Tyr Ser Cys
865             870             875                         880

Asp Gln Gly Tyr Leu Leu Val Gly Glu Ala Leu Leu Leu Cys Thr His
                885             890             895

Glu Gly Thr Trp Ser Gln Pro Ala Pro His Cys Lys Glu Val Asn Cys
            900             905             910

Ser Ser Pro Ala Asp Met Asp Gly Ile Gln Lys Gly Leu Glu Pro Arg
        915             920             925

Lys Met Tyr Gln Tyr Gly Ala Val Val Thr Leu Glu Cys Glu Asp Gly
    930             935             940

Tyr Met Leu Glu Gly Ser Pro Gln Ser Gln Cys Gln Ser Asp His Gln
945             950             955             960

Trp Asn Pro Pro Leu Ala Val Cys Arg Ser Arg Ser Leu Ala Pro Val
            965             970             975

Leu Cys Gly Ile Ala Ala Gly Leu Ile Leu Leu Thr Phe Leu Ile Val
            980             985             990

Ile Thr Leu Tyr Val Ile Ser Lys His Arg Glu Arg Asn Tyr Tyr Thr
        995             1000            1005

Asp Thr Ser Gln Lys Glu Ala Phe His Leu Glu Ala Arg Glu Val Tyr
    1010            1015            1020

Ser Val Asp Pro Tyr Asn Pro Ala Ser
1025            1030
```